(12) United States Patent  (10) Patent No.: US 6,323,218 B1
Bush et al.  (45) Date of Patent: Nov. 27, 2001

(54) AGENTS FOR USE IN THE TREATMENT OF ALZHEIMER'S DISEASE

(75) Inventors: Ashley I. Bush, Somerville; Xudong Huang, Cambridge; Craig S. Atwood, Somerville; Rudolph E. Tanzi, Canton, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/038,154

(22) Filed: Mar. 11, 1998

(51) Int. Cl.$^7$ .......................... A61K 31/47; A61K 31/53; A61K 31/40; A61K 31/105
(52) U.S. Cl. ..................... 514/311; 514/244; 514/420; 514/707
(58) Field of Search ................... 514/311, 244, 514/420, 707

(56) References Cited

U.S. PATENT DOCUMENTS

| | | |
|---|---|---|
| 5,110,493 | 5/1992 | Cherng-Chyi et al. ............ 514/413 |
| 5,373,021 | 12/1994 | Marangos ............ 514/483 |
| 5,466,680 * | 11/1995 | Rudy ............ 514/57 |
| 5,688,516 | 11/1997 | Raad et al. ............ 424/409 |
| 5,688,651 | 11/1997 | Solomon ............ 435/7.1 |
| 5,705,401 | 1/1998 | Masters et al. ............ 436/518 |
| 5,721,106 | 2/1998 | Maggio et al. ............ 435/7.8 |
| 5,927,283 | 7/1999 | Abraham et al. ............ 128/898 |
| 5,980,914 * | 11/1999 | Gerolymatos ............ 424/400 |
| 5,994,323 * | 11/1999 | Gerolymatos ............ 514/52 |
| 6,001,852 * | 12/1999 | Gerolymatos ............ 514/311 |

FOREIGN PATENT DOCUMENTS

| | | |
|---|---|---|
| WO 92/18111 | 10/1992 | (WO) . |
| WO 93/10459 | 5/1993 | (WO) . |
| WO 93/24451 | 12/1993 | (WO) . |
| WO 94/04167 | 3/1994 | (WO) . |
| WO 95/31199 | 11/1995 | (WO) . |
| WO 96/28471 | 9/1996 | (WO) . |
| WO 97/09976 | 3/1997 | (WO) . |
| WO 97/36885 | 10/1997 | (WO) . |
| WO 98/06403 | 2/1998 | (WO) . |
| WO 99/09981 | 3/1999 | (WO) . |
| WO 99/18432 | 4/1999 | (WO) . |

OTHER PUBLICATIONS

Gutierrez–Correa, J. and A.O.M. Stoppani, Free Rad. Res. 22(3): 239–250 (Mar. 1995) (publisher: Harwood Academic Publishers GmbH).
Lodemann, E., Naturwissenschaften 66(9): 462–466 (Sep. 1979) (publisher: Springer–Verlag).
Sue, Y.–J. et al., Annals of Emergency Medicine 24(4): 709–712 (Oct. 1994) (publisher: American College of Emergency Physicians).*
Atwood, C.S. et al., "Role of Free Radicals and Metal Ions in the Pathogenesis of Alzheimer's Disease," in *Metal Ions in Biological Systems*, Sigel, A. and Sigel H., eds., vol. 36, Ch. 10, Marcel Dekker, Inc., New York, pp. 309–364 (1999).
Huang, X., et al., "The Aβ Peptide of Alzheimer's Disease Directly Produces Hydrogen Peroxide through Metal Ion Reduction," *Biochem.* 38:7609–7616, American Chemical Society (Jun. 1999).
McKeon–O'Mally, C., et al., "Potential Therapeutic Targets for Alzheimer's Disease," *Emerging Therapeutic Targets* 2:157–179, Ashley Publications Ltd. (Feb. 1998).
International Search Report for PCT/US00/11715, mailed Aug. 30, 2000.

(List continued on next page.)

*Primary Examiner*—Kevin E. Weddington
(74) *Attorney, Agent, or Firm*—Sterne, Kessler, Goldstein & Fox P.L.L.C.

(57) ABSTRACT

The invention relates to the identification of pharmacological agents to be used in the treatment of Alzheimer's disease and related pathological conditions and compositions for treatment of conditions caused by amyloidosis, Aβ-mediated formation of ROS, or both, such as Alzheimer's disease.

36 Claims, 58 Drawing Sheets

OTHER PUBLICATIONS

Bacon, P.A. et al., "Rheumatoid Disease, Amyloidosis and its Treatment with Penicillamine," *Eur. J. Rheum. Inflamm.* 2:70–74 (1979).

Sayre, L.M., "Alzheimer's Precursor Protein and the Use of Bathocuproine for Determining Reduction of Copper(II)," *Science* 274:1933–1934 (Dec. 1996).

International Search Report for International Application No. PCT/US99/05291, mailed Oct. 29, 1999.

Cuajungco, M.P., and Lees, G.J., "Zinc and Alzheimer's disease: is there a direct link?," *Brain Res. Rev.* 23:219–236 (Apr. 1997).

Goodman, Y., et al., "Nordihydroguaiaretic acid protects hippocampal neurons against amyloid β–peptide toxicity, and attenuates free radical and calcium accumulation," *Brain Res.* 654:171–176 (1994).

Skinner, M., et al., "Observations on the amyloid–degrading activity of serum and its relationship to human neutrophil elastase," *Chemical Abstracts*, 101(23):453 col. 1, Abstract No. 101:208677n (1984).

International Search Report for International Application No. PCT/US98/04683, miled Jun. 19, 1998.

Barrow, C.J., and Zagorski, M.G., "Solution Structures of β Peptide and Its Constituent Fragments: Relation to Amyloid Deposition," *Science* 253:179–182 (1991).

Barrow, C.J., et al., "Solution Conformations and Aggregational Properties of Synthetic Amyloid β–Peptides of Alzheimer's Disease," *J. Mol. Biol.* 225:1075–1093 (1992).

Basun, H., et al., "Metals and trace elements in plasma and cerebrospinal fluid in normal ageing and Alzheimer's disease," *J. Neural Transm. [P–D Sect.]* 3:231–258 (1991).

Behl, C., et al., "Hydrogen Peroxide Mediates Amyloid β Protein Toxicity," *Cell* 77:817–827 (1994).

Bruce, A.J., et al., "β–Amyloid toxicity in organotypic hippocampal cultures: Protection by EUK–8, a synthetic catalytic free radical scavenger," *Proc. Natl. Acad. Sci. USA* 93:2312–2316 (1996).

Burdick, D., et al., "Assembly and Aggregation Properties of Synthetic Alzheimer's A4/β Amyloid Peptide Analogs," *J. Biol. Chem.* 267:546–554 (1992).

Burns, J.A., et al., "Selective Reduction of Disulfides by Tris(2–carboxyethyl)phosphine," *J. Org. Chem.* 56:2648–2650 (1991).

Busciglio, J., and Yankner, B.A., "Apoptosis and increased generation of reactive oxygen species in Down's Syndrome neurons in vitro," *Nature* 378:776–779 (1995).

Bush, A.I., et al., "A Novel Zinc(II) Binding Site Modulates the Function of the βA4 Amyloid Protein Precursor of Alzheimer's Disease," *J. Biol. Chem.* 268:16109–16112 (1993).

Bush, A.I., et al., "Modulation of Aβ Adhesiveness and Secretase Site Cleavage by Zinc," *J. Biol. Chem.* 269:12152–12158 (1994).

Bush, A.I., et al., "Rapid Induction of Alzheimer Aβ Amyloid Formation by Zinc," *Science* 265: 1464–1467 (1994).

Bush, A.I., et al., "The Amyloid β–Protein Precursor and Its Mammalian Homologues," *J. Biol. Chem.* 269:26618–26621 (1994).

Bush, A.I., et al. in: "Zinc and Alzheimer's Disease," *Science* 268:1920–1923 (1995).

Butterfield, D.A., et al., "β–Amyloid Peptide Free Radical Fragments Initiate Synaptosomal Lipoperoxidation in a Sequence–Specific Fashion: Implications to Alzheimer's Disease," *Biochem. Biophys. Res. Commun.* 200:710–715 (1994).

Butterfield, D.A., et al., "Aβ(25–35) Peptide Displays $H_2O_2$–Like Reactivity Towards Aqueous $Fe^{2+}$, Nitroxide Spin Probes, and Synaptosomal Membrane Proteins," *Life Sci.* 58:217–228 (1996).

Cherny, R.A., et al., "The Aggregation of Aβ in Human Brain is Mediated by Zinc," *Soc. Neurosci. Abstr.* 23:534, Abstract 209.6 (Oct. 1997).

Chong, Y.–H, and Sug, Y.–H., "Aggregation of amyloid precursor proteins by aluminum in vitro," *Brain Research* 670:137–141 (1995).

Colaco, C.A.L.S., et al., "The role of the Maillard reaction in other pathologies: Alzheimer's disease," *Nephrol. Dial. Transplant.* 11(Suppl. 5):7–12 (1996).

Doré, S., et al., "Insulin–like growth factor I protects and rescues hippocampal neurons against β–amyloid– and human amylin–induced toxicity," *Proc. Natl. Acad. Sci. USA* 94:4772–4777 (Apr. 1997).

Dyrks, T., et al., "Amyloidogenicity of βA4 and βA4–bearing Amyloid Protein Precursor Fragments by Metal–catalyzed Oxidation," *J. Biol. Chem.* 267:18210–18217 (1992).

Esler, W.P., et al., "Zinc–Induced Aggregation of Human and Rat β–Amyloid Peptides In Vitro," *J. Neurochem.* 66:723–732 (1996).

Esler, W.P., et al., "Aβ deposition inhibitor screen using synthetic amyloid," *Nat. Biotechnol.* 15:258–263 (Mar. 1997).

Fitzgerald, D.J., "Zinc and Alzheimer's Disease," *Science* 268:1920 (1995).

Fraser, P.E., et al., "pH–dependent structural transitions of Alzheimer amyloid peptides," *Biophys. J.* 60:1190–1201 (1991).

Frederikse, P.H., et al., "Oxidative Stress Increases Production of β–Amyloid Precursor Protein and β–Amyloid (Aβ) in Mammalian Lenses, and Aβ Has Toxic Effects on Lens Epithelial Cells," *J. Biol. Chem.* 271:10169–10174 (1996).

Frieden, E., "Ceruloplasmin: A Multi–functional Cupro–protein of Vertebrate Plasma," in: *Inflammatory Diseases and Copper*, Sorenson, J.R.J., ed., Clifton, N.J.: Humana Press, pp. 159–169 (1982).

Giampaolo, V., "Copper and Inflammation," in: *Inflammatory Diseases and Copper*, Sorenson, J.R.J., ed., Clifton, N.J.: Humana Press, pp. 329–345 (1982).

Giulian, D., et al., "Specific Domains of β–Amyloid from Alzheimer Plaque Elicit Neuron Killing in Human Microglia," *J. Neurosci.* 16:6021–6037 (1996).

Glenner, G.G., and Wong, C.W., "Alzheimer's Disease: Initial Report of the Purification and Characterization of a Novel Cerebrovascular Amyloid Protein," *Biochem. Biophys. Res. Commun.* 120:885–890 (1984).

Golde, T.E., et al., "Processing of the Amyloid Protein Precursor to Potentially Amyloidogenic Derivatives," *Science* 255: 728–730 (1992).

Goodman, Y., and Mattson, M.P., "Secreted Forms of β–Amyloid Precursor Protein Protect Hippocampal Neurons against Amyloid β–Peptide–Induced Oxidative Injury," *Exp. Neurol.* 128:1–12 (1994).

Gutteridge, J.M.C., and Wilkins, S., "Copper Salt–Dependent Hydroxyl Radical Formation Damage to Proteins Acting as Antioxidants," *Biochim. Biophys. Acta* 759:38–41 (1983).

Haley, J.V., "Zinc Sulfate and Wound Healing," *J. Surg. Res.* 27:168–174 (1979).

Halliwell, B., and Gutteridge, J.M.C., "Oxygen toxicity, oxygen radicals, transition metals and disease," *Biochem. J.* 219:1–14 (1984).*

Halliwell, B., "Reactive Oxygen Species and the Central Nervous System," *J. Neurochem.* 59:1609–1623 (1992).*

Han, J.C., and Han, G.Y., "A Procedure for Quantitative Determination of Tris(2–carboxyethyl)phosphine, an Odorless Reducing Agent More Stable and Effective Than Dithiothreitol," *Anal. Biochem.* 220:5–10 (1994).*

Han, J., et al., "Quantitation of Hydrogen Peroxide Using Tris(2–carboxyethyl)phosphine," *Anal. Biochem.* 234:107–109 (1996).

Hansen, M.B., et al., "Re–examination and further development of a precise and rapid dye method for measuring cell growth/cell kill," *J. Immunol. Meth.* 119:203–210 (1989).

Harris, M.E., et al., "Direct Evidence of Oxidative Injury Produced by the Alzheimer's β–Amyloid Peptide (1–40) in Cultured Hippocampal Neurons," *Exp. Neurol.* 131:193–202 (1995).

Hensley, K., et al., "A model for β–amyloid aggregation and neurotoxicity based on free radical generation by the peptide: Relevance to Alzheimer disease," *Proc. Natl. Acad. Sci.* 91:3270–3274 (1994).

Hensley, K., et al., "Reactive Oxygen Species as Causal Agents in the Neurotoxicity of the Alzheimer's Disease–Associated Amyloid Beta Peptide," *Ann N. Y. Acad. Sci.* 786:120–134 (1996).

Hesse, L., et al., "The βA4 amyloid precursor protein binding to copper, " *FEBS Lett.* 349:109–116 (1994).

Hilbich, C., et al., "Aggregation and Secondary Structure of Synthetic Amyloid βA4 Peptides of Alzheimer's Disease," *J. Mol. Biol.* 218:149–163 (1991).

Hilbich, C., et al., "Substitutions of Hydrophobic Amino Acids Reduce the Amyloidogenicity of Alzheimer's Disease βA4 Peptides," *J. Mol. Biol.* 228:460–473 (1992).

Hsu, J.M., et al., "Zinc Deficiency and Incorporation of [14]C–labeled Methionine into Tissue Proteins in Rats," *J. Nutrition* 99:425–432 (1969).

Huang, X., et al., "Zinc–induced Alzheimer's Aβ1–40 Aggregation Is Mediated by Conformational Factors," *J. Biol. Chem.* 272: 26464–26470 (Oct. 1997).

Ida, N., et al., "Analysis of Heterogeneous βA4 Peptides in Human Cerebrospinal Fluid and Blood by a Newly Developed Sensitive Western Blot Assay," *J. Biol. Chem.* 271:22908–22914 (1996).

Jarrett, J.T., and Lansbury, Jr., P.T., "Amyloid Fibril Formation Requires a Chemically Discriminating Nucleation Event: Studies of an Amyloidogenic Sequence from the Bacterial Protein OsmB," *Biochemistry* 31:12345–12352 (1992).

Jarrett, J.T., et al. "The Carboxy Terminus of the β Amyloid Protein Is Critical for the Seeding of Amyloid Formation: Implications for the Pathogenesis of Alzheimer's Disease," *Biochemistry* 32:4693–4697 (1993).

Kirshenbaum, K., and Daggett, V., "pH–Dependent Conformations of the Amyloid β(1–28) Peptide Fragment Explored Using Molecular Dynamics," *Biochemistry* 34:7629–7639 (1995).

Koh, J.Y., and Choi, D.W., "Quantitative determination of glutamate mediated cortical neuronal injury in cell culture by lactate dehydrogenase efflux assay," *J. Neurosci. Meth.* 20:83–90 (1987).

Kotaki, H., et al., "Intestinal Absorption and Metabolism of Clioquinol in the Rat," *J. Pharm. Dyn.* 6:881–887 (1983).

Kuo, Y.–M., et al., "Water–soluble Aβ (N–40, N–42) Oligomers in Normal and Alzheimer Disease Brains," *J. Biol. Chem.* 271:4077–4081 (1996).

Landers, J.W., and Zak, B., "Determination of Serum Copper and Iron in a Single Small Sample," *Am. J. Clin. Pathol.* 29:590–592 (1958).

Lindeman, R.D., et al., "Myocardial zinc metabolism in experimental myocardial infarction," *J. Lab. Clin. Med.* 81:194–204 (1973).*

Linert, W., et al., "Dopamine, 6–hydroxydopamine, iron, and dioxygen—their mutual interactions and possible implication in the development of Parkinson's disease," *Biochim. Biophys. Acta* 1316:160–168 (1996).*

Lohr, J.B., "Oxygen Radicals and Neuropsychiatric Illness," *Arch. Gen. Psychiatry* 48:1097–1106 (1991).*

Maggio, J.E., et al., "Zinc and Alzheimer's Disease," *Science* 268:1920–1921 (1995).

Mantyh, P.W., et al., "Aluminum, Iron, and Zinc Ions Promote Aggregation of Physiological Concentrations of β–Amyloid Peptide," *J. Neurochem.* 61:1171–1174 (1993).

Masters, C.L., et al., "Amyloid plaque core protein in Alzheimer disease and Down syndrome," *Proc. Natl. Acad. Sci. USA* 82:4245–4249 (1985).

Masters, C.L., et al., "Neuronal origin of a cerebral amyloid: neurofibrillary tangles of Alzheimer's disease contain the same protein as the amyloid of plaque cores and blood vessels," *EMBO J.* 4:2757–2763 (1985).

McGeer, P.L., and McGeer, E.G., "The inflammatory response system of brain: implications for therapy of Alzheimer and other neurodegenerative diseases," *Brain Res. Rev.* 21:195–218 (1995).

McLachlan, D.R.C., et al., "Intramuscular desferrioxamine in patients with Alzheimer's disease," *Lancet* 337:1304–1308 (1991).

Menkin, V., "Studies on Inflammation. X. The Cytological Picture of an Inflammatory Exudate in Relation to its Hydrogen Ion Concentration," *Am. J. Pathol.* 10:193–210 (1934).

Michikawa, M., et al., "Oxygen Radical–Induced Neurotoxicity in Spinal Cord Neuron Cultures," *J. Neurosci. Res.* 37:62–70 (1994).

Milanino, R., et al., "Copper and the Inflammatory Process," *Advances in Inflammation Research* 1:281–291 (1979).

Mok, S.S., et al., "A Novel Metalloprotease in Rat Brain Cleaves the Amyloid Precursor Protein of Alzheimer's Disease Generating Amyloidogenic Fragments," *Biochemistry* 36:156–163 (Jan. 1997).

Multhaup, G., et al., "Interaction between the zinc(II) and the heparin binding site of the Alzheimer's disease βA4 amyloid precursor protein (APP), " *FEBS Lett.* 355:151–154 (1994).

Multhaup, G., et al., "The Amyloid Precursor Protein of Alzheimer's Disease in the Reduction of Copper(II) to Copper (I)," *Science* 271:1406–1409 (1996).

Münch, G., et al., "Advanced glycation endproducts in ageing and Alzheimer's disease," *Brain Res. Rev.* 23:134–143 (Feb. 1997).

Owen, C.A., Jr., "Uptake of $^{67}$Cu by Ceruloplasmin In Vitro (38878)," *Proc. Soc. Exp. Biol. Med. 149*:681–682 (1975).

Padmanabhan, G., et al., "Clioquinol," in:*Analytical Profiles of Drug Substances*, vol. 18, Florey, K., ed., Academic Press, Inc.:San Diego, CA, pp. 57–90 (1989).

Peters, G., and Rodgers, M.A.J., "Single–Electron Transfer from NADH Analogues to Singlet Oxygen," *Biochim. Biophys. Acta 637*:43–52 (1981).

Pierce, J.E.S., et al., "Immunohistochemical Characterization of Alterations in the Distribution of Amyloid Precursor Proteins and β–Amyloid Peptide after Experimental Brain Injury in the Rat," *J. Neurosci. 16*:1083–1090 (1996).

Potempa, L.A., et al., "Effect of Divalent Metal Ions and pH upon the Binding Reactivity of Human Serum Amyloid P Component, a C–roactive Protein Homologue, for Zymosan," *J. Biol. Chem. 260*:12142–12147 (1985).

Richardson, J.S., et al., "On the Possible Role of Iron–Induced Free Radical Peroxidation in Neural Degeneration in Alzheimer's Disease," *Ann. N.Y. Acad. Sci. 648*:326–327 (1992).

Roberts, G.W., et al., "βA4 amyloid protein deposition in brain after head trauma," *Lancet 338*:1422–1423 (1991).

Rogers, J., et al., "Clinical trial of indomethacin in Alzheimer's disease," *Neurology 43*:1609–1611 (1993).

Roher, A.E., et al., "Morphology and Toxicity of Aβ–(1–42) Dimer Derived from Neuritic and Vascular Amyloid Deposits of Alzheimer'Disease," *J. Biol. Chem. 271*:20631–20635 (1996).

Sano, M., et al., "A Controlled Trial of Selegiline, Alpha–Tocopherol, or Both as Treatment for Alzheimer's Disease," *N.Engl. J. Med. 336*:1216–1222 (Apr. 1997).

Schnabel, J., "New Alzheimer's Therapy Suggested," *Science 260*:1719–1720 (1993).

Schubert, D., and Chevion, M., "The Role of Iron in Beta Amyloid Toxicity," *Biochem. Biophys. Res. Comm. 216*:702–707 (1995).

Shiraki, H., "Neuropathological aspects of the etiopathogenesis of subacute myelo–optico–neuropathy (SMON)," in: *Handbook of Clinical Neurology*, vol. 37, Vinken, P.J., and Bruyn, G.W., eds., North–Holland Publishing Company: Amsterdam, pp. 141–198 (1979).

Smalheiser, N.R., and Swanson, D.R., "Indomethacin and Alzheimer's disease," *Neurology 46*:583 (1996).

Smith, M.A., et al., "Iron accumulation in Alzheimer disease is a source of redox–generated free radicals," *Proc. Natl. Acad. Sci. USA 94*:9866–9868 (Sep. 1997).

Smith, M.A., et al., "Radical AGEing in Alzheimer's disease," *Trends Neurosci. 18*:172–176 (1995).

Soto, C., et al., "Structural Determinants of the Alzheimer's Amyloid β–Peptide," *J. Nerochem. 63*:1191–1198 (1994).

Stankovic, A., and Mitrovic, D.R., "Aluminum Salts Stimulate Luminol–Enhanced Chemi luminescence Production by Human Neutrophils," *Free Rad. Res. Comms. 14*:47–55 (1991).

Tateishi, J., et al., "Neurotoxicity of Clioquinol in Laboratory Animals," *Lancet 2*:1095 (1972).

Tateishi, J., et al., "Experimental Myelo–optic Neuropathy Induced by Clioquinol," *Acta Neuropath. (Berl.) 24*:304–320 (1973).

Teller, J.K., et al., "Presence of soluble amyloid β–peptide precedes amyloid plaque formation in Down's Syndrome," *Nature Med. 2*:93–95 (1996).

Terhune, M.W., and Sandstead, H.H., "Decreased RNA Polymerase Activity in Mammalian Zinc Deficiency," *Science 177*:68–69 (1972).

Thomas, T., et al., "β–Amyloid–mediated vasoactivity and vascular endothelial damage," *Nature 380*:168–171 (1996).

Tomiyama, T., et al., "Rifampicin Prevents the Aggregation and Neurotoxicity of Amyloid β Protein In Vitro," *Biochem. Biophys. Res. Comm. 204*:76–83 (1994).

Tomiyama, T., et al., "Inhibition of Amyloid β Protein Aggregation and Neurotoxicity by Rifampicin," *J. Biol. Chem. 271*:6839–6844 (1996).

Tomski, S.J., and Murphy, R.M., "Kinetics of Aggregation of Synthetic β–Amyloid Peptide," *Arch. Biochem. Biophys. 294*:630–638 (1992).

Treuhaft, P.S., and McCarty, D.J., "Synovial Fluid pH, Lactate, Oxygen and Carbon Dioxide Partial Pressure in Various Joint Diseases," *Arthritis Rheum. 14*:475–484 (1971).

Weismann, K., and Knudsen, L., "Effects of Penicillamine and Hydroxyquinoline on Absorption of Orally Ingested $^{65}$Zinc in the Rat," *J. Invest. Dermatol. 71*:242–244 (1978).

Wood, S.J., et al., "Physical, Morphological and Functional Differences between pH 5.8 and 7.4 Aggregates of the Alzheimer's Amyloid Peptide Aβ," *J. Mol. Biol. 256*:870–877 (1996).

Yates, C.M., et al., "Enzyme Activities in Relation to pH and Lactate in Postmortem Brain in Alzheimer–Type and Other Dementias," *J. Neurochem. 55*:1624–1630 (1990).

Zagorski, M.G., and Barrow, C.J., "NMR Studies of Amyloid β–Peptides: Proton Assignments, Secondary Structure, and Mechanism of an α–Helix→β–Sheet Conversion for a Homologous, 28–Residue, N–Terminal Fragment," *Biochemistry 31*:5621–5631 (1992).

* cited by examiner

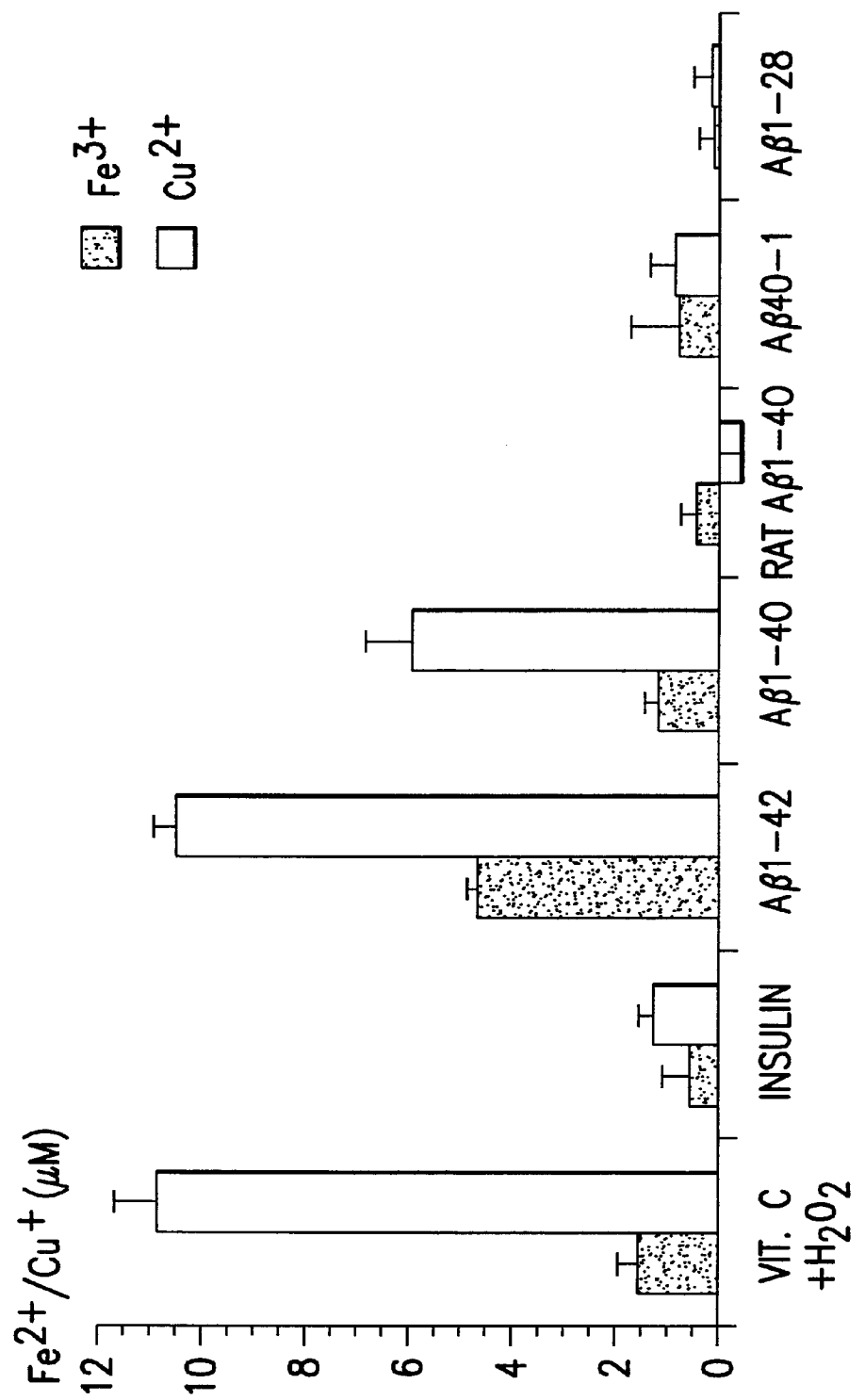

Brain specimen #1

Brain specimen #2

| | S1 | S2 | S1 | S2 | S1 | S2 | S1 | S2 |
|---|---|---|---|---|---|---|---|---|
| Dilution | 0 | | 100% | | 10% | | 1% | |

AGENTS FOR USE IN THE TREATMENT OF ALZHEIMER'S DISEASE

STATEMENT AS TO RIGHTS TO INVENTIONS MADE UNDER FEDERALLY-SPONSORED RESEARCH AND DEVELOPMENT

BACKGROUND OF THE INVENTION

Part of the work performed during the development of this invention utilized U.S. Government Funds under Grant No. R29AG12686 from the National Institutes of Health. The government may have certain rights in this invention.

1. Field of the Invention

This invention is in the field of medicinal chemistry. In particular, the invention is related to compositions for treatment of Alzheimer's disease.

2. Related Art

Polymers of Abeta (Aβ), the 4.3 kD, 39–43 amino acid peptide product of the transmembrane protein, amyloid protein precursor (APP), are the main components extracted from the neuritic and vascular amyloid of Alzheimer's disease (AD) brains. Aβ deposits are usually most concentrated in regions of high neuronal cell death, and may be present in various morphologies, including amorphous deposits, neurophil plaque amyloid, and amyloid congophilic angiopathy (Masters, C. L., et al., *EMBO J.* 4:2757 (1985); Masters, C. L. el al., *Proc. Natl. Acad. Sci. USA* 82: 4245 (1985)). Growing evidence suggests that amyloid deposits are intimately associated with the neuronal demise that leads to dementia in the disorder.

The presence of an enrichment of the 42 residue species of Aβ in these deposits suggests that this species is more pathogenic. The 42 residue form of Aβ ($A\beta_{1-42}$), while a minor component of biological fluids, is highly enriched in amyloid, and genetic studies strongly implicate this protein in the etiopathogenesis of AD. Amyloid deposits are decorated with inflammatory response proteins, but biochemical markers of severe oxidative stress such as peroxidation adducts, advanced glycation end-products, and protein cross-linking are seen in proximity to the lesions. To date, the cause of Aβ deposits is unknown, although it is believed that preventing these deposits may be a means of treating the disorder.

When polymers of Aβ are placed into culture with rat hippocampal neurons, they are neurotoxic (Kuo, Y-M., et al., *J. Biol. Chem.* 271:4077–81 (1996); Roher, A. E., et al., *Journal of Biological Chemistry* 271:20631–20635 (1996)). The mechanism underlying the formation of these neurotoxic polymeric Aβ species remains unresolved. The overexpression of Aβ alone cannot sufficiently explain amyloid formation, since the concentration of Aβ required for precipitation is not physiologically plausible. That alterations in the neurochemical environment are required for amyloid formation is indicated by its solubility in neural phosphate buffer at concentrations of up to 16 mg/ml (Tomski, S. & Murphy, R. M., *Archives of Biochemistry and Biophysics* 294:630 (1992)), in biological fluids such as cerebrospinal fluid (CSF) (Shoji, M., et al., *Science* 258:126 (1992); Golde, T. E., etal. *Science*, 255(5045):728–730 (1992); Seubert, P., el al., *Nature* 359:325 (1992); Haass, C., et al., *Nature* 359:322 (1992)) and in the plaque-free brains of Down's syndrome patients (Teller, J. K., et al., *Nature Medicine* 2:93–95 (1996)).

Studies into the neurochemical vulnerability of Aβ to form amyloid have suggested altered zinc and [H+] homeostasis as the most likely explanations for amyloid deposition. Aβ is rapidly precipitated under mildly acidic conditions in vitro (pH 3.5–6.5) (Barrow, C. J. & Zagorski, M. G., *Science* 253:179–182 (1991); Fraser, P. E., et al., *Biophys. J.* 60:1190–1201 (1991); Barrow, C. J., et al., *J. Mol. Biol.* 225:1075–1093 (1992); Burdick, D., *J. Biol. Chem.* 267:546–554 (1992); Zagorski, M. G. & Barrow, C. J., *Biochemistry* 31:5621–5631 (1992); Kirshenbaum, K. & Daggett, V., *Biochemistry* 34:7629–7639 (1995); Wood, S. J., et al.,*J. Mol. Biol.* 256:870–877 (1996)). Recently, it has been shown that the presence of certain biometals, in particular redox inactive $Zn^{2+}$ and, to a lesser extent, redox active $Cu^{2+}$ and $Fe^{3+}$, markedly increases the precipitation of soluble Aβ (Bush, A. I., et al., *J. Biol. Chem.* 268:16109 (1993); Bush, A. I., et al.,*J. Biol. Chem.* 269:12152 (1994); Bush, A. I., et al., *Science* 265:1464 (1994); Bush, A. I., el al., *Science* 268:1921 (1995)). At physiological pH, $A\beta_{1-40}$ specifically and saturably binds $Zn^{2+}$, manifesting high affinity binding ($K_D$=107 nM) with a 1:1 ($Zn^{2+}$:Aβ) stoichiometry, and low affinity binding ($K_D$=5.2 μM) with a 2:1 stoichiometry.

The reduction by APP of copper (II) to copper (I) may lead to irreversible Aβ aggregation and SDS-resistant polymerization. This reaction may promote an environment that would enhance the production of hydroxyl radicals, which may contribute to oxidative stress in AD (Multhaup, G., et al., *Science* 271:1406–1409 (1996)). A precedence for abnormal Cu metabolism already exists in the neurodegenerative disorders of Wilson's disease, Menkes' syndrome and possibly familial amyotrophic lateral sclerosis (Tanzi, R. E. et al., *Nature Genetics* 5:344 (1993); Bull, P. C., et al., *Nature Genetics* 5:327 (1993); Vulpe, C., et al., *Nature Genetics* 3:7 (1993); Yamaguchi, Y., et al., *Biochem. Biophys. Res. Commun.* 197:271 (1993); Chelly, J., et al., *Nature Genetics* 3:14 (1993); Wang, D. & Munoz, D. G.,*J. Neuropathol. Exp. Neurol.* 54:548 (1995); Beckman, J. S., et al., *Nature* 364:584 (1993); Hartmann, H. A. & Evenson, M. A., *Med. Hypotheses* 38:75 (1992)).

Although much fundamental pathology, genetic susceptibility and biology associated with AD is becoming clearer, a rational chemical and structural basis for developing effective drugs to prevent or cure the disease remains elusive. While the genetics of the disorder indicates that the metabolism of Aβ is intimately associated with the etiopatholgenesis of the disease, drugs for the treatment of AD have so far focused on "cognition enhancers" which do not address the underlying disease processes.

SUMMARY OF THE INVENTION

An aspect of the present invention contemplates a method for treating Alzheimer's disease (AD) in a subject, said method comprising administering to said subject an effective amount of an agent which is capable of inhibiting or otherwise reducing metal-mediated production of free radicals.

The present invention provides a method for treating AD in a subject, said method comprising administering to said subject an effective amount of an agent comprising a metal chelator and/or a metal complexing compound for a time and under conditions sufficient to inhibit or otherwise reduce metal-mediated production of free radicals by Aβ.

In one aspect, the free radicals are reactive oxygen species such as $O_2^-$ or OH•. In another aspect, the free radicals include forms of Aβ.

The agent of this aspect of the present invention may contain one or more than one compound such as a metal chelator or metal complexing compound such as but not limited to DTPA, bathocuproine, bathophenanthroline, clioquinol, penicillamine, or derivatives, homologues or analogues thereof. Alternatively, or in addition, the agent may comprise an antioxidant or other molecule capable of interfering with Aβ peptide-mediated radical formation.

One aspect of the present invention comprises an agent for use in treating AD in a subject comprising a metal chelator, metal complexing compound and/or a compound capable of inhibiting free radical formation by interaction of Aβ peptides and biometals, said agent optionally further comprising one or more pharmaceutically acceptable carriers and/or diluents.

In one aspect, the invention relates to a method of treating amyloidosis in a subject, said method comprising administering to said subject a combination of (a) a metal chelator selected from the group consisting of: bathocuproine, bathophenanthroline, DTPA, EDTA, EGTA, penicillamine, TETA, and TPEN, or hydrophobic derivatives thereof, and (b) clioquinol, for a time and under conditions to bring about said treatment; wherein said combination reduces, inhibits or otherwise interferes with Aβ-mediated production of radical oxygen species.

In a preferred embodiment, the metal chelator is bathocuproine.

In another aspect, said method further comprises administering a supplement selected from the group consisting of: ammonium salt, calcium salt, magnesium salt, and sodium salt.

In a preferred embodiment, the supplement is magnesium salt.

In another aspect, said method further comprises administering to the subject an effective amount of a compound selected from the group consisting of: rifampicin, disulfiram, and indomethacin, or a pharmaceutically acceptable salt thereof.

In yet another aspect, the invention relates to a method of treating amyloidosis in a subject, said method comprising administering to said subject an effective amount of a combination of (a) a salt of a metal chelator, wherein said chelator is selected from the group consisting of: bathocuproine, bathophenanthroline, DTPA, EDTA, EGTA, penicillamine, TETA, and TPEN, or hydrophobic derivatives thereof, and (b) clioquinol; wherein said salt of the metal chelator is selected from the group consisting of: ammonium, calcium, magnesium, and sodium; and wherein said combination reduces, inhibits or otherwise interferes with Aβ-mediated production of radical oxygen species.

In a preferred embodiment, the metal chelator is bathocuproine.

In another preferred embodiment, the salt of the metal chelator is a magnesium salt.

In another aspect, said method further comprises administering to the subject an effective amount of a compound selected from the group consisting of: rifampicin, disulfiram, and indomethacin, or a pharmaceutically acceptable salt thereof.

In yet another aspect, the invention relates to a method of treating amyloidosis in a subject, said method comprising administering to said subject an effective amount of a combination of (a) a chelator specific for copper, and (b) clioquinol; wherein said combination reduces, inhibits or otherwise interferes with Aβ-mediated production of radical oxygen species.

In a preferred embodiment, the chelator specific for copper is specific for the reduced form of copper. Most preferably, the chelator is bathocuproine or a hydrophobic derivative thereof.

In yet another aspect, the invention relates to a method of treating amyloidosis in a subject, said method comprising administering to said subject an effective amount of a combination of (a) an alkalinizing agent and (b) clioquinol; wherein said combination reduces, inhibits or otherwise interferes with Aβ-mediated production of radical oxygen species.

In a preferred embodiment, the alkalinizing agent is magnesium citrate. In another preferred embodiment, the alkalinizing agent is calcium citrate.

Still another aspect of the present invention contemplates a method of treating AD in a subject comprising administering to said subject an agent capable of promoting, inducing or otherwise facilitating resolubilization of Aβ deposits in the brain for a time and under conditions to effect said treatment.

In yet another aspect, the invention relates to a method of treating amyloidosis in a subject, said method comprising administering to said subject a combination of (a) a metal chelator selected from the group consisting of: bathocuproine, bathophenanthroline, DTPA, EDTA, EGTA, penicillamine, TETA, and TPEN, or hydrophobic derivatives thereof; and (b) clioquinol, for a time and under conditions to bring about said treatment; wherein said combination prevents formation of Aβ amyloid, promotes, induces or otherwise facilitates resolubilization of Aβ deposits, or both.

In a preferred embodiment, the metal chelator is bathocuproine.

In another aspect, said method further comprises administering a supplement selected from the group consisting of: ammonium salt, calcium salt, magnesium salt, and sodium salt.

In a preferred embodiment, the supplement is magnesium salt.

In another aspect, said method further comprises administering to the subject an effective amount of a compound selected from the group consisting of: rifampicin, disulfiram, and indomethacin, or a pharmaceutically acceptable salt thereof.

In yet another aspect, the invention relates to a method of treating amyloidosis in a subject, said method comprising administering to said subject an effective amount of a combination of (a) a salt of a metal chelator, wherein said chelator is selected from the group consisting of: bathocuproine, bathophenanthroline, DTPA, EDTA, EGTA, penicillamine, TETA, and TPEN, or hydrophobic derivatives thereof, and (b) clioquinol; wherein said salt of the metal chelator is selected from the group consisting of: ammonium, calcium, magnesium, and sodium; and wherein said combination prevents formation of Aβ amyloid, promotes, induces or otherwise facilitates resolubilization of Aβ deposits, or both.

In a preferred embodiment, the metal chelator is bathocuproine. In another preferred embodiment, the salt of the metal chelator is a magnesium salt.

In another aspect, said method further comprises administering to the subject an effective amount of a compound selected from the group consisting of: rifampicin, disulfiram, and indomethacin, or a pharmaceutically acceptable salt thereof.

In yet another aspect, the invention relates to a method of treating amyloidosis in a subject, said method comprising administering to said subject an effective amount of a combination of (a) a chelator specific for copper, and (b) clioquinol; wherein said combination prevents formation of Aβ amyloid, promotes, induces or otherwise facilitates resolubilization of Aβ deposits, or both.

In a preferred embodiment, the chelator specific for copper is specific for the reduced form of copper. Most preferably, the chelator is bathocuproine or a hydrophobic derivative thereof.

In yet another aspect, the invention relates to a method of treating amyloidosis in a subject, said method comprising administering to said subject an effective amount of a combination of (a) an alkalinizing agent and (b) clioquinol; wherein said combination prevents formation of Aβ amyloid, promotes, induces or otherwise facilitates resolubilization of Aβ deposits, or both.

In a preferred embodiment, the alkalinizing agent is magnesium citrate. In another preferred embodiment, the alkalinizing agent is calcium citrate.

Still another aspect of the invention relates to a pharmaceutical composition for treatment of conditions caused by amyloidosis, Aβ-mediated ROS formation, or both, comprising: (a) a metal chelator selected from the group consisting of: bathocuproine, bathophenanthroline, DTPA, EDTA, EGTA, penicillamine, TETA, and TPEN, or hydrophobic derivatives thereof; and (b) clioquinol, together with one or more pharmaceutically acceptable carriers or diluents.

In a preferred embodiment, the metal chelator is bathocuproine.

In another aspect, said method further comprises administering a supplement selected from the group consisting of: ammonium salt, calcium salt, magnesium salt, and sodium salt.

In a preferred embodiment, the supplement is magnesium salt.

In another aspect, said composition further comprises a compound selected from the group consisting of: rifampicin, disulfiram, and indomethacin, or a pharmaceutically acceptable salt thereof.

In yet another aspect, the invention relates to a pharmaceutical composition for treatment of conditions caused by amyloidosis, Aβ-mediated ROS formation, or both, comprising a combination of (a) a salt of a metal chelator selected from the group consisting of: bathocuproine, bathophenanthroline, DTPA, EDTA, EGTA, penicillamine, TETA, and TPEN, or hydrophobic derivatives thereof; and (b) clioquinol; wherein said salt of the metal chelator is selected from the group consisting of: ammonium, calcium, magnesium, and sodium, together with one or more pharmaceutically acceptable carriers or diluents.

In a preferred embodiment, the metal chelator is bathocuproine. In another preferred embodiment, the salt of the metal chelator is a magnesium salt.

In another aspect, said composition further comprises a compound selected from the group consisting of: rifampicin, disulfiram, and indomethacin, or a pharmaceutically acceptable salt thereof.

In yet another aspect, the invention relates to a pharmaceutical composition for treatment of conditions caused by amyloidosis, Aβ-mediated ROS formation, or both, comprising a chelator specific for copper, with one or more pharmaceutically acceptable carriers or diluents.

In a preferred embodiment, the chelator specific for copper is specific for the reduced form of copper. Most preferably, the chelator is bathocuproine or a hydrophobic derivative thereof.

In yet another aspect, the invention relates to a pharmaceutical composition for treatment of conditions caused by amyloidosis, Aβ-mediated ROS formation, or both, comprising a combination of (a) an alkalinizing agent and (b) clioquinol; together with one or more pharmaceutically acceptable carriers or diluents.

In a preferred embodiment, the alkalinizing agent is magnesium citrate. In another preferred embodiment, the alkalinizing agent is calcium citrate.

Still another aspect of the invention relates to a composition of matter comprising: (a) a metal chelator selected from the group consisting of: bathocuproine, bathophenanthroline, DTPA, EDTA, EGTA, penicillamine, TETA, and TPEN, or hydrophobic derivatives thereof; and (b) clioquinol.

In a preferred embodiment, the metal chelator is bathocuproine.

In another aspect, said method further comprises administering a supplement selected from the group consisting of: ammonium salt, calcium salt, magnesium salt, and sodium salt.

In a preferred embodiment, the supplement is magnesium salt.

In another aspect, said composition further comprises an effective amount of a compound selected from the group consisting of: rifampicin, disulfiram, and indomethacin, or a pharmaceutically acceptable salt thereof.

In yet another aspect, the invention relates to a composition of matter comprising a combination of (a) a salt of a metal chelator selected from the group consisting of: bathocuproine, bathophenanthroline, DTPA, EDTA, EGTA, penicillamine, TETA, and TPEN, or hydrophobic derivatives thereof, and (b) clioquinol; wherein said salt of the metal chelator is selected from the group consisting of: ammonium, calcium, magnesium, and sodium.

In a preferred embodiment, the metal chelator is bathocuproine. In another preferred embodiment, the salt of said metal chelator is a magnesium salt.

In another aspect, said composition further comprises an effective amount of a compound selected from the group consisting of: rifampicin, disulfiram, and indomethacin, or a pharmaceutically acceptable salt thereof.

In yet another aspect, the invention relates to a composition of matter comprising a combination of (a) an alkalinizing agent and (b) clioquinol.

BRIEF DESCRIPTION OF THE FIGURES

FIG. 2A is a graph showing the proportion of soluble $A\beta_{1-40}$ remaining in the supernatant after incubation with various metal ions. FIG. 2B is a graph showing a turbidometric analysis of pH effect on metal ion-induced $A\beta_{1-40}$ aggregation. FIG. 2C is a graph showing the proportion of soluble $A\beta_{1-40}$ remaining in the supernatant after incubation with various metal ions, where high metal ion concentrations were used.

FIG. 4A is a graph showing the proportion of soluble $A\beta_{1-40}$ remaining in the supernatant following incubation at various pHs in PBS $\pm Zn^{2+}$ or $Cu^{2+}$. FIG. 4B is a graph showing the proportion of soluble $A\beta_{1-40}$ remaining in the supernatant following incubation at various pHs with different $Cu^{2+}$, concentrations. FIG. 4C is a graph showing the relative aggregation of nM concentrations of $A\beta_{1-40}$ at pH 7.4 and 6.6 with different $Cu^{2+}$, concentrations.

FIG. 5A is a graph showing a turbidometric analysis of $Cu^{2+}$-induced $A\beta_{1-40}$ aggregation at pH 7.4 reversed by successive cycles of chelator. FIG. 5B is a graph showing a turbidometric analysis of the reversibility of $Cu^{2+}$-induced $A\beta_{1-40}$ aggregation as the pH cycles between 7.4 and 6.6.

FIGS. 13A and 13B are graphical representations showing $Fe^{3+}$ or $Cu^{2+}$ reduction by $A\beta$ peptides. FIG. 13A illustrates the reducing capacity of $A\beta$ species (10 $\mu$M), compared to Vitamin C and insulin (Sigma) (all 10 $\mu$M) towards $Fe^{3+}$ or $Cu^{2+}$ (10 $\mu$M) in PBS, pH 7.4, after 1 hour co-incubation, 37° C. Data indicate concentration of reduced metal ions generated. FIG. 13B shows the effect of oxygen tension and chelation upon $A\beta_{1-42}$ metal reduction. $A\beta_{1-42}$ was incubated as in FIG. 13A under various buffer gas conditions. "Ambient"=no efforts were made to adjust the gas tension in the bench preparations of the buffer vehicle, "$O_2$"=100% $O_2$ was continuously bubbled through the PBS vehicle for 2 hours (at 20° C.), before the remainder of the incubation components was added, "Ar"=100% Ar was continuously bubbled through the PBS vehicle for 2 hours (at 20° C.), before the remainder of the incubation components was added. "+DFO or TETA"=Desferrioxamine (DFO, Sigma, 200 $\mu$M) was added to the $A\beta_{1-42}$ incubation in the presence of $Fe^{3+}$ 10 $\mu$M, or triethylenetetramine dihydrochloride (TETA, Sigma, 200 $\mu$M) was added to the $A\beta_{1-42}$ incubation in the presence of $Cu^{2+}$ 10 $\mu$M, under ambient oxygen conditions. All data points are means ±SD, n=3.

FIG. 14A shows $H_2O_2$ produced by $A\beta_{1-42}$ (in PBS, pH 7.4, under ambient gas conditions, 1 hour, 37° C.) following co-incubation with various concentrations of catalase in the presence of 1 $\mu$M $Fe^{3+}$. FIG. 14B shows a comparison of $H_2O_2$ generation by variant $A\beta$ species: $A\beta_{1-42}$, $A\beta_{1-40}$, rat $A\beta_{1-40}$, $A\beta_{40-1}$, and $A\beta_{1-28}$ (vehicle conditions as in FIG. 14A). FIG. 14C shows the effect of metal chelators (200 $\mu$M) on $H_2O_2$ production from $A\beta_{1-42}$ when incubated in the presence of $Fe^{3+}$ or $Cu^{2+}$ (1 $\mu$M) (vehicle conditions as in FIG. 14A). BC=Bathocuproinedisulfonate, BP=Bathophenanthroline-disulfonate. The effects of DFO were assessed in the presence of $Fe^{3+}$, and TETA was assessed in the presence of $Cu^{2+}$, as indicated. FIG. 14D shows $H_2O_2$ produced by $A\beta_{1-42}$, $A\beta_{1-40}$, and Vitamin C in the presence of $Fe^{3+}$ (1 $\mu$M) (in PBS, pH 7.4 buffer, 1 hr, 37° C.) under various dissolved gas conditions (described in FIG. 13B): ambient air, $O_2$ enrichment, and anaerobic (Ar) conditions, as indicated. FIG. 14E shows $H_2O_2$ produced by $A\beta_{1-42}$, $A\beta_{1-40}$, and Vitamin C in the presence of $Cu^{2+}$ (1 $\mu$M) (in PBS, pH 7.4 buffer, 1 hr, 37° C.) under various dissolved gas conditions (as in FIG. 14D). All data points are means ±SD, n=3.

FIG. 15A shows the spectrophotometric absorbance at 250 nm (after subtracting buffer blanks) for $A\beta_{1-42}$ (10 $\mu$M, in PBS, pH 7.4, with 1 $\mu$M $Fe^{3+}$, incubated 1 hr, 37° C.) under ambient air (+100 U/mL superoxide dismutase, SOD), $O_2$ enrichment, and anaerobic (Ar) buffer gas conditions (described in FIG. 13B). FIG. 15B shows the spectrophotometric absorbance at 250 nm (after subtracting buffer blanks) for variant $A\beta$ peptides: $A\beta_{1-42}$, $A\beta_{1-40}$, rat $A\beta_{1-40}$, $A\beta_{40-1}$, and $A\beta_{1-28}$ (10 $\mu$M in PBS, pH 7.4, with 1 $\mu$M $Fe^{3+}$, incubated 1 hr, 37° C., under ambient buffer gas conditions). All data points are means ±SD, n=3.

FIG. 16A shows the signal from the TBARS assay of OH• produced from Vitamin C (100 $\mu$M) and variant $A\beta$ species (10 $\mu$M): $A\beta_{1-42}$, $A\beta_{1-40}$, rat $A\beta_{1-40}$, $A\beta_{40-1}$, and $A\beta_{1-28}$ (in PBS, pH 7.4, with 1 $\mu$M $Fe^{3+}$ or $Cu^{2+}$ as indicated, incubated 1 hr, 37° C., under ambient buffer gas conditions). FIG. 16B illustrates the effect of OH•-specific scavengers upon OH• generation by Vitamin C and $A\beta_{1-42}$. Mannitol (5 mM, Sigma) or dimethyl sulfoxide (DMSO, 5 mM, Sigma), was co-incubated with Vitamin C (10 $\mu$M+500 $\mu$M $H_2O_2$) or $A\beta_{1-42}$ (10 $\mu$M) (conditions as for FIG. 16A). All data points are means ±SD, n=3.

FIGS. 19A–19C show that metal chelators promote the solubilization of $A\beta$ from human brain sample homogenates.

FIG. 20B shows a western blot comparing extracted $A\beta$ from an AD brain (AD) to that of sedimentable deposits from healthy brain tissue (young control—C). In the experiments of FIG. 20B, TBS buffer was used rather than PBS.

FIG. 25A shows a western blot of Aβ extracted from brain tissue by various concentrations of clioquinol. FIG. 25B is a graphic representation of solubilization of Aβ by clioquinol.

FIG. 28B shows that Aβ solubility in metal-depleted tissue is restored by supplementing with magnesium.

Upper panel: representative blot from AD specimen.

Lower panel: representative blot from aged non-AD tissue bearing a similar total Aβ load.

Figure 29A:
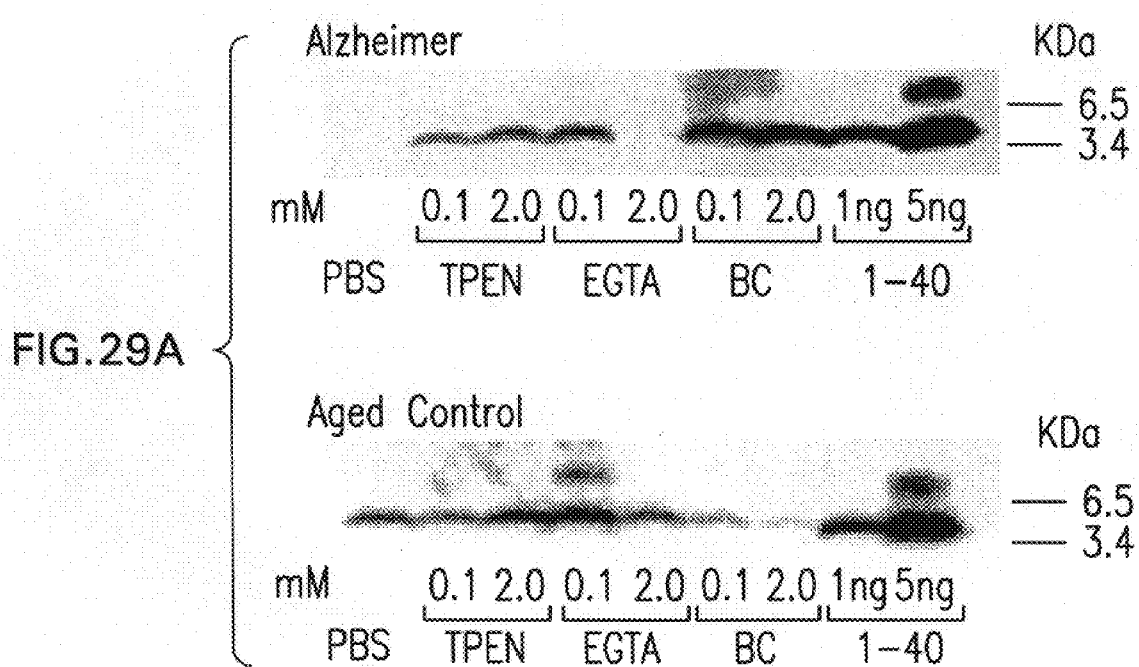
FIGS. 29A and 29B—FIG. 29A shows that patterns of chelator-promoted solubilization of Aβ differ in AD and aged-matched, non-AD tissue.
Figure 29B:
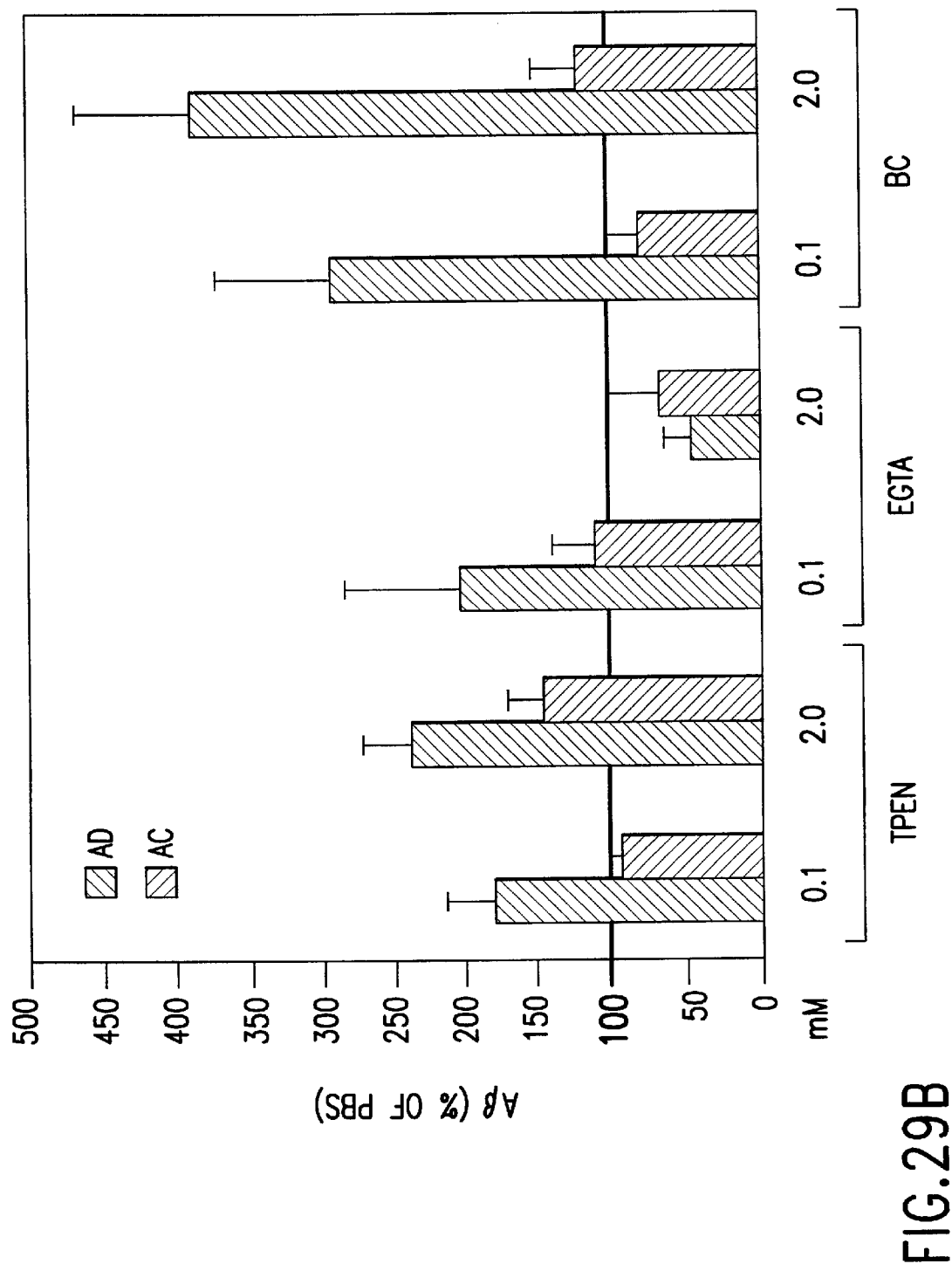

FIG. 29B shows soluble Aβ resulting from chelation treatment for AD and aged-matched, non-AD tissue, expressed as a percentage of the PBS-only treatment group.

Figure 30:
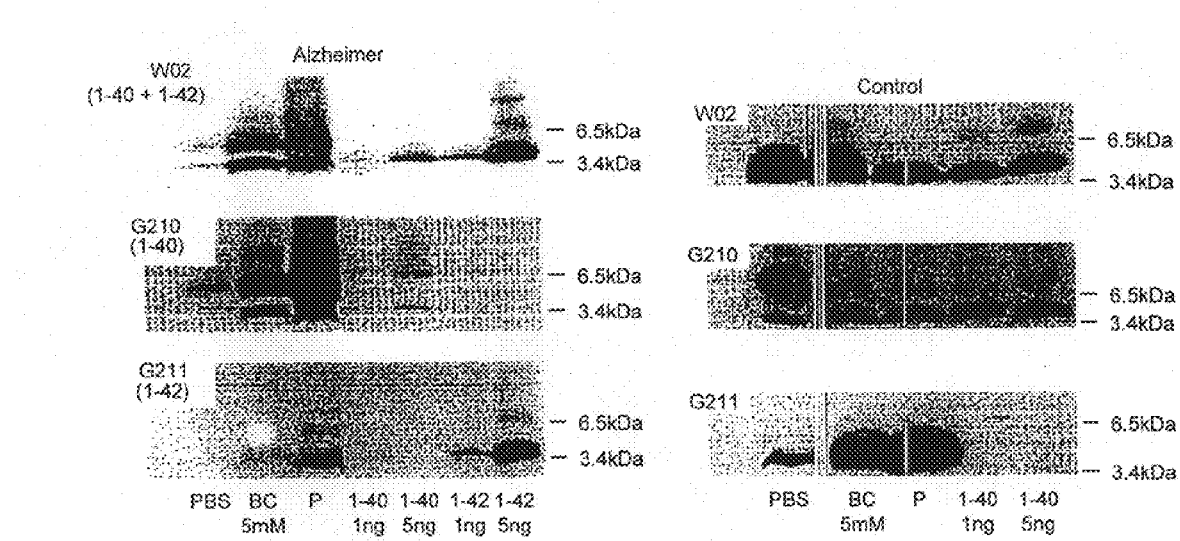

FIG. 30 shows that chelation promotes the solubilization of $A\beta_{1-40}$ and $A\beta_{1-42}$ from AD and non-AD tissue. Representative AD (left panels) and aged-matched control specimens (right panels) were prepared as described in PBS or 5 mM BC. Identical gels were run and Western blots were probed with mAbs WO2 (raised against residues 5–16, recognizes $A\beta_{1-40}$ and $A\beta_{1-42}$), G210 (raised against residues 35–40, recognizes $A\beta_{1-40}$) or G211 (raised against residues 35–42, recognizes $A\beta_{1-42}$) (See Ida, N., et al., *J. Biol. Chem.*, 271:22908 (1996)).

Figure 31A:
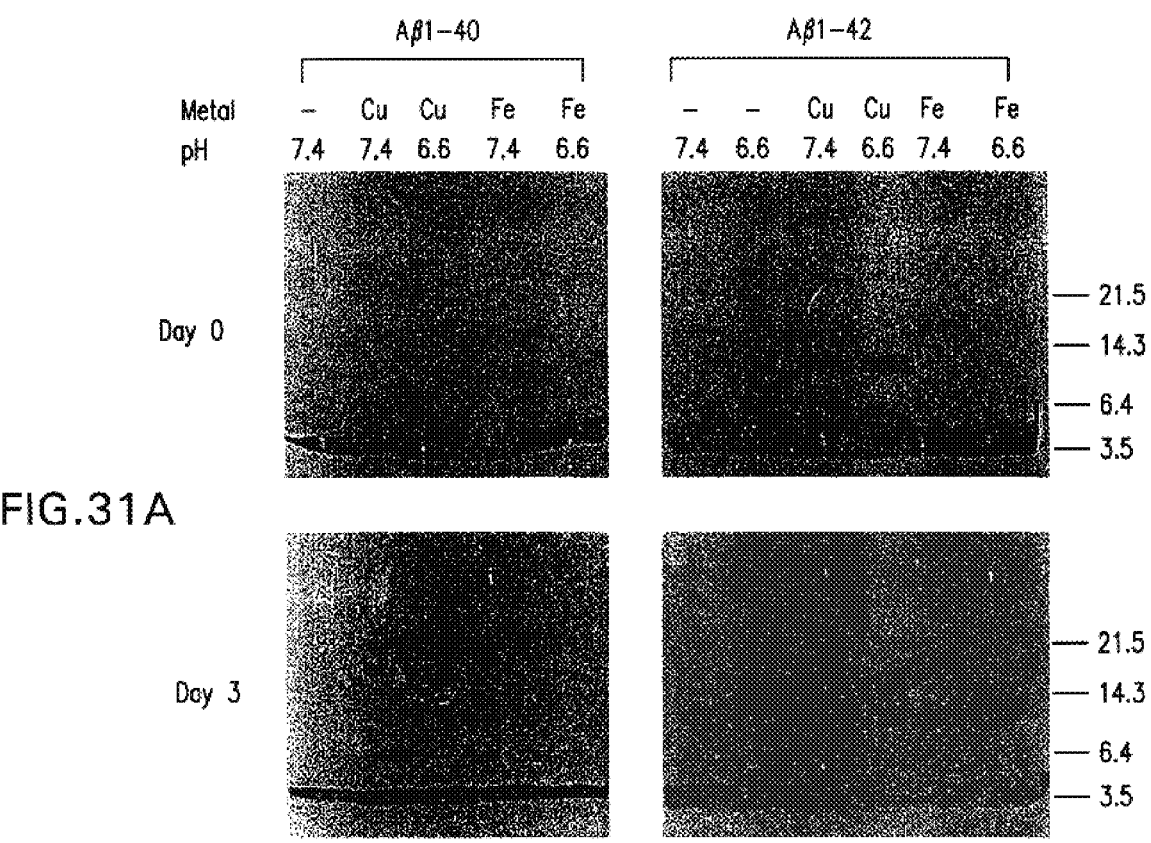
Figure 31B:
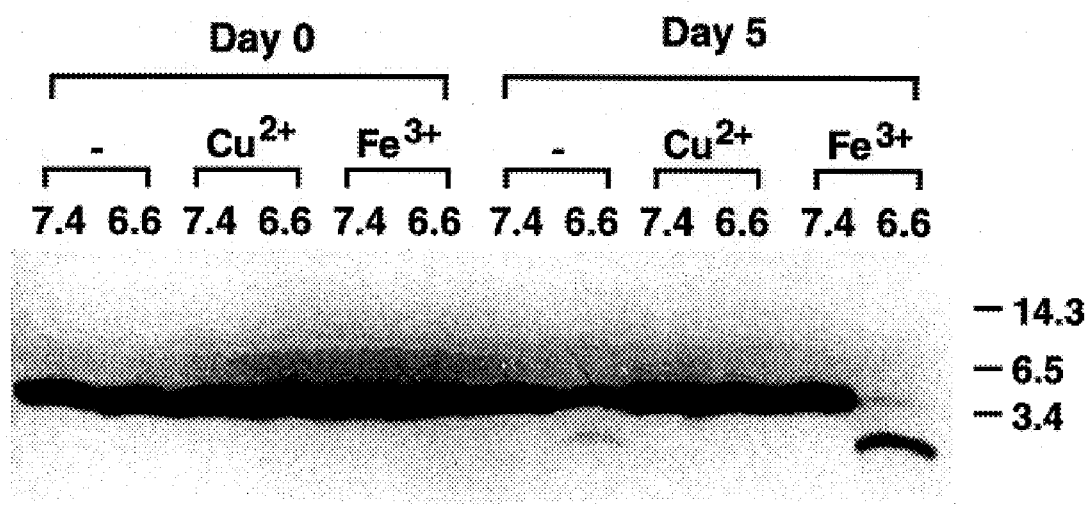

FIGS. 31A and 31B—FIG. 31A shows SDS-resistant polymerization of human $A\beta_{1-40}$ versus human $A\beta_{1-42}$ with $Zn^{2+}$ or $Cu^{2+}$. FIG. 31B shows SDS-resistant polymerization of rat $A\beta_{1-40}$ with $Cu^{2+}$ or $Fe^{3+}$.

Figure 32A:
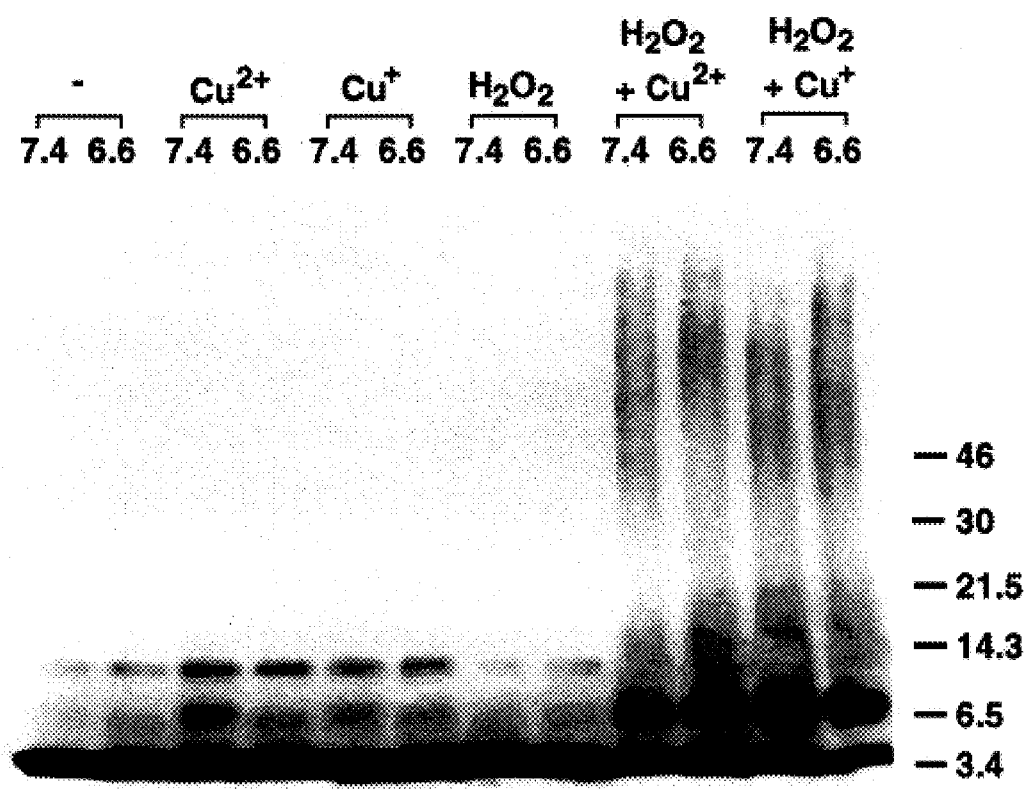
Figure 32B:
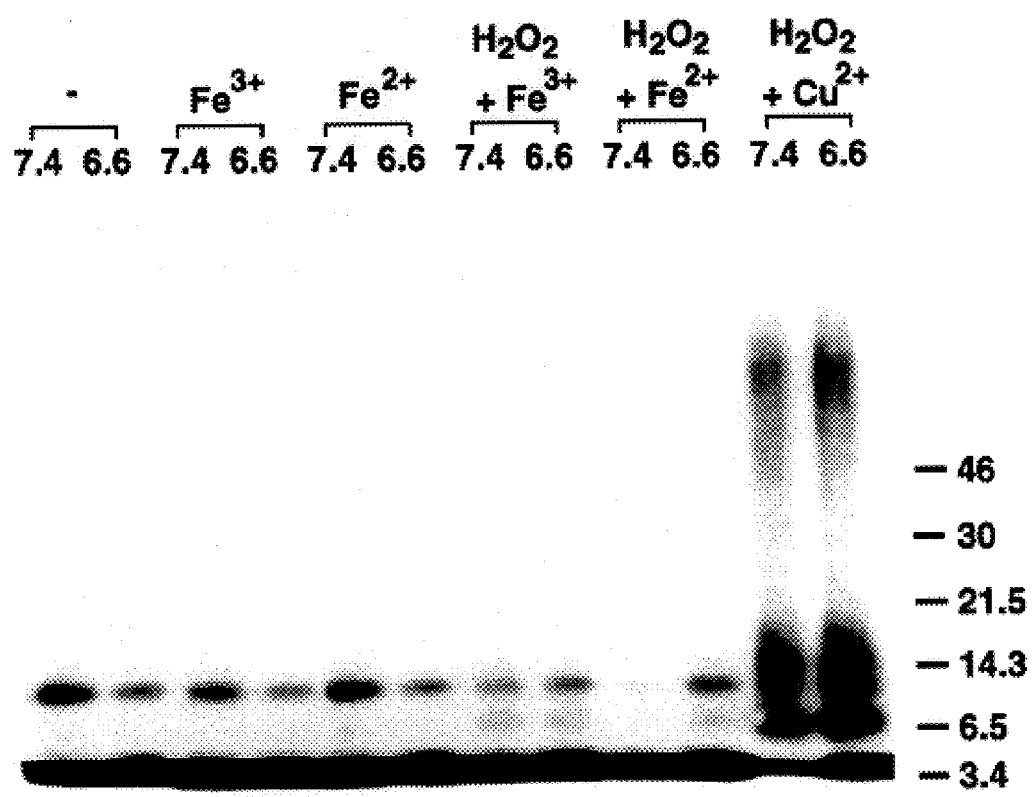
Figure 32C:
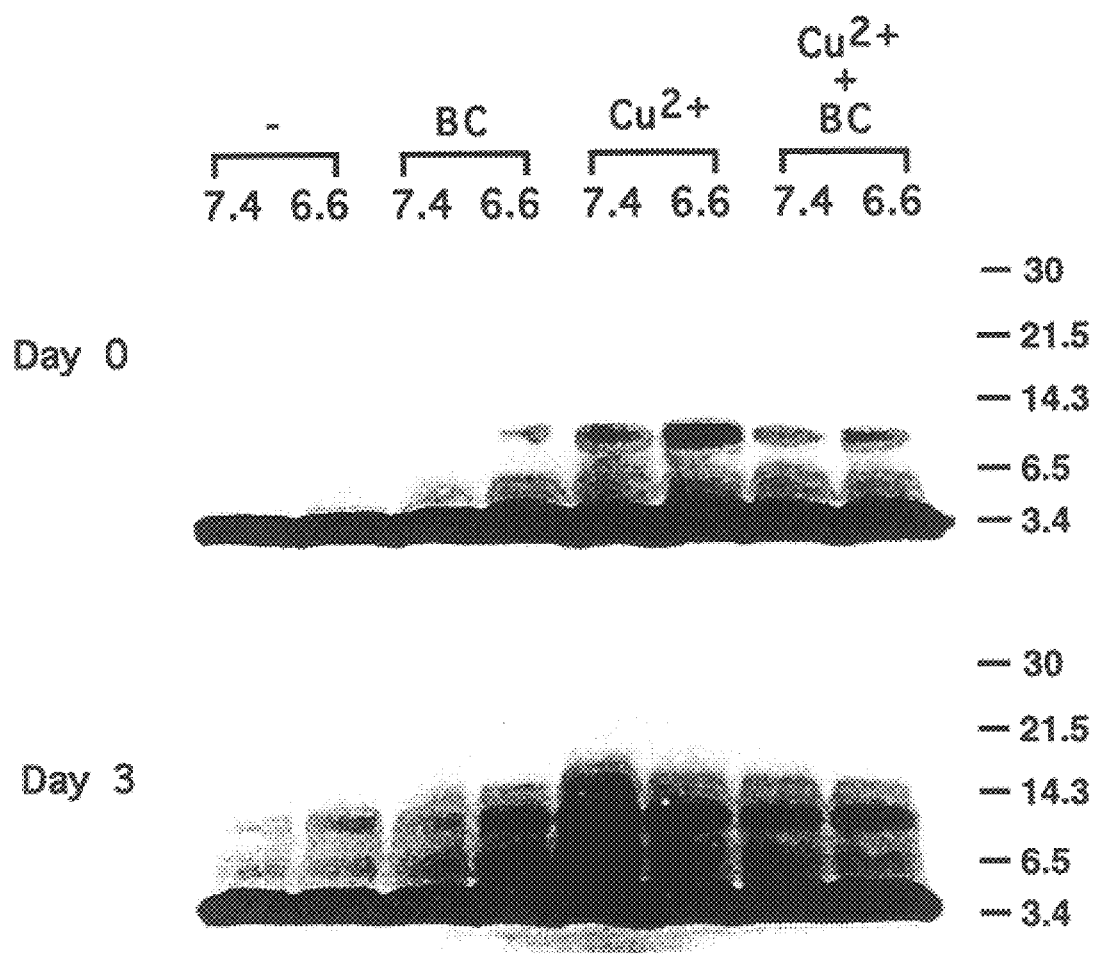

FIGS. 32A–32C—FIG. 32A shows $H_2O_2$/Cu induced SDS-resistant polymerization of $A\beta_{1-42}$ (2.5 μM). FIG. 32B shows $H_2O_2$/Fe induced SDS-resistant polymerization of $A\beta_{1-42}$ (2.5 μM). FIG. 32C shows that BC attenuates SDS-resistant polymerization of $A\beta_{1-42}$ (2.5 μM).

Figure 33A:
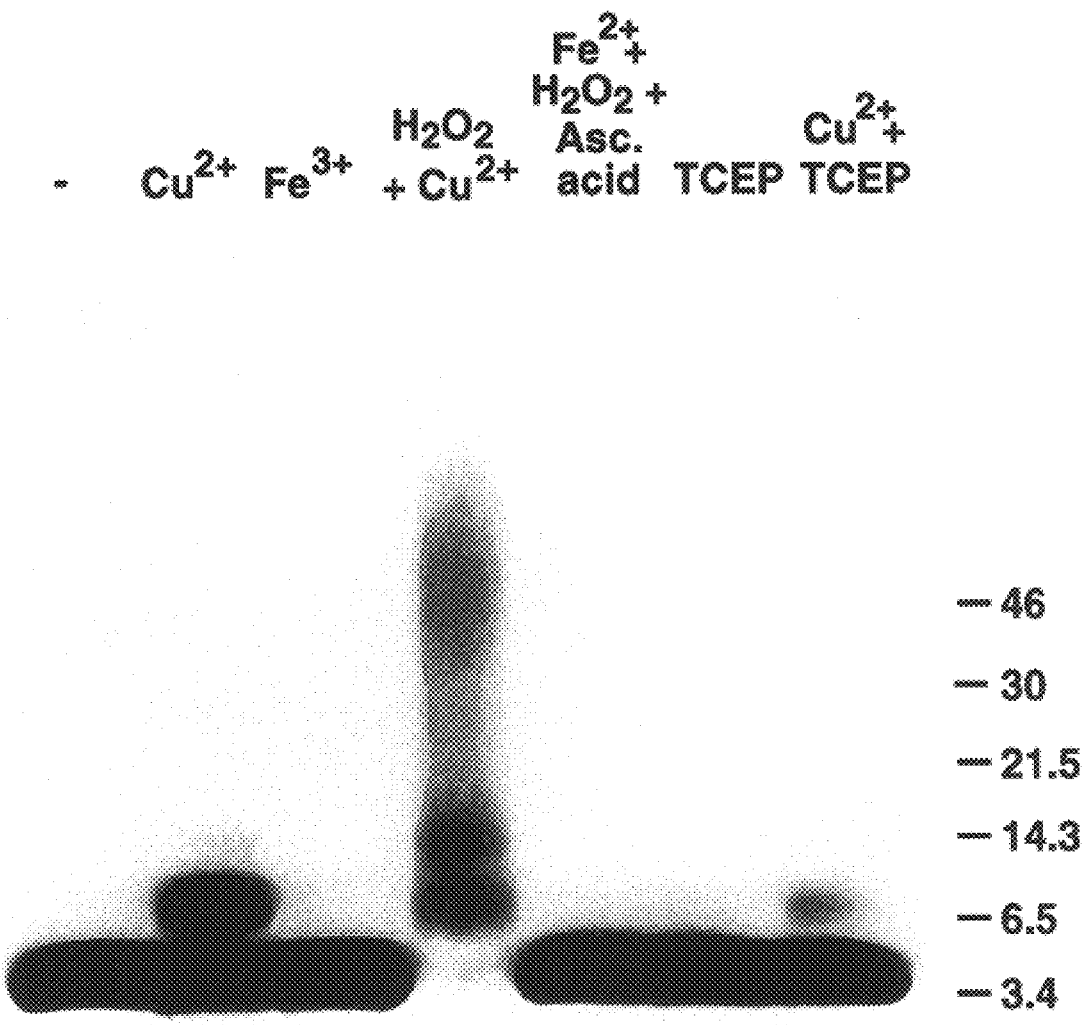
Figure 33B:
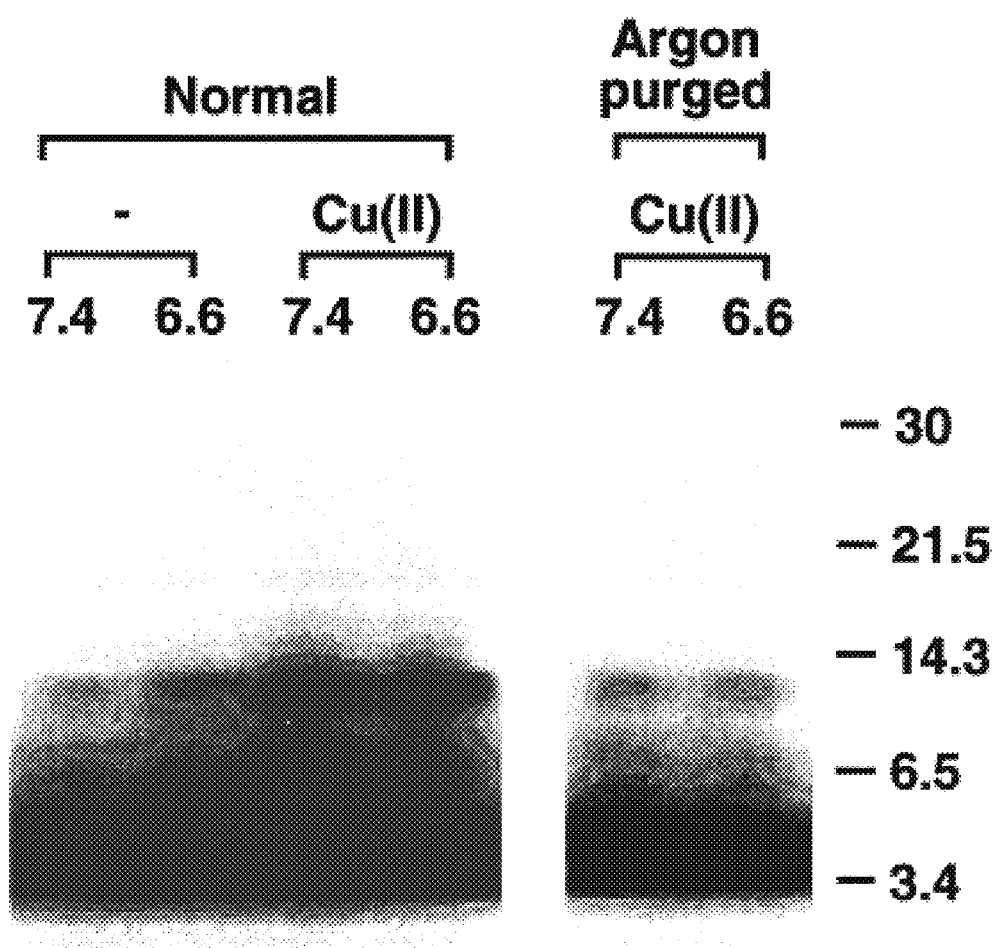

FIGS. 33A and 33B show that $H_2O_2$ generation is required for SDS-resistant polymerization of human $A\beta_{1-42}$ Solution concentrations of metal ion and $H_2O_2$ were 30 μM and 100 μM, respectively. FIG. 33A shows that TCEP (Tris(2-Carboxyethyl)-Phosphine Hydrochloride) attenuates SDS-resistant $A\beta_{1-42}$ polymerization. $A\beta_{1-42}$ (2.5 μM), $H_2O_2$ (100 μM), ascorbic acid (100 μM), TCEP (100 μM). FIG. 33B shows that anoxic conditions prevent SDS-resistant Aβ polymerization. $A\beta_{1-42}$ (2.5 μM) was incubated with no metal or $Cu^{2+}$ at either pH 7.4 or 6.6 and incubated for 60 min. at 25° C. under normal or argon purged conditions. Argon was continuously bubbled through the buffer for 2 h (at 20 ° C.) before the remainder of the incubation components was added.

Figure 34A:
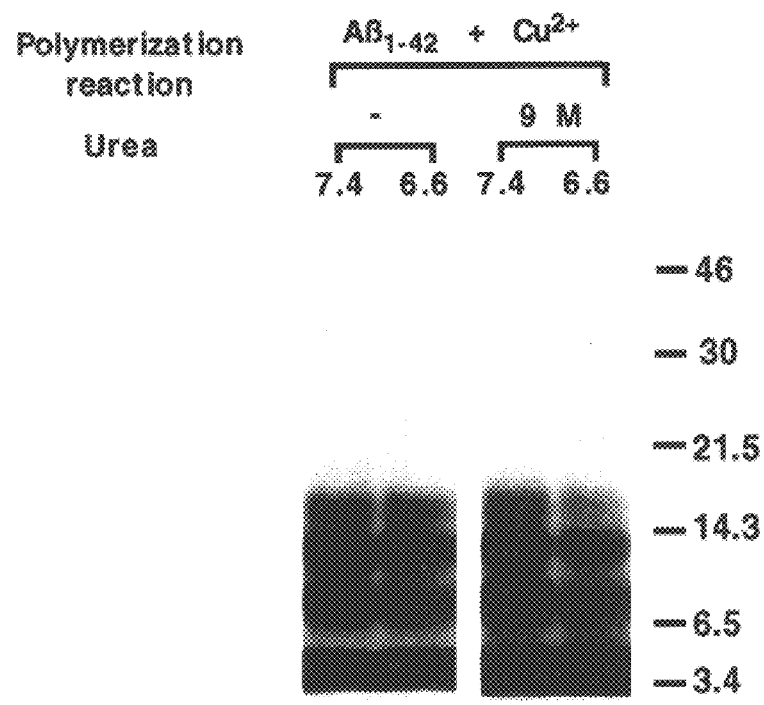
Figure 34A:
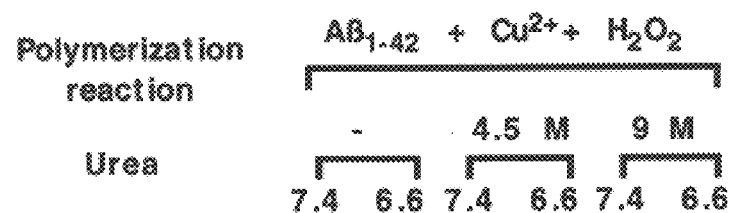
Figure 34B:
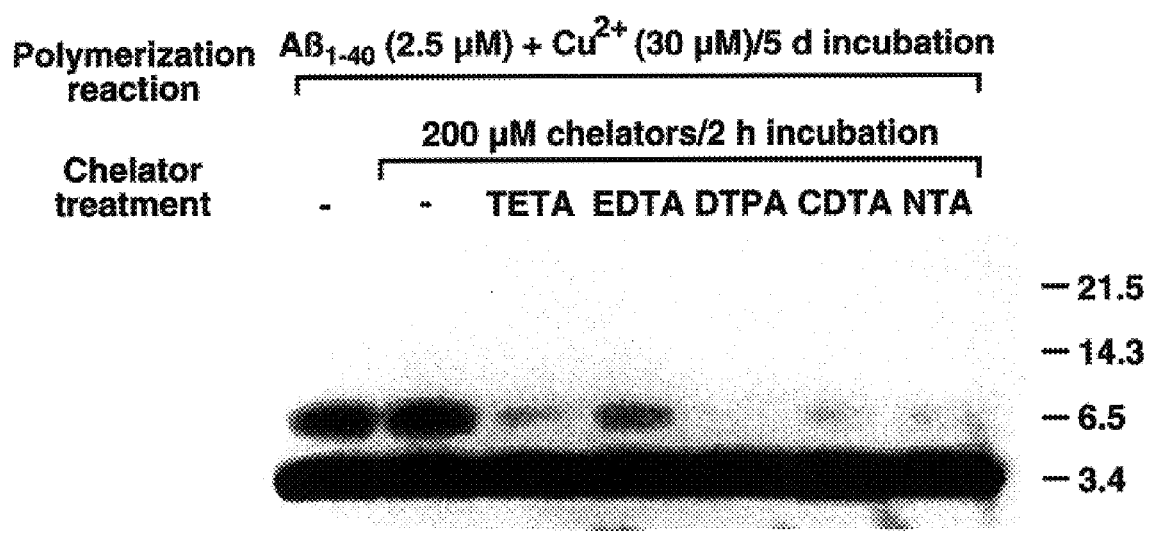
Figure 34C:
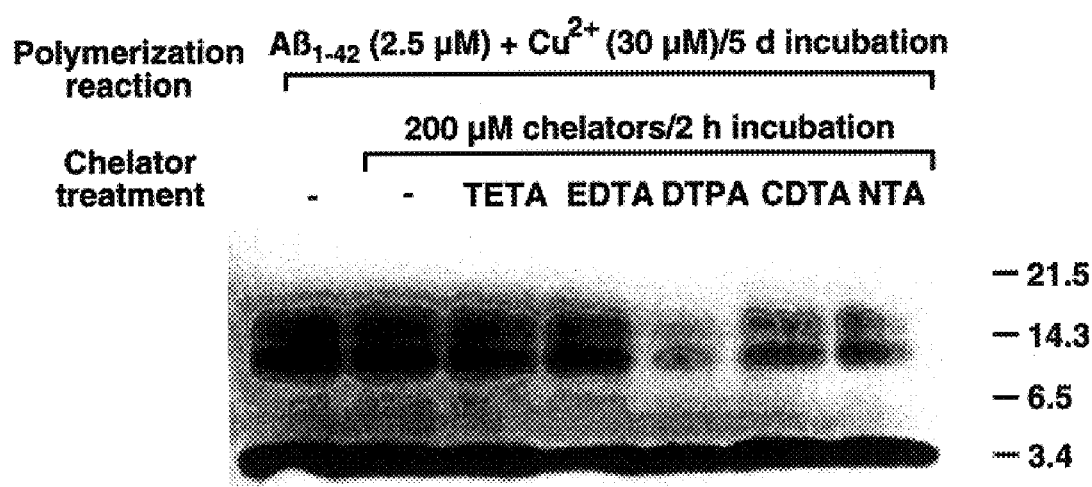
Figure 34D:
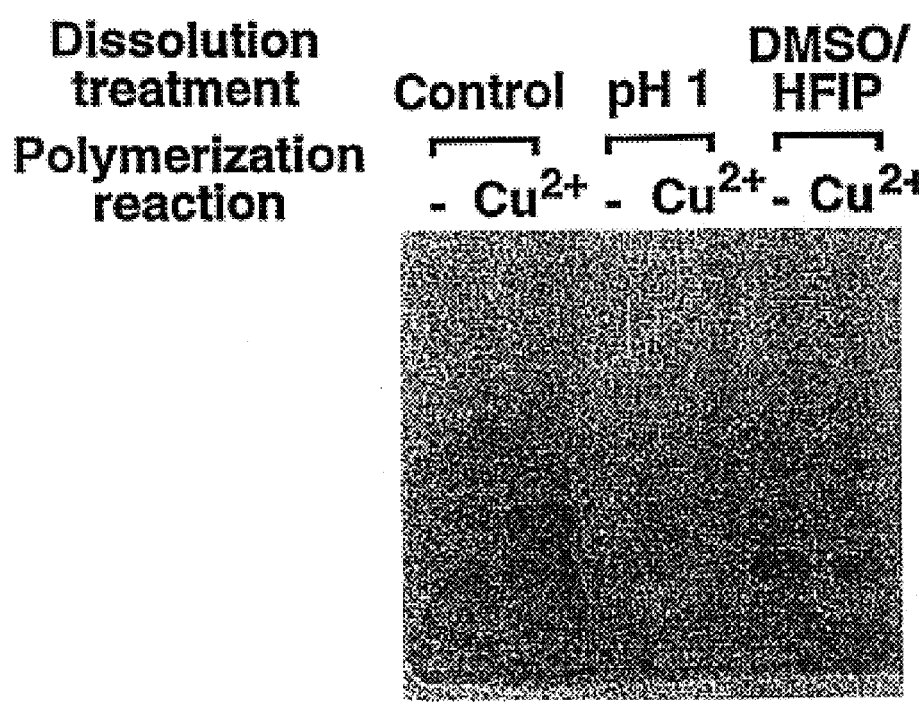
Figure 34E:
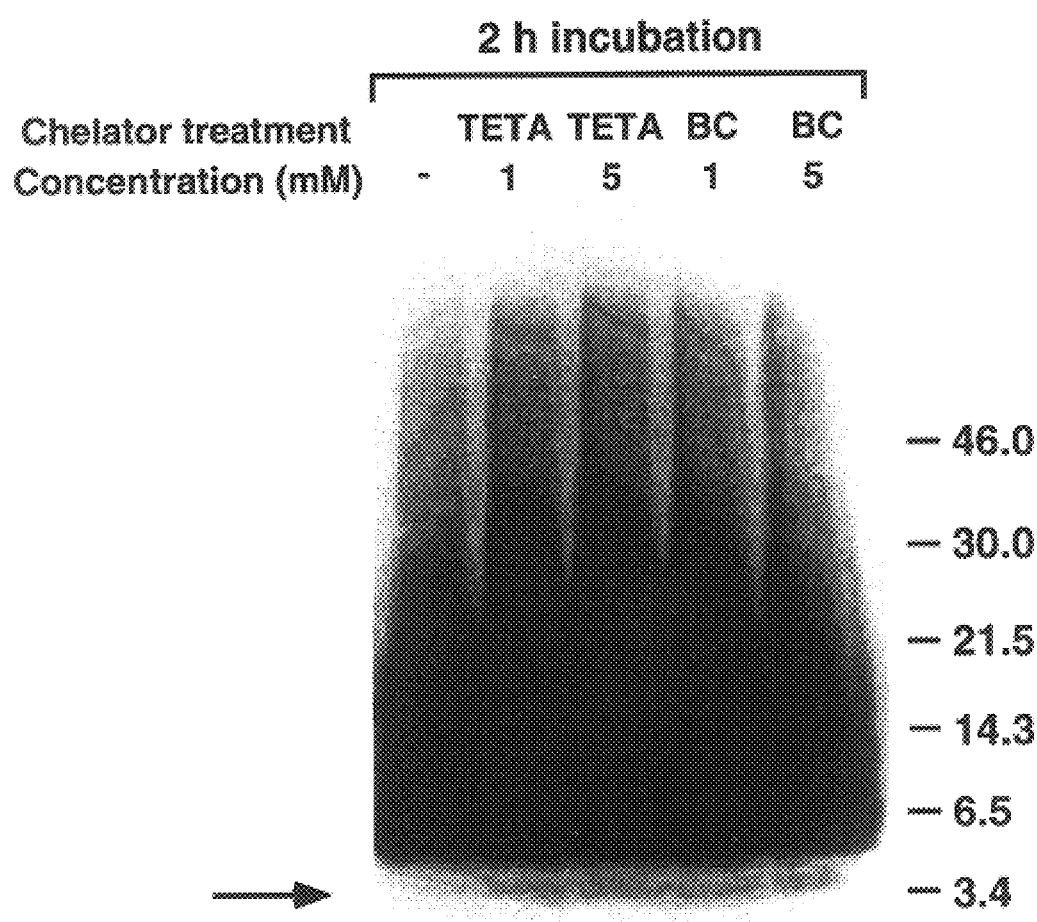

FIGS. 34A–34E show dissolution of SDS-resistant Aβ polymers. FIG. 34A shows that chaotrophic agents are unable to disrupt polymerization. FIG. 34B shows that metal ion chelators disrupt SDS-resistant $A\beta_{1-40}$ polymers. FIG. 34C shows that metal ion chelators disrupt SDS-resistant $A\beta_{1-42}$ polymers. The chelators, their log stability constant, and their molecular weight, respectively, are as follows: TETA (tetraethylenediamine), 20.4, 146; EDTA (ethylenediaminetetra acetic acid), 18.1, 292; DTPA (diethylenetriaminopenta acetic acid), 21.1, 393; CDTA (trans-1,2-diaminocyclohexanetetra acetic acid), 22.0, 346; and NTA (nitrilotriacetic acid), 13.1, 191. FIG. 34D shows that α-helical promoting solvents and low pH disrupt polymers. Aliquots of $A\beta_{1-42}$ were incubated at pH 1 or with DMSO/HFIP (75%:25%) for 2 h (30 min., 37° C). FIG. 34E shows that metal ion chelators disrupt SDS-resistant Aβ polymers extracted from AD brains. Aliquots of SDS-resistant Aβ polymers extracted from AD brains were incubated with no chelator, TETA (1 mM or 5 mM) or BC (1 mM or 5 mM) for 2 h (30 min., 37° C.) and aliquots collected for analysis. Monomer Aβ1-40 is indicated.

DETAILED DESCRIPTION OF THE PREFERRED EMBODIMENTS

Definitions

In the description that follows, a number of terms are utilized extensively. In order to provide a clear and consistent understanding of the specification and claims, including the scope to be given such terms, the following definitions are provided.

Aβ peptide is also known in the art as Aβ, β protein, β-A4 and A4. In the present invention, the Aβ peptide may be comprised of peptides $A\beta_{1-39}$, $A\beta_{1-40}$, $A\beta_{1-41}$, $A\beta_{1-42}$, and $A\beta_{1-43}$. The most preferred embodiment of the invention makes use of $A\beta_{1-40}$. However, any of the Aβ peptides may be employed according to the present invention. Aβ peptides of the invention include $A\beta_{X-39}$, $A\beta_{X-40}$, $A\beta_{X-42}$, and $A\beta_{X-43}$, where X is less than or equal to 17; and $A\beta_{Y-17}$, where Y is less than or equal to 5. The sequence of Aβ peptide is found in Hilbich, C., et al., *J. Mol. Biol.* 228:460–473 (1992).

Amyloid as is commonly known in the art, and as is intended in the present specification, is a form of aggregated protein.

Amyloidosis is any disease characterized by the extracellular accumulation of amyloid in various organs and tissues of the body.

Aβ Amyloid is an aggregated Aβ peptide. It is found in the brains of patients afflicted with AD and DS and may accumulate following head injuries.

Biological fluid means fluid obtained from a person or animal which is produced by said person or animal. Examples of biological fluids include but are not limited to cerebrospinal fluid (CSF), blood, serum, and plasma. In the present invention, biological fluid includes whole or any fraction of such fluids derived by purification by any means, e.g., by ultrafiltration or chromatography.

Copper(II), unless otherwise indicated, means salts of $Cu^{2+}$, i.e., $Cu^{2+}$ in any form, soluble or insoluble.

Copper(I), unless otherwise indicated, means salts of $Cu^+$, i.e., $Cu^+$ in any form, soluble or insoluble.

Metal chelators include metal-binding molecules characterized by two or more polar groups which participate in forming a complex with a metal ion, and are generally well-known in the art for their ability to bind metals competitively.

Physiological solution as used in the present specification means a solution which comprises compounds at physiological pfl, about 7.4, which closely represents a bodily or biological fluid, such as CSF, blood, plasma, et cetera.

Treatment: delay or prevention of onset, slowing down or stopping the progression, aggravation, or deterioration of the symptoms and signs of Alzheimer's disease, as well as amelioration of the symptoms and signs, or curing the disease by reversing the physiological and anatomical damage.

Zinc, unless otherwise indicated, means salts of zinc, i.e., $Zn^{2+}$ in any form, soluble or insoluble.

Methods for Identifying Agents Useful in the Treatment of AD

The aim of the present invention is to clarify both the factors which contribute to the neurotoxicity of Aβ polymers and the mechanism which underlies their formation. These findings can then be used to (i) identify agents that can be used to decrease the neurotoxicity of Aβ, as well as the formation of Aβ polymers, and (ii) utilize such agents to develop methods of preventing, treating or alleviating the symptoms of AD and related disorders.

The present invention relates to the unexpected discovery that Aβ peptides directly produce oxidative stress through the generation of abundant reactive oxygen species (ROS), which include hydroxyl radical (OH•) and hydrogen peroxide ($H_2O_2$). The production of ROS occurs by a metal (Cu, Fe) dependent, pH mediated mechanism, wherein the reduction of $Cu^{2+}$ to $Cu^+$, or $Fe^{3+}$ to $Fe^{2+}$, is catalyzed by Aβ. Aβ is highly efficient at reducing $Cu^{2+}$ and $Fe^{3+}$.

All the redox properties of $A\beta_{1-40}$ (the most abundant form of soluble Aβ) are exaggerated in $A\beta_{1-42}$. Additionally, $A\beta_{1-42}$, but not $A\beta_{1-40}$, recruits $O_2$ into spontaneous generation of another ROS, $O_2^-$, which also occurs in a metal-dependent manner. The exaggerated redox activity of $A\beta_{1-42}$ and its enhanced ability to generate ROS are likely to be the explanation for its neurotoxic properties. Interestingly, the rat homologue of Aβ, which has 3 substitutions that have been shown to attenuate zinc binding and zinc-mediated precipitation, also exhibits less redox activity than its human counterpart. This may explain why the rat is exceptional in that it is the only mammal that does not exhibit amyloid pathology with age. All other mammals analyzed to date possess the human Aβ sequence.

The sequence of ROS generation by Aβ follows the pathway of superoxide-dismutation, which leads to hydrogen peroxide production in a Cu/Fe-dependent manner. After forming $H_2O_2$, the hydroxyl radical (OH•) is rapidly formed by a Fenton reaction with the Fe or Cu that is present, even when these metals are only at trace concentrations. The OH• radical is very reactive and rapidly attacks the Aβ peptide, causing it to polymerize. This is very likely to be the chemical mechanism that causes the SDS-resistant polymerization that is seen in mature plaque amyloid. Importantly, the redox activity of Aβ is not attenuated by precipitation of the peptide, suggesting that, in vivo, amyloid deposits could be capable of generating ROS in situ on an enduring basis. This suggests that the major source of the oxidative stress in an AD-affected brain are amyloid deposits.

Figure 12:
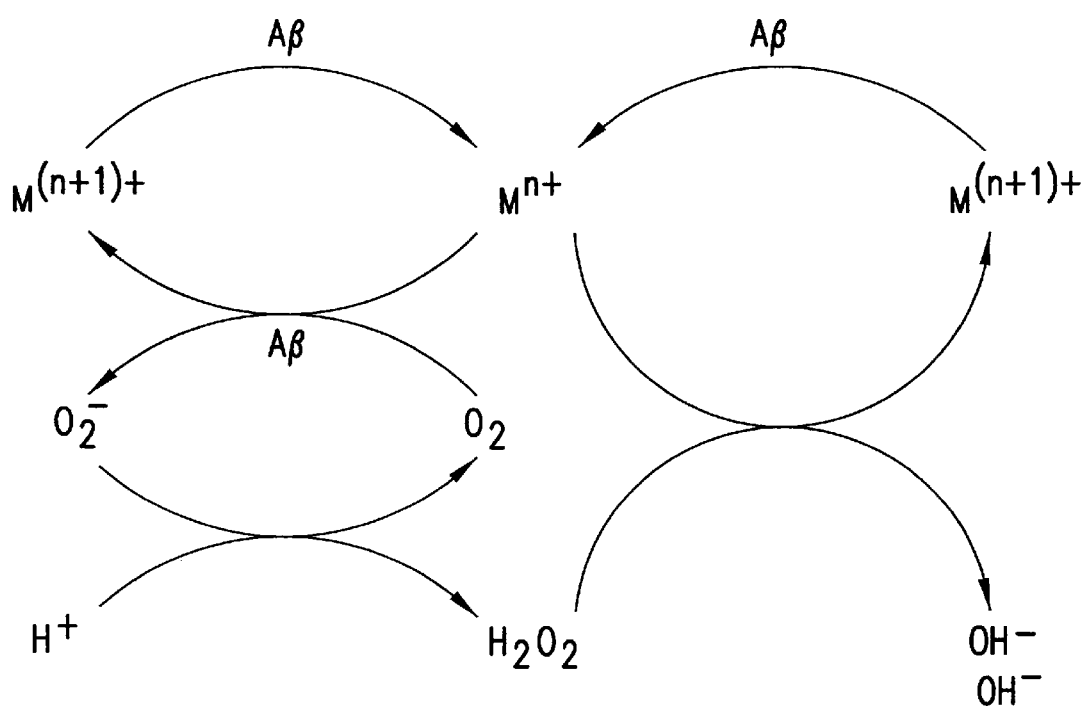
FIG. 12 is a graphical representation showing a model for the generation of reduced metal ions, $O_2^-$, $H_2O_2$, and OH• by $A\beta$ peptides. Note that $A\beta$ facilitates two consecutive steps in the pathway: the reduction of metal ions, and the reaction of $O_2$ with reduced metal ions. The peptide does not appear to be consumed or modified in a one hour time frame by participation in these reactions.

A model for free radical and amyloid formation in AD is shown in FIG. 12. The proposed mechanism is explained as follows:

(1) Soluble and precipitated Aβ species possess superoxide dismutase (SOD)-like activity. Superoxide ($O_2^-$), the substrate for the dismutation, is generated both by spillover from mitochondrial respiratory metabolism, and by $A\beta_{1-42}$ itself. Aβ-mediated dismutation produces hydrogen peroxide ($H_2O_2$)(see FIG. 11), requiring $Cu^{2+}$ or $Fe^{3+}$, which are reduced during the reaction. Since $H^+$ is required for $H_2O_2$ production, an acidotic environment will increase the reaction.

(2) $H_2O_2$ is relatively stable, and freely permeable across cell membranes. Normally, it will be broken down by intercellular catalase or glutathione peroxidase.

(3) In aging and AD, levels of $H_2O_2$ are high, and catalase and peroxidase activities are low. If $H_2O_2$ is not completely catalyzed, it will react with reduced $Cu^+$ and $Fe^{2+}$ in the vicinity of Aβ to generate the highly reactive hydroxyl radical (OH•) by Fenton chemistry.

(4) OH• engenders a non-specific stress and inflammatory response in local tissue. Among the neurochemicals that are released from microglia and possibly neurons in the response are $Zn^{2+}$, $Cu^{2+}$ and soluble Aβ. Familial AD increases the likelihood that $A\beta_{1-42}$ will be released at this point. Local acidosis is also part of the stress/inflammatory response. These factors combine to make Aβ precipitate and accumulate, presumably so that it may function in situ as an SOD, since these factors induce reversible aggregation. Hence, more soluble Aβ species decorate the perimeter of the accumulating plaque deposits.

(5) If Aβ encounters OH•, it will cause covalent cross-linking during the oligomerization process, making it a more difficult accumulation to resolubilize, and leading to the formation of SDS-resistant oligomers characteristic of plaque amyloid.

(6) If $A\beta_{1-42}$ accumulates, it has the property of recruiting $O_2$ as a substrate for the abundant production of $O_2^-$ by a process that is still not understood. Since $O_2$ is abundant in the brain, $A\beta_{1-42}$ is responsible for setting off a vicious cycle in which the accumulation of covalently linked Aβ is a product of the unusual ability of Aβ to reduce $O_2$, and feed an abundant substrate ($O_2^-$) to itself for dismutation, leading to OH• formation. The production of abundant free radicals by the accumulating amyloid may further damage many systems including metal regulatory proteins, thus compounding the problem. This suggests that the major source of the oxidative stress in an AD-affected brain is amyloid deposits.

The metal-dependent chemistry of Aβ-mediated superoxide dismutation is reminiscent of the activity of superoxide dismutase (SOD). Interestingly, mutations of SOD cause amyotrophic lateral sclerosis, another neurodegenerative disorder. SOD is predominantly intracellular, whereas Aβ is constitutively found in the extracellular spaces where it accumulates. Investigation of Aβ by laser flash photolysis confirmed the peptide's SOD-like activity, suggesting that Aβ may be an anti-oxidant under physiological circumstances. Since $H_2O_2$ has been shown to induce the production of Aβ, the accumulation of Aβ in AD may reflect a response to an oxidant stress paradoxically caused by Aβ excess. This may cause and, in turn, be compounded by, damage to the biometal homeostatic mechanisms in the brain environment.

Thus, it has recently been discovered (i) that much of the Aβ aggregate in AD-affected brain is held together by zinc and copper, (ii) that Aβ peptides exhibit Fe/Cu-dependent redox activity similar to that of SOD, (iii) that $A\beta_{1-42}$ is especially redox reactive and has the unusual property of reducing $O_2$ to $O_2^-$, and (iv) that deregulation of Aβ redox reactivity causes the peptide to conveniently polymerize. Since these reactions must be strongly implicated in the pathogenetic events of AD, they offer promising targets for therapeutic drug design.

The discovery that Aβ can generate $H_2O_2$ and $Cu^+$, both of which are associated with neurotoxic effects, offers an explanation for the neurotoxicity of Aβ polymers. These findings suggest that it may be possible to lessen the neurotoxicity of Aβ by controlling factors which alter the concentrations of $Cu^+$ and ROS, including hydrogen peroxide, being generated by accumulated and soluble Aβ. It has been discovered that manipulation of factors such as zinc, copper, and pH can result in altered $Cu^+$ and $H_2O_2$ production by Aβ. Therefore, agents identified as being useful for the adjustment of the pH and levels of zinc and copper of the brain interstitium can be used to adjust the concentration of $Cu^+$ and $H_2O_2$, and can therefore be used to reduce the neurotoxic burden. Such agents will thus be a means of treating Alzheimer's disease.

Agents Useful in the Treatment of AD

A further aspect of the present invention is predicted in part on the elucidation of mechanisms of neurotoxicity in the brain in AD subjects. One mechanism involves a novel $O_2^-$ and biometal-dependent pathway of free radical generation by Aβ peptides. The radicals of this aspect of the present invention may comprise reactive oxygen species (ROS) such as but not limited to $O_2^-$ and OH as well as radicalized Aβ peptides. It is proposed, according to the present invention, that by interfering in the radical generating pathway, the neurotoxicity of the Aβ peptides is reduced.

Accordingly, one aspect of the present invention contemplates a method for treating Alzheimer's disease (AD) in a subject, said method comprising administering to said subject an effective amount of an agent which is capable of inhibiting or otherwise reducing metal-mediated production of free radicals.

The preferred agents according to this aspect are metal chelators, metal complexing compounds, antioxidants and compounds capable of reducing radical formation of Aβ peptides or mediated by Aβ peptides. Particularly preferred metal chelators and metal complexors are capable of interacting with metals (M) having either a reduced charge state $M^{n+}$ or an oxidized state of $M^{(n+1)+}$. Even more particularly, M is Fe and/or Cu.

It is proposed that interactions of Aβ with Fe and Cu are of significance to the genesis of the oxidation insults that are observed in the AD-affected brain. This is due to redox-active metal ions being concentrated in brain neurons and participating in the generation of ROS or other radicals by transferring electrons in their reduced state and described in the following reactions:
Reduced Fe/Cu reacts with molecular oxygen to generate the superoxide anion.

$$M^{n+}+O_2\rightarrow M^{(n+1)+}+O_2^-\qquad\text{Reaction (1)}$$

The $O_2^-$ generated undergoes dismutation to $H_2O_2$ either catalyzed by SOD or spontaneously.

$$O_2^-+O_2^-+2H^+\rightarrow H_2O_2+O_2\qquad\text{Reaction (2)}$$

The reaction of reduced metals with $H_2O_2$ generates the highly reactive hydroxyl radical by the Fenton reaction.

$$M^{n+}+H_2O_2\rightarrow M^{(n+1)+}+OH+OH^-\qquad\text{Reaction (3)}$$

Additionally, the Haber-Weiss reaction can form OH in a reaction catalyzed by $M^{(n+1)+}/M^{n+}$ (Miller et al., 1990).

$$O_2^-+H_2O_2\rightarrow OH+OH^-+O_2\qquad\text{Reaction (4)}$$

Still more preferably, the agent comprises one or more of bathocuproine and/or bathophenanthroline or compounds related thereto at the structural and/or functional levels. Reference to compounds such as bathocuproine and bathophenanthroline include functional derivatives, homologues and analogues thereof.

Accordingly, another aspect of the present invention provides a method for treating AD in a subject said method comprising administering to said subject an effective amount of an agent comprising at least one metal chelator and/or metal complexing compound for a time and under conditions sufficient to inhibit or otherwise reduce metal-mediated production of free radicals.

In one aspect, the free radicals are reactive oxygen species such as $O_2^-$ or OH•. In another aspect, the free radicals include forms of Aβ. However, in a broader sense, it has been found that the metal-mediated Aβ reactions in the brain of AD patients results in the generation of reduced metals and hydrogen peroxide, as well as superoxide and hydroxyl radicals. Furthermore, formation of any other radical or reactive oxygen species by interaction of any of these products with any other metabolic substrate (e.g., superoxide+nitric acid=peroxynitrite) contributes to the pathology observed in AD and Down's syndrome patients. $Cu^{2+}$ reaction with Aβ generates $Cu^+$, Aβ•, $O_2^-$, $H_2O_2$, and OH•, all of which not only directly damage the cells, but also react with biochemical substrates like nitric oxide.

Yet a further aspect of the present invention is directed to a method for treating AD in a subject, said method comprising administering to said subject an effective amount of an agent, said agent comprising a metal chelator, metal complexing compound or a compound capable of interfering with metal mediated free radical formation mediated by Aβ peptides for a time and under conditions sufficient to inhibit or otherwise reduce production of radicals.

The preferred metals according to these aspects of the present invention include Cu and Fe and their various oxidation states. Most preferred are reduced forms of copper ($Cu^+$) and iron ($Fe^+$).

Another mechanism elucidated in accordance with the present invention concerns the formation of aggregates of Aβ, as in conditions involving amyloidosis. In a preferred embodiment, the aggregates are those of amyloid plaques occurring in the brains of AD-affected subjects.

The aggregates according to this aspect of the present invention are non-fibrillary and fibrillary aggregates and are held together by the presence of a metal such as zinc and copper. A method of treatment involves resolubilizing these Aβ aggregates.

The data indicate that Zn-induced $Aβ_{1-40}$ aggregation is completely reversible in the presence of divalent metal ion chelating agents. This suggests that zinc binding may be a reversible, normal function of Aβ and implicates other neurochemical mechanisms in the formation of amyloid. A process involving irreversible Aβ aggregation, such as the polymerization of Aβ monomers, in the formation of polymeric species of Aβ that are present in amyloid plaques is thus a more plausible explanation for the formation of neurotoxic polymeric Aβ species.

According to this aspect of the present invention, there is provided a method of treating AD in a subject comprising administering to said subject an agent capable of promoting, inducing or otherwise facilitating resolubilization of amyloid deposits for a time and under conditions to effect said treatment.

With respect to this aspect of the present invention, it is proposed that a metal chelator or metal complexing agent be administered. Aβ deposits which are composed of fibrillary and non-fibrillary aggregates may be resolubilized by the metal chelating or metal complexing agents, according to this aspect. While fibrile aggregations per se, may not be fully disassociated by administration of such agents, overall deposit resolubilization approaches 70%.

In addition, the agent of this aspect of the present invention may comprise a metal chelator or metal complexing agent alone or in combination with another active ingredient such as but not limited to rifampicin, disulfiram, indomethacin or related compounds. Preferred metal chelators are DTPA, bathocuproine, bathophenanthroline, and penicillamine or related compounds.

A "related" compound according to these and other aspects of the present invention are compounds related to the levels of structure or function and include derivatives, homologues and analogues thereof.

Accordingly, the present invention contemplates compositions such as pharmaceutical compositions comprising an active agent and one or more pharmaceutically, acceptable carriers and/or diluents. The active agent may be a single compound such as a metal chelator or metal complexing agent or may be a combination of compounds such as a metal chelating or complexing compound and another compound. Preferred active agents include, for reducing radical formation, bathocuproine and/or bathophenanthroline; and for promoting resolubilization, DTPA, bathocuproine, bathophenanthroline, and penicillamine or derivatives, homologues or analogues thereof, or any combination thereof.

Further, it has been found that the agents of the present invention may be administered along with the compound clioquinol. Clioquinol has been shown to be particularly effective in resolubilizing A$\beta$ aggregates in combination with other chelators. Most preferably clioquinol is administered in combination with bathocuproine.

It has also been found that there is a clioquinol concentration "window" within which the A$\beta$ aggregates are dissolved. Increasing the concentration of clioquinol above the optimal window concentration not only is toxic to the patient but also sharply drops the dissolution effect of clioquinol on the A$\beta$ amyloid. Similarly, amounts below that of the window are too small to result in any dissolution.

Therefore, for each given patient, the attending physician need be mindful of the window effect and attend to varying the dosages of clioquinol so that during the course of administration, clioquinol concentrations would be varied frequently to randomly allow achieving the most effective concentration for dissolving A$\beta$ amyloid deposits in the given patient.

It is, therefore, desired that the plasma levels of clioquinol not be steady state, but be kept fluctuating between 0.01 $\mu$M, but not greater than 2 $\mu$M. Since the drug is absorbed to reach peak plasma levels within 30 minutes of oral ingestion, and since the excretion half life is about 1–3 hours, the best way to dose the patient is with oral doses no more often than every three hours, preferably every six hours or eight hours, but as infrequently as once every day or once every two days are expected to be therapeutic.

An oral dose of 200 mg/kg achieves 5 $\mu$M plasma levels in rats, and 10–30 $\mu$M in dogs. An oral dose of 500 mg/kg achieves 20–70 $\mu$M in monkeys. The drug is freely permeable into the brain and is rapidly excreted.

Therefore, in humans, it is expected that a plasma level of 0.5 $\mu$M would be achieved within 30 minutes of ingesting 10 mg/kg body weight. In a 70 kg person this is 700 mg of clioquinol. Therefore, a dose of 700 mg four times a day (2800 mg/day) would be therapeutic.

However, sustained treatment with doses of clioquinol at a dose as low as 10 mg/kg/day causes the neurological side effect, subacute myelo-optic neuritis. Therefore, dosage that high is undesirable. This is equivalent to 700 mg/day. The side effect is believed to be due to loss of vitamin B12. Therefore, co-therapy with vitamin B12 100 $\mu$M/day orally or, preferably, 1000 $\mu$M/month intramuscularly, is to be administered with clioquinol treatment to abolish this side effect.

To minimize the chances of this side effect, a lower dose of clioquinol can also be used—100 mg, three or four times a day would achieve peak plasma levels of about 0.1 $\mu$M, and is likely to be therapeutic without putting the patient at risk for neurological side effects. Nevertheless, co-administration of Vitamin B12 should be mandatory.

For the treatment of moderately affected or severely affected patients, where risking the neurological side effects is less of a concern since the quality of their life is very poor, the patient may be put on a program of treatment (after informed consent) consisting of high dose clioquinol for 1 to 21 days, but preferably no more than 14 days, followed by a period of low dose therapy for seven days to three months. A convenient schedule would be two weeks of high dose therapy followed by two weeks of low dose therapy, oscillating between high and low dose periods for up to 12 months. If after 12 months the patient has made no clinical gains on high/low clioquinol therapy, the treatment should be discontinued. All regimens would be accompanied by Vitamin B 12 co-therapy.

Another typical case would be the treatment of a mildly affected individual. Such a patient would be treated with low dose clioquinol for up to 12 months. If after 6 months no clinical gains have been made, the patient could then be placed on the high/low alternation regimen for up to another 12 months.

Particular concentrations and modes of therapy will vary depending on the particular clioquinol-containing combination administered.

Accordingly, the present invention contemplates compositions such as pharmaceutical compositions comprising an active agent and one or more pharmaceutically, acceptable carriers and/or diluents. The active agent may be clioquinol or a combination of clioquinol and another metal chelating compound.

The pharmaceutical forms containing the active agents may be administered in any convenient manner either orally or parenteraly such as by intravenous, intraperitoneal, subcutaneous, rectal, implant, transdermal, slow release, intrabuccal, intracerebral or intranasal administration. Generally, the active agents need to pass the blood brain barrier and may have to be chemically modified, e.g. made hydrophobic, to facilitate this or be administered directly to the brain or via other suitable routes. For injectable use, sterile aqueous solutions (where water soluble) are generally used or alternatively sterile powders for the extemporaneous preparation of sterile injectable solutions may be used. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active agents in the required amount in the appropriate solvent with various of the other ingredients enumerated above, as required, followed by sterilization by, for example, filtration or irradiation. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof. Preferred compositions or preparations according to the present invention are prepared so that an injectable dosage unit contains between about 0.25 μg and 500 mg of active compound.

When the active agents are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 1.0 μg and 2000 mg of active compound.

The tablets, troches, pills, capsules and the like may also contain other components such as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional medium or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 μg to about 2000 mg. Alternatively, amounts ranging from 200 ng/kg/body weight to above 10 mg/kg/body weight may be administered. The amounts may be for individual active agents or for the combined total of active agents.

Compositions of the present invention include all compositions wherein the compounds of the present invention are contained in an amount which is effective to achieve their intended purpose. They may be administered by any means that achieve their intended purpose. The dosage administered will depend on the age, health, and weight of the recipient, kind of concurrent treatment, if any, frequency of the treatment, and the nature of the effect desired. The dosage of the various compositions can be modified by comparing the relative in vivo potencies of the drugs and the bioavailability using no more than routine experimentation.

The pharmaceutical compositions of the invention may be administered to any animal which may experience the beneficial effects of the compounds of the invention. Foremost among such animals are mammals, e.g. humans, although the invention is not intended to be so limited.

The following examples are provided by way of illustration to further describe certain preferred embodiments of the invention, and are not intended to be limiting of the present invention, unless specified.

EXAMPLES

Example 1

Copper-Induced, pH Dependent Aggregation of Aβ
Materials and Methods
a) Preparation of Aβ Stock Human Aβ peptide was synthesized, purified and characterized by HPLC analysis, amino acid analysis and mass spectroscopy by W. M. Keck Foundation Biotechnology Resource Laboratory (Yale University, New Haven, Conn.). Synthetic Aβ peptide solutions were dissolved in trifluoroethanol (30% in Milli-Q water (Millipore Corporation, Milford, Mass.)) or 20 mM HEPES (pH 8.5) at a concentration of 0.5–1.0 g/ml, centrifuged for 20 min. at 10,000 g and the supernatant (stock Aβ) used for subsequent aggregation assays on the day of the experiment. The concentration of stock Aβ was determined by UV spectroscopy at 214 nm or by Micro BCA protein assay (Pierce, Rockford, Ill.). The Micro BCA assay was performed by adding 10 μl of stock Aβ (or bovine serum albumin standard) to 140 μl of distilled water, and then adding an equal volume of supernatant (150μl) to a 96-well plate and measuring the absorbance at 562 nm. The concentration of Aβ was determined from the BSA standard curve. Prior to use all buffers and stock solutions of metal ions were filtered though a 0.22 μm filter (Gelan Sciences, Ann Arbor, Mich.) to remove any particulate matter. All metal ions were the chloride salt, except lead nitrate.

b) Aggregation Assays

Aβ stock was diluted to 2.5 μM in 150 mM NaCl and 20 mM glycine (pH 3–4.5), MES (pH 5–6.2) or HEPES (pH 6.4–8.8), with or without metal ions, incubated (30 min., 37° C.), centrifuged (20 min., 10 000 g). The amount of protein in the supernatant was determined by the Micro BCA protein assay as described above.

c) Turbilometric Assays

Turbidity measurements were performed as described by Huang, X., et al., *J. Biol. Chem.* 272:26464–26470 (1997), except Aβ stock was brought to 10 μM (300 μl) in 20 mM HEPES buffer, 150 mM NaCl (pH 6.6, 6.8 or 7.4) with or without metal ions prior to incubation (30 min., 37° C.). To investigate the pH reversibility of $Cu^{2+}$-induced Aβ aggregation, 25 μM $Aβ_{1-40}$ and 25 μM $Cu^{2+}$ were mixed in 67 mM phosphate buffer, 150 mM NaCl (pH 7.4) and turbidity measurements were taken at four 1 min. intervals. Subsequently, 20 μl aliquots of 10 mM EDTA or 10 mM $Cu^{2+}$ were added into the wells alternatively, and, following a 2 min. delay, a further four readings were taken at 1 min. intervals. After the final EDIA addition and turbidity reading, the mixtures were incubated for an additional 30 min. before taking final readings. To investigate the reversibility of pH mediated $Cu^{2+}$-induced $Aβ_{1-40}$ aggregation,10 μM Aβ and 30 μM $Cu^{2+}$ were mixed in 67 mM phosphate buffer, 150 mM NaCl (pH 7.4) and an initial turbidity measurement taken. Subsequently, the pH of the solution was successively decreased to 6.6 and then increased back to 7.5. The pH of the reaction was monitored with a microprobe (Lazar Research Laboratories Inc., Los Angeles, Calif.) and the turbidity read at 5 min. intervals for up to 30 min. This cycle was repeated three times.

d) Inntunofiltration Detection of Low Concentrations of $Aβ_{1-40}$Aggregate

Physiological concentrations of Aβ (8 nM) were brought to 150 mM NaCl, 20 mM HEPES (pH 6.6 or 7.4), 100 nM BSA with $CuCl_2$ (0, 0.1, 0.2, 0.5 and 2 μM) and incubated (30 min., 37° C.). The reaction mixtures (200 μl) were then placed into the 96-well Easy-Titer ELIFA system (Pierce, Rockford, Ill.) and filtered through a 0.22 μm cellulose acetate filter (MSI, Westboro, Mass.). Aggregated particles were fixed to the membrane (0.1% glutaraldehyde, 15 min.), washed thoroughly and then probed with the anti-Aβ mAB 6E10 (Senetek, Maryland Leights, Mich.). Blots were washed and exposed to film in the presence of ECl chemiluminescence reagents (Amersham, Buckinghamshire, England). Immunoreactivity was quantified by transmittance analysis of ECL film from the immunoblots.

e) Aβ Metal-capture ELISA

Aβ (1.5 ng/well) was incubated (37° C., 2 hr) in the wells of $Cu^{2+}$ coated microtiter plates (Xenopore, Hawthorne, N.J.) with increasing concentrations of $Cu^{2+}$ (1–100 nM). Remaining ligand binding sites on well surfaces were blocked with 2% gelatin in tris-buffered saline (TBS) (3 hr at 37° C.) prior to overnight incubation at room temperature with the anti-Aβ mAb 6E10 (Senetek, Maryland Heights, Mich.). Anti-mouse IgG coupled to horseradish peroxidase was then added to each well and incubated for 3 hr at 37° C. Bound antibodies were detected by a 30 minute incubation with stable peroxidase substrate buffer/3,3',5,5'-Tetramethyl benzidine (SPSB/TMB) buffer, followed by the addition of 2 M sulfuric acid and measurement of the increase in absorbance at 450 nm.

f) Extraction of Aβfrom Post-mortem Brain Tissue

Figure 8:
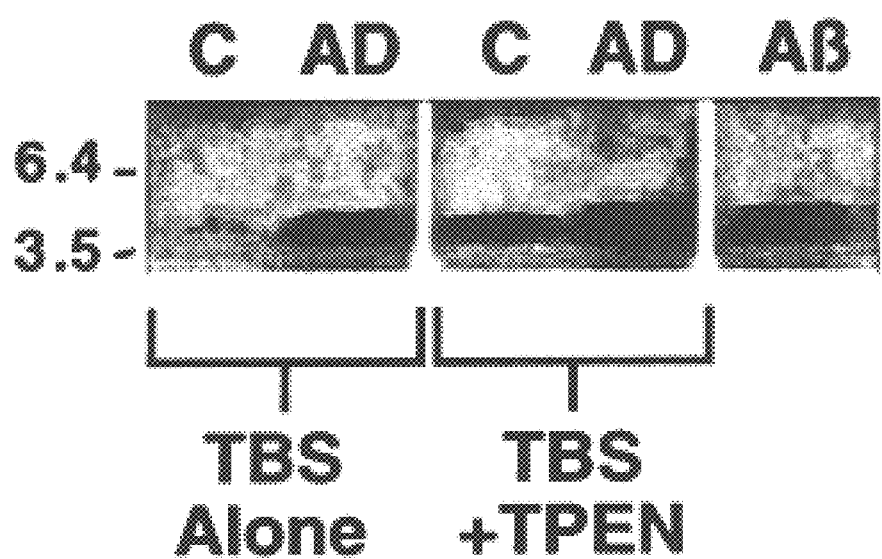
FIG. 8 is a western blot showing the extraction of $A\beta$ from post-mortem brain tissue.
Figure 9:
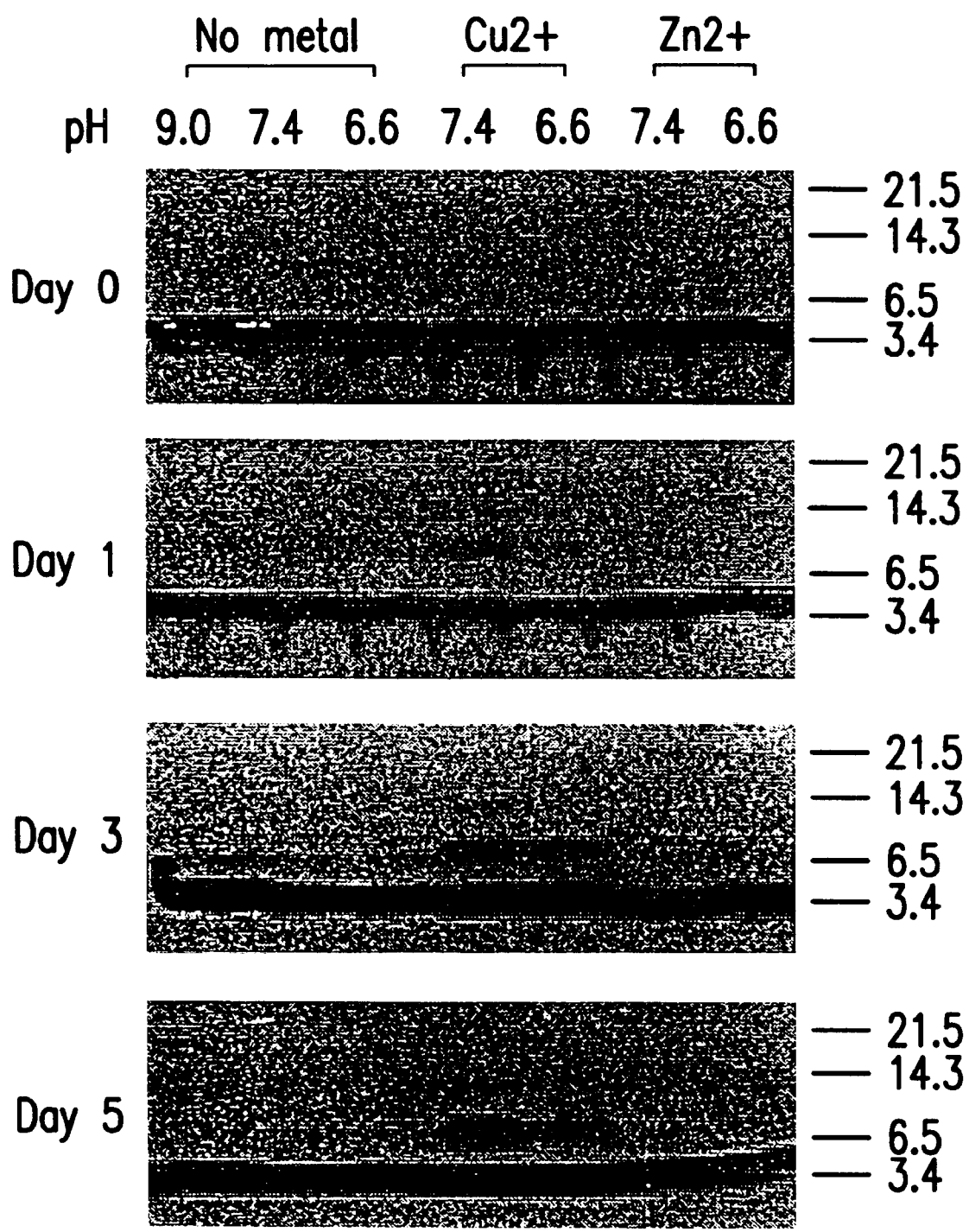
FIG. 9 is a western blot showing $A\beta$ SDS-resistant polymerization by copper.

Identical regions of frontal cortex (0.5 g) from postmortem brains of individuals with AD, as well as non-AD conditions, were homogenized in TBS, pH 4.7±metal chelators. The homogenate was centrifuged and samples of the soluble supernatant as well as the pellet were extracted into SDS sample buffer and assayed for Aβ content by western blotting using monoclonal antibody (mAb) WO2. The data shows a typical (of n=12 comparisons) result comparing the amount of Aβ extracted into the supernatant phase in AD compared to control (young adult) samples. N,N,N',N'-tetrakis [2-pyridyl-methyl] ethylenediamine (TPEN) (5 μM) allows the visualization of a population of pelletable Aβ that had not previously been recognized in unaffected brain samples (FIG. 8).

g) Aβ Polymerization by Copper $Cu^{2+}$-induced SDS-resistant oligomerization of Aβ: Aβ (2.5 μM), 150 mM NaCl, 20 mM hepes (pH 6.6, 7.4, 9) with or without $ZnCl_2$ or $CuCl_2$. Following incubation (37° C.), aliquots of each reaction (2 ng peptide) were collected at 0 d, 1 d, 3 d and 5 d and western blotted using anti-Aβ monoclonal antibody 8E10 (FIG. 9). Migration of the molecular size markers are indicated (kDa). The dimer formed under these conditions has been found to be SDS-resistant. $Cu^{2+}$ (2–30 μM) induced SDS-resistant polymerization of peptide. Co-incubation with similar concentrations of $Zn^{2+}$ accelerates the polymerization, but zinc alone has no effect. The antioxidant sodium metabisulfite moderately attenuates the reaction, while ascorbic acid dramatically accelerates Aβ polymerization. This suggests reduction of $Cu^{2+}$ to $Cu^+$ with the latter mediating SDS-resistant polymerization of Aβ. Mannitol also abolishes the polymerization, suggesting that the polymerization is mediated by the generation of the hydroxyl radical by a Fenton reaction that recruits $Cu^+$. It should be noted that other means of visualizing and/or determining the presence or absence of polymerization other than western blot analysis may be used. Such other means include but are not limited to density sedimentation by centrifugation of the samples.

Results

It has previously been reported that $Zn^{2+}$ induces rapid precipitation of Aβ in vitro (Bush, A. I., et al., *Science* 265:1464 (1994)). This metal has an abnormal metabolism in AD and is highly concentrated in brain regions where Aβ precipitates. The present data indicate that under very slightly acidic conditions, such as in the lactic acidotic AD brain, $Cu^{2+}$ strikingly induces the precipitation of Aβ through an unknown conformational shift. pH alone dramatically affects Aβsolubility, inducing precipitation when the pH of the incubation approaches the pI of the peptide (pH 5–6). Zinc induces 40–50% of the peptide to precipitate at pH>6.2, below pH 6.2 the precipitating effects of $Zn^{2+}$ and acid are not summative. At pH≦5, $Zn^{2+}$ has little effect upon Aβ solubility. $Cu^{2+}$ is more effective than $Zn^{2+}$ in precipitating Aβ and even induces precipitation at the physiologically relevant pH 6–7. Copper-induced precipitation of Aβ occurs as the pH falls below 7.0, comparable with conditions of acidosis (Yates, C. M., et al., *J. Neurochem.* 55:1624 (1990)) in the AD brain. Investigation of the precipitating effects of a host or other metal ions in this system indicated that metal ion precipitation of Aβ was limited to copper and zinc, as illustrated, although $Fe^{2+}$ possesses a partial capacity to induce precipitation (Bush, A. I., et al., *Science* 268:1921 (1995)).

On the basis these in vitro findings, the possibility that Aβ deposits in the AD-affected brain may be held in assembly by zinc and copper ions was investigated. Roher and colleagues have recently shown that much of the Aβ that deposits in AD-affected cortex can be solubilized in water (Roher, A. E, et al., *J. Biol. Chem.* 271:20631 (1996)). Supporting the clinical relevance of in vitro findings, it has recently been demonstrated that metal chelators increase the amount of Aβ extracted by Roher's technique (in neutral saline buffer), and that the extraction of Aβ is increased as the chelator employed has a higher affinity for zinc or copper. Hence TPEN is highly efficient in extracting Aβ, as are TETA, and bathocuproine, EGTA and EDTA are less efficient, requiring higher concentrations (91 mm) to achieve the same level of recovery as say, TPEN (5μM). Zinc and copper ions (5–50 μM) added back to the extracting solution abolish the recovery of Aβ (which is subsequently extracted by the SDS sample buffer in the pellet fraction of the centrifuged brain homogenate suspension), but $Ca^{2+}$ and $Mg^{2+}$ added back to the chelator-mediated extracts of Aβ cannot abolish Aβ resolubilization from AD-affected tissue even when these metal ions are present in millimolar concentrations.

Importantly, atomic absorption spectrophotometry assays of the metal content of the chelator-mediated extracts confirms that Cu and Zn are co-released with Aβ by the chelators, along with lower concentrations of Fe. These data strongly indicate that Aβ deposits (probably of the amorphous type) are held together by Cu and Zn and may also contain Fe. Interestingly, Aβ is not extractable from control brain without the use of chelators. This suggests that metal-assembled Aβ deposits may be the earliest step in the evolution of Aβ plaque pathology.

These findings propelled further inquiries into chemistry of metal ion-Aβ interaction. The precipitating effects upon Aβ of $Zn^{2+}$ and $Cu^{2+}$ were found to be qualitatively different. Zn-mediated aggregation is reversible with chelation and is not associated with neurotoxicity in primary neuronal cell cultures, whereas Cu-mediated aggregation is accompanied by the slow formation of covalently-bonded SDS-resistant dimers and induction of neurotoxicity. These neurotoxic SDS-resistant dimers are similar to those described by Roher (Roher, A. E, et al., *J. Biol. Chem.* 271:20631 (1996)).

Figure 1:
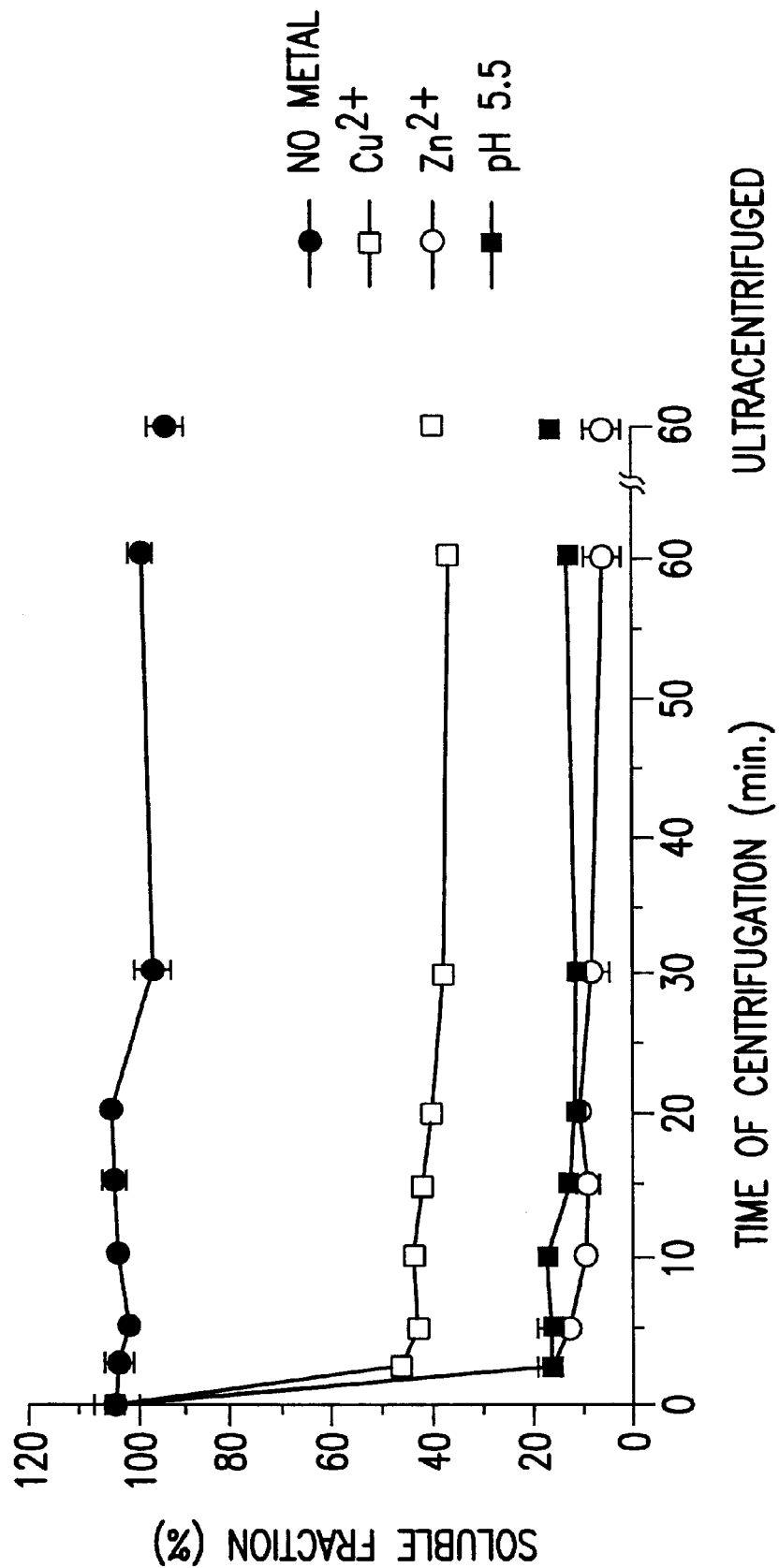
FIG. 1 is a graph showing the proportion of soluble $A\beta_{1-40}$ remaining following centrifugation of reaction mixtures.

To accurately quantitate the effects of different metals and pH on Aβ solubility, synthetic human $A\beta_{1-40}$ (2.5 μM) was incubated (37° C.) in the presence of metal ions at various pH for 30 min. The resultant aggregated particles were sedimented by centrifugation to permit determination of soluble $A\beta_{1-40}$ in the supernatant. To determine the centrifugation time required to completely sediment the aggregated particles generated under these conditions, $A\beta_{1-40}$ was incubated for 30 min at 37° C. with no metal, $Zn^{2+}$ (100 μM), $Cu^{2+}$ (100 μM) and pH (5.5). Reaction mixtures were centrifuged at 10,000 g for different times, or ultracentrifuged at 100,000 g for 1 h. (FIG. 1). FIG. 1 shows the proportion of soluble $A\beta_{1-40}$ remaining following centrifugation of reaction mixtures. $A\beta_{1-40}$ was incubated (30 min., 37° C.) with no metal, under acidic conditions (pH 5.5), $Zn^{2+}$ (100 μM) or $Cu^{2+}$ (100 μM), and centrifuged at 10,000 g for different time intervals, or at 100,000 g (ultracentrifuged) for 1 h for comparison. All data points are means±SD, n=3.

Figure 2A:
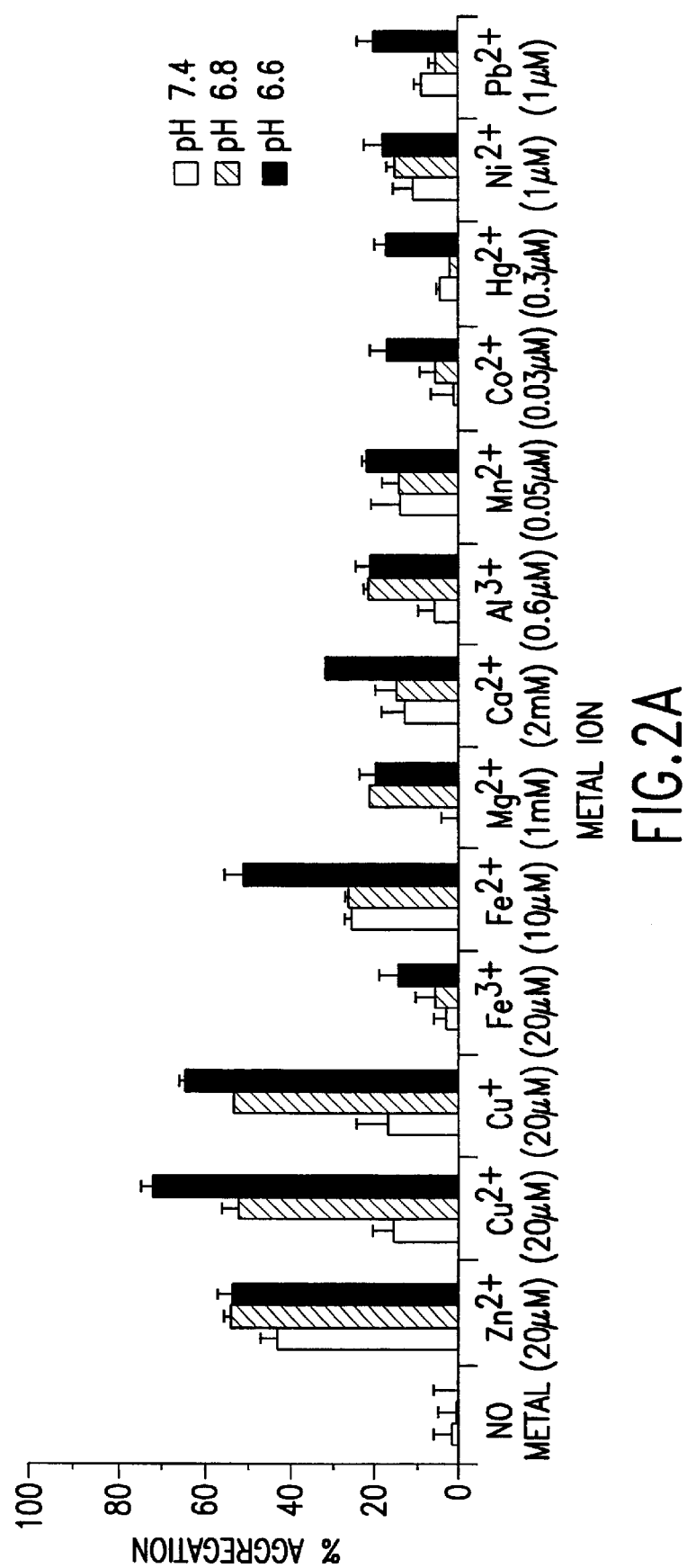
FIGS. 2A–2C.

Given that conformational changes within the N-terminal domain of Aβ are induced by modulating [H⁺] (Soto, C., et al., *J. Neurochem.* 7. 63:1191–1198 (1994)), and that there is a metal ($Zn^{2+}$) binding domain in the same region, experiments were designed to determine whether there was a synergistic effect of pH on metal ion-induced Aβ aggregation. $A\beta_{1-40}$ was incubated with different bioessential metal ions at pH 6.6, 6.8 and 7.4. The results are show in FIG. 2A, where "all metals" indicates incubation with a combination containing each metal ion at the nominated concentrations, concurrently. FIG. 2A shows the proportion of soluble $A\beta_{1-40}$ remaining in the supernatant after incubation (30 min., 37° C.) with various metals ions at pH 6.6, 6.8 or 7.4 after centrifugation (10,000 g, 20 min.).

The [H⁺] chosen represented the most extreme, yet physiologically plausible [H⁺] that $A\beta_{1-40}$ would be likely to encounter in vivo. The ability of different bioessential metal ions to aggregate $A\beta_{1-40}$ at increasing $H^{30}$ concentrations fell into two groups; $Mg^{2+}$, $Ca^{2+}$, $Al^{3+}$, $Co^{2+}$, $Hg^{2+}$, $Fe^{3+}$, $Pb^{2+}$ and $Cu^{2+}$ showed increasing sensitivity to induce $A\beta_{1-40}$ aggregation, while $Fe^{2+}$, $Mn^{2+}$, $Ni^{2+}$, and $Zn^{2+}$ were insensitive to alterations in [H⁺] in their ability to aggregate $A\beta_{1-40}$. $Cu^{2+}$ and $Hg^{2+}$ induced most aggregation as the [H⁺] increased, although the [H⁺] insensitive $Zn^{2+}$-induced aggregation produced a similar amount of aggregation. $Fe^{2+}$, but not $Fe^{3+}$, also induced considerable aggregation as the [H⁺] increased, possibly reflecting increased aggregation as a result of increased crosslinking of the peptide.

Figure 2B:
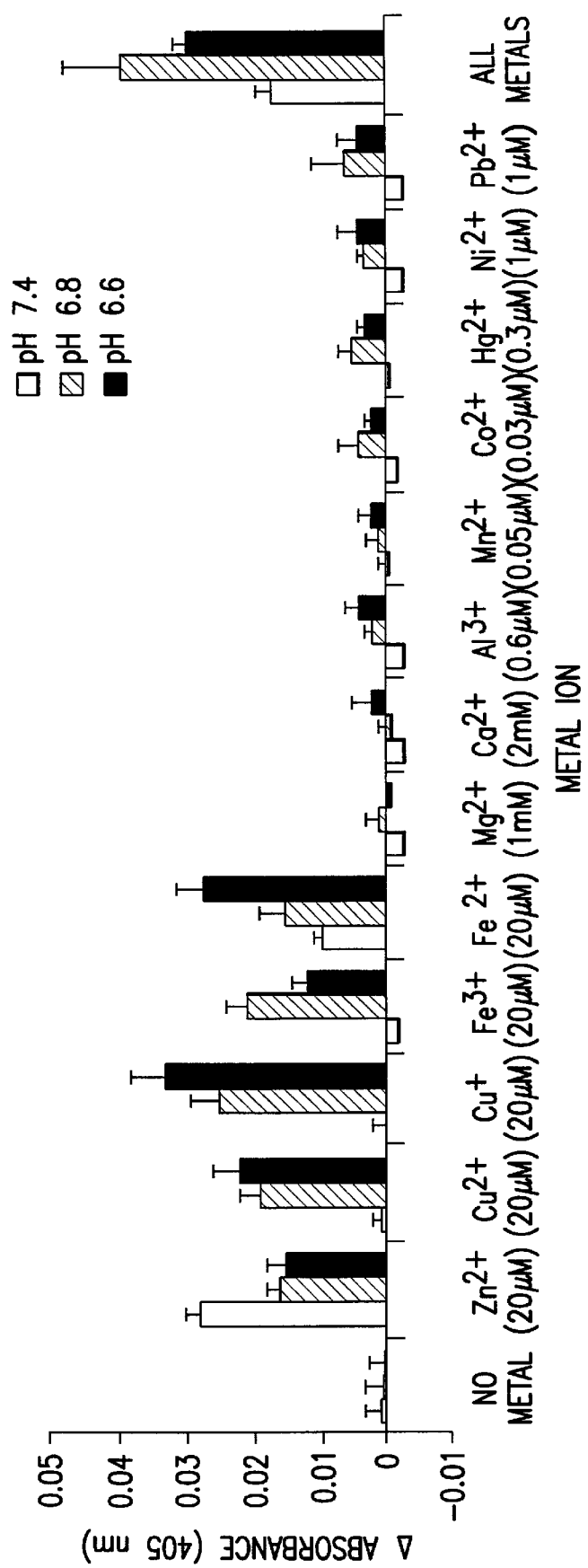
Figure 2C:
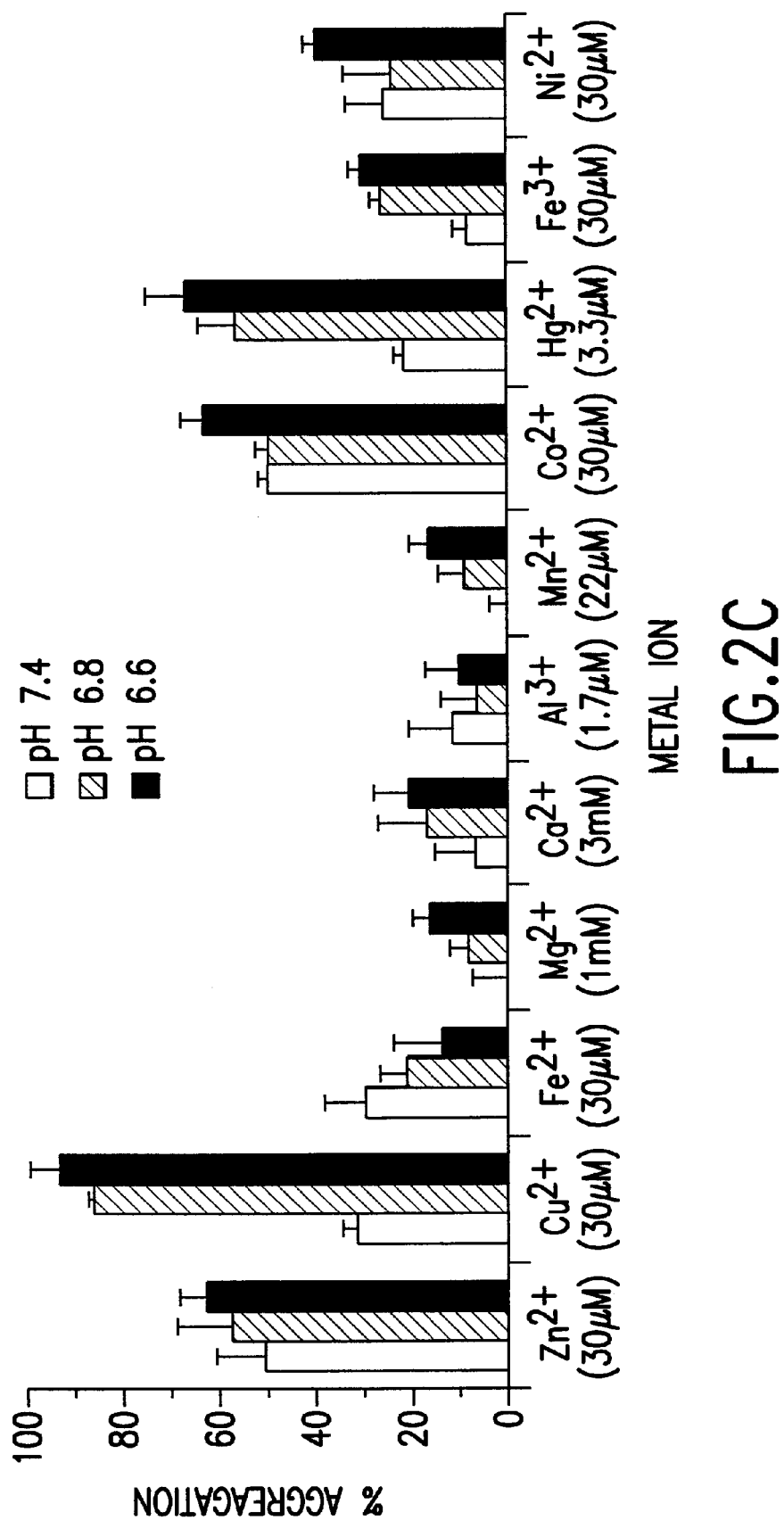

Similar results were obtained when these experiments were repeated using turbidometry as an index of aggregation (FIG. 2B). The data indicate the absorbance changes between reaction mixtures with and without metal ions at pH 6.6, 6.8 or 7.4. Thus, $A\beta_{1-40}$ has both a pH insensitive and a pH sensitive metal binding site. At higher concentrations of metal ions this pattern was repeated, except $Co^{2+}$ and $Al^{3+}$-induced Aβ aggregation became pH insensitive, and Mn became sensitive (FIG. 2C).

Figure 3:
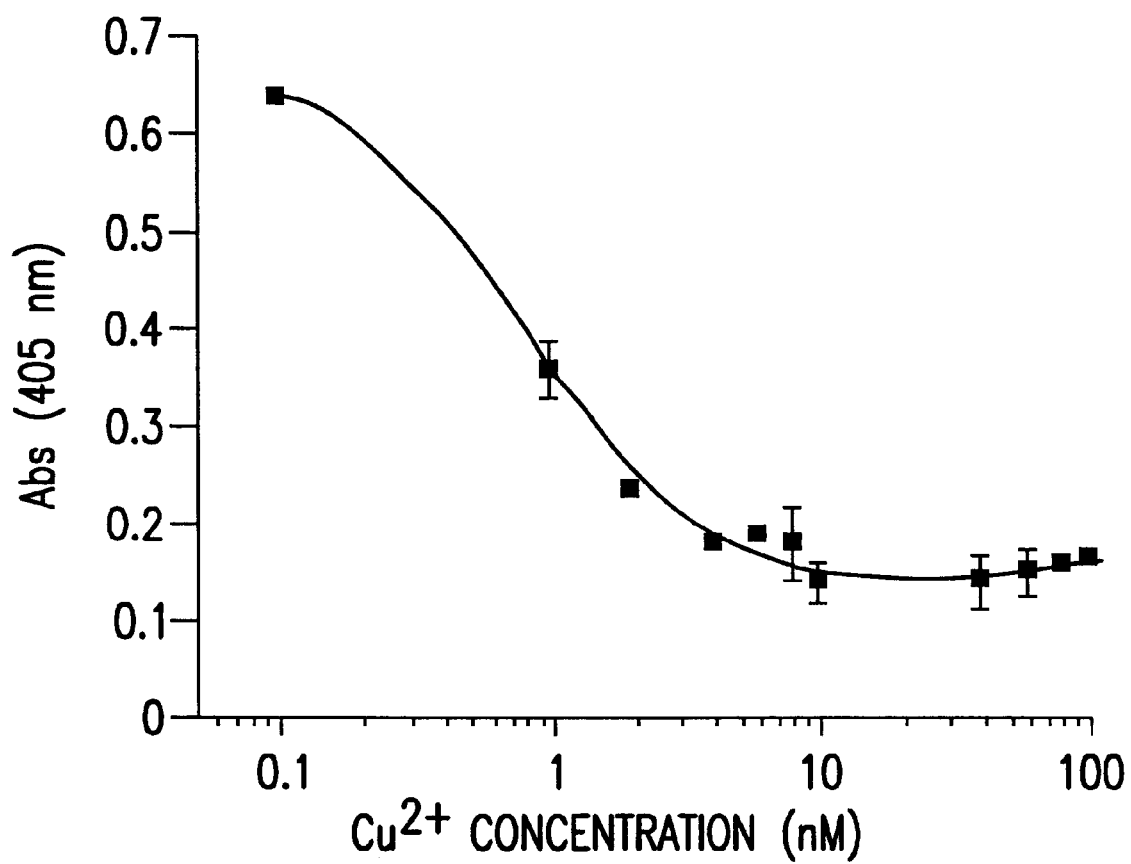
FIG. 3 is a graph showing a competition analysis of $A\beta_{1-40}$ binding to $Cu^{2+}$.

Since $^{64}CU$ is impractically short-lived (t½=13 h), a novel metal-capture ELISA assay was used to perform competition analysis of $A\beta_{1-40}$ binding to a microtiter plate impregnated with $Cu^{2+}$, as described in Materials and Methods. Results are shown in FIG. 3. All assays were performed in triplicate and are means±SD, n=3. Competition analysis revealed that $A\beta_{1-40}$ has at least one high affinity, saturable $Cu^{2+}$ binding site with a Kd=900 pM at pH 7.4 (FIG. 3). The affinity of Aβ for $Cu^{2+}$ is higher than that for $Zn^{2+}$ (Bush, A. I., et al., *J. Biol. Chem.* 269:12152 (1994)). Since $Cu^{2+}$ does not decrease $Zn^{2+}$-induced aggregation (Bush, A. I., et al., *J. Biol. Chem.* 269:12152 (1994)), indicating $Cu^{2+}$ does not displace bound $Zn^{2+}$, there are likely to be two separate metal binding sites. This is supported by the fact that there is both a pH sensitive and insensitive interaction with different metal ions.

Figure 4A:
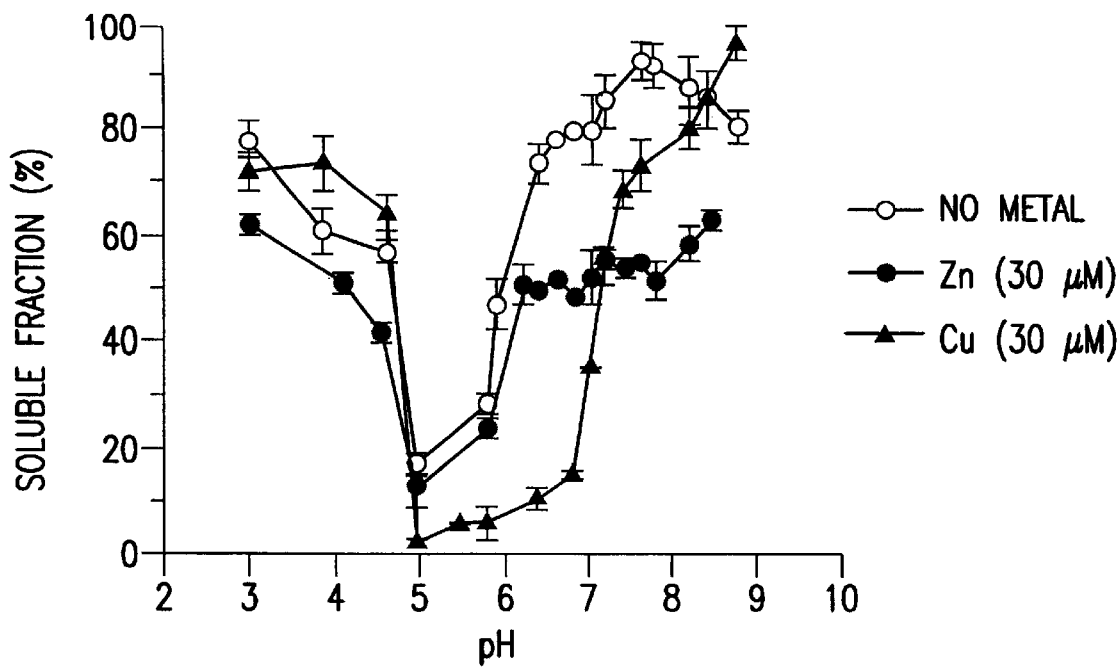
FIGS. 4A–4C.
Figure 4B:
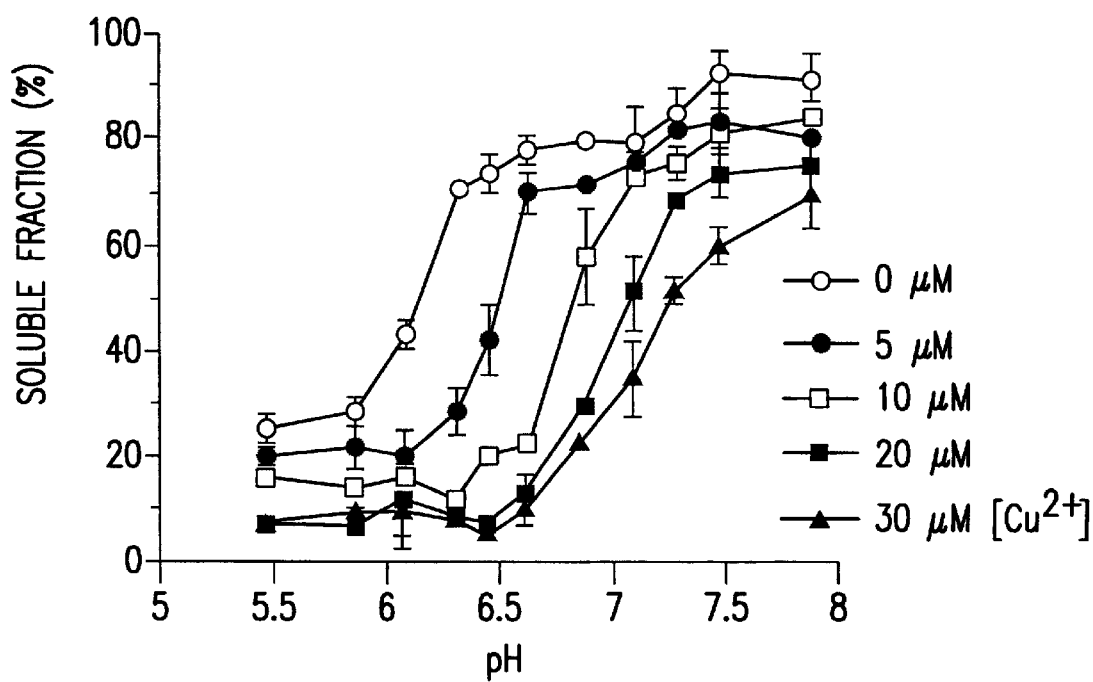
Figure 4C:
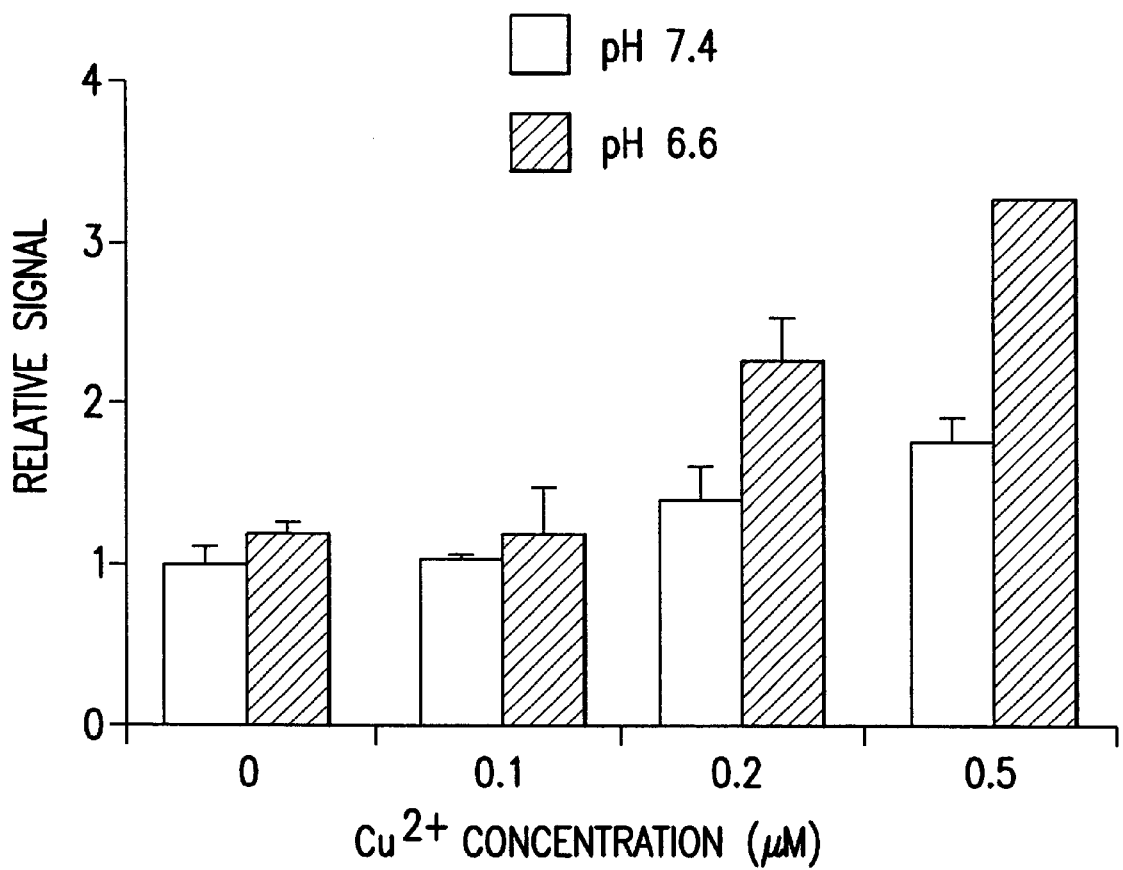

Since the conformational state and solubility of Aβ is altered at different pH (Soto, C., et al., *J. Neurochem.* 63:1191–1198 (1994)), the effects of [H⁺] on $Zn^{2+}$- and $Cu^+$-induced $A\beta_{1-40}$ aggregation were studied. Results are shown in FIGS. 4A, 4B and 4C. FIG. 4A shows the proportion of soluble $A\beta_{1-40}$ remaining in the supernatant following incubation (30 min., 37° C.) at pH 3.0–8.8 in buffered saline ±$Zn^{2+}$ (30 μM) or $Cu^{2+}$ (30 μM) and centrifugation (10,000 g, 20 min.), expressed as a percentage of starting peptide. All data points are means±SD, n=3. [H⁺] alone precipitates $A\beta_{1-40}$ (2.5 μM) as the solution is lowered below pH 7.4, and dramatically once the pH falls below 6.3 (FIG. 4A). At pH 5.0, 80% of the peptide is precipitated, but the peptide is not aggregated by acidic environments below pH 5, confirming and extending earlier reports on the effect of pH on Aβ solubility (Burdick, D., *J. Biol. Chem.* 267:546–554 (1992)). $Zn^{2+}$ (30 μM) induced a constant level (~50%) of aggregation between pH 6.2–8.5, while below pH 6.0, aggregation could be explained solely by the effect of [H⁺].

In the presence of $Cu^{2+}$ (30 μM), a decrease in pH from 8.8 to 7.4 induced a marked drop in $A\beta_{1-40}$ solubility, while a slight decrease below pH 7.4 strikingly potentiated the effect of $Cu^{2+}$ on the peptide's aggregation. Surprisingly, $Cu^{2+}$ caused>85% of the available peptide to aggregate by pH 6.8, a pH which plausibly represents a mildly acidotic environment. Thus, conformational changes in Aβ brought about by small increases in [$H^+$] result in the unmasking of a second metal binding site that leads to its rapid self-aggregation. Below pH 5.0, the ability of both $Zn^{2+}$ and $Cu^{2+}$ to aggregate Aβ was diminished, consistent with the fact that Zn binding to Aβ is abolished below pH 6.0 (Bush, A. I., et al., *J. Biol. Chem.* 269:12152 (1994)), probably due to protonation of histidine residues.

The relationship between pH and $Cu^{2+}$ on $Aβ_{1-40}$ solubility was then further defined by the following experiments (FIG. 4B). The proportion of soluble $Aβ_{1-40}$ remaining in the supernatant after incubation (30 min., 37° C.) at pH 5.4–7.8 with different $Cu^{2+}$ concentrations (0, 5, 10, 20, 30 μM), and centrifugation (10,000 g, 20 min.), was measured and expressed as a percentage of starting peptide. All data points are means±SD, n=3. At pH 7.4, $Cu^{2+}$-induced Aβ aggregation was 50% less than that induced by $Zn^{2+}$ over the same concentration range, consistent with earlier reports (Bush, A. I., et al., *J. Biol. Chem.* 269:12152 (1994)). There was a potentiating relationship between [$H^+$] and [$Cu^{2+}$] in producing Aβ aggregation; as the pH fell, less $Cu^{2+}$ was required to induce the same level of aggregation, suggesting that [$H^+$] is controlling $Cu^{2+}$ induced $Aβ_{1-40}$ aggregation.

To confirm that this reaction occurs at physiological concentrations of $Aβ_{1-40}$ and $Cu^{2+}$, a novel filtration immunodetection system was employed. This technique enabled the determination of the relative amount of $Aβ_{1-40}$ aggregation in the presence of different concentrations of $H^+$ and $Cu^{2+}$ (FIG. 4C). The relative aggregation of nM concentrations of $Aβ_{1-40}$ at pH 7.4 and pH 6.6 in the presence of different $Cu^{2+}$ concentrations (0, 0.1, 0.2, 0.5 μM) were determined by this method. Data represent mean reflectance values of immunoblot densitometry expressed as a ratio of the signal obtained when the peptide is treated in the absence of $Cu^{2+}$. All data points are means±SD, n=2.

This sensitive technique confirmed that physiological concentrations of $Aβ_{1-40}$ are aggregated under mildly acidic conditions and that aggregation was greatly enhanced by the presence of $Cu^{2+}$ at concentrations as low as 200 nM. Furthermore, as previously observed at higher $Aβ_{1-40}$ concentrations, a decrease in pH from 7.4 to 6.6 potentiated the effect of $Cu^{2+}$ on aggregation of physiological concentrations of $Aβ_{1-40}$. Thus, $Aβ_{1-40}$ aggregation is concentration independent down to 8 nM where $Cu^{2+}$ is available.

It has recently been shown that $Zn^{2+}$ mediated $Aβ_{1-40}$ aggregation is reversible whereas $Aβ_{1-40}$ aggregation induced by pH 5.5 was irreversible. Therefore. experiments were performed to determine whether $Cu^{2+}$/pH-mediated $Aβ_{1-40}$ aggregation was reversible. $Cu^{2+}$-induced $Aβ_{1-40}$ aggregation at pH 17.4 was reversible following EDTA chelation, although for each new aggregation cycle, complete resolubilization of the aggregates required a longer incubation. This result suggested that a more complex aggregate is formed during each subsequent aggregation cycle, preventing the chelator access to remove $Cu^{2+}$ from the peptide. This is supported by the fact that complete resolubilization occurs with time, and indicates that the peptide is not adopting a structural conformation that is insensitive to $Cu^{2+}$-induced aggregation/EDTA-resolubilization.

Figure 5A:
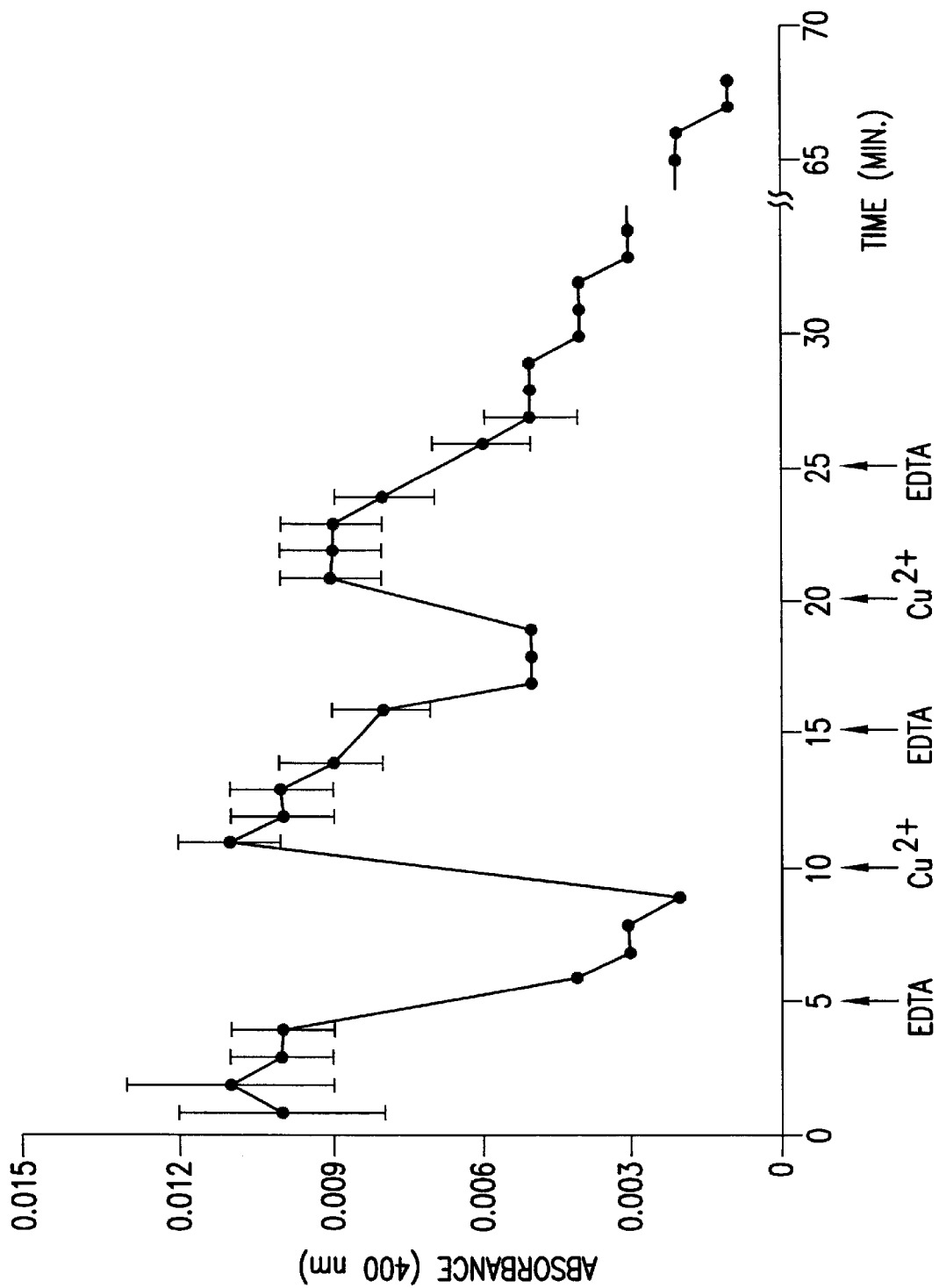
FIGS. 5A and 5B.
Figure 5B:
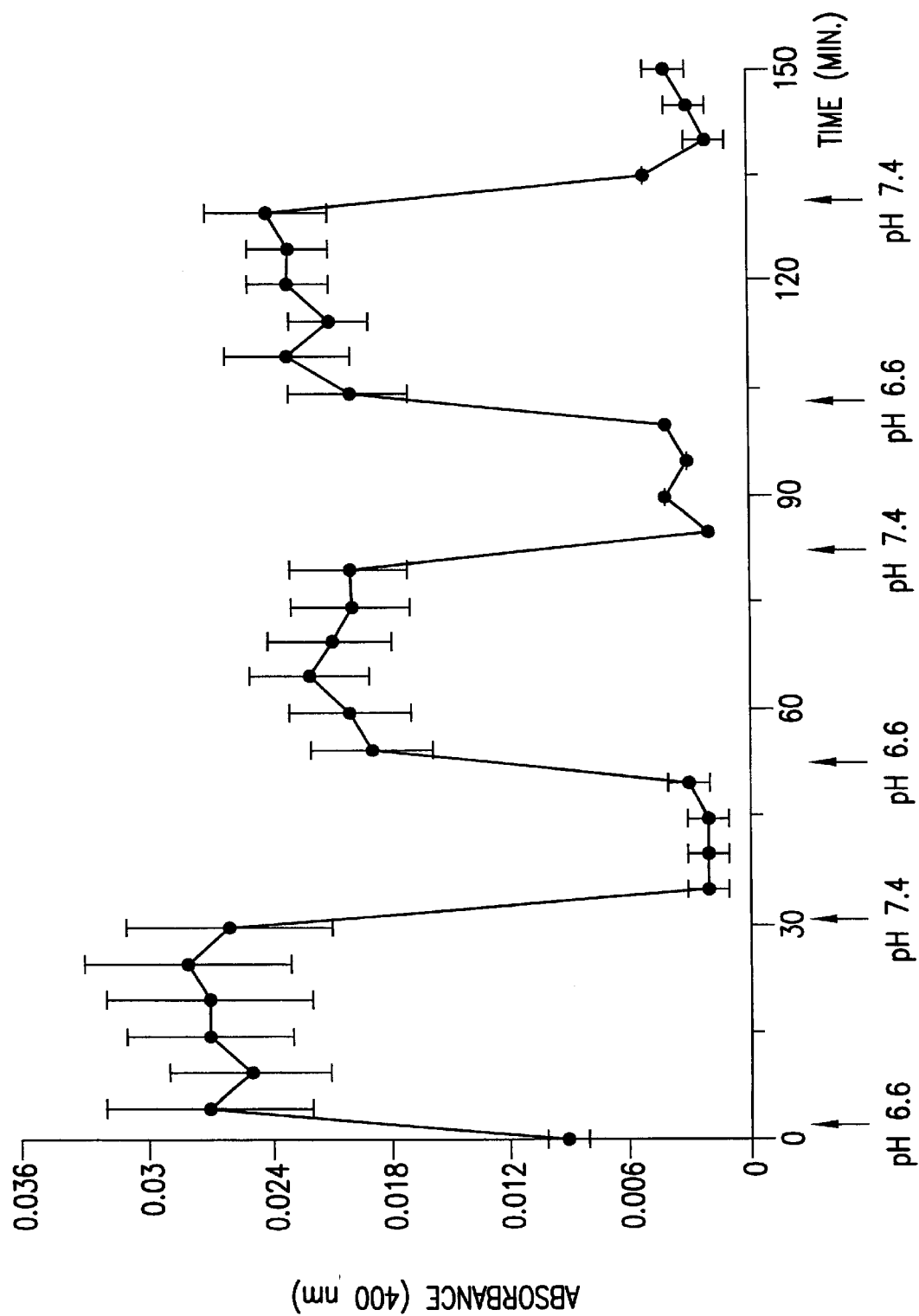

The reversibility of pH potentiated $Cu^{2+}$-induced $Aβ_{1-40}$ aggregation was studied by turbidometry between pH 7,5 to 6.6, representing $H^+$ concentration extremes that might be found in vivo (FIGS. 5A and 5B). Unlike the irreversible aggregation of $Aβ_{1-40}$ observed at pH 5.5. $Cu^{2+}$-induced $Aβ_{1-40}$ aggregation was fully reversible as the pH oscillated between pH 7.4 and 6.6. FIG. 5A shows the turbidometric analysis of $Cu^{2+}$-induced $Aβ_{1-40}$ aggregation at pH 7.4 reversed by successive cycles of chelator (EDTA), as indicated. FIG. 5B shows turbidometric analysis of the reversibility of $Cu^{2+}$-induced $Aβ_{1-40}$ as the pH cycles between 7.4 and 6.6. Thus, subtle conformational changes within the peptide induced by changing [$H^+$] within a narrow pH window, that corresponds to physiologically plausible [$H^+$], allows the aggregation or resolubilization of the peptide in the presence of $Cu^{2+}$.

Discussion

These results suggest that subtle conformational changes in Aβ induced by [$H^+$] promote the interaction of $Aβ_{1-40}$ with metal ions, in particular $Cu^{2+}$ and $Hg^{2+}$ allowing self-aggregate or resolubilize depending on the [$H^+$] (FIGS. 2A–2C, 4A–4C). A decrease in pH below 7.0 increases the β-sheet conformation (Soto, C., et al., *J. Neurochem.* 63:1191–1198 (1994)), and this may allow the binding of $Cu^{2+}$ to soluble Aβ that could further alter the conformation of the peptide allowing for self aggregation, or simply help coordinate adjacent Aβ molecules in the assembly of the peptides into aggregates. Conversely, increasing pH above 7.0 promotes the c-helical conformation (Soto, C., et al., *J. Neurochem.* 63:1191–1198 (1994)), which may alter the conformational state of the dimeric aggregated peptide, releasing Cu and thereby destabilizing the aggregate with the resultant release of Aβ into solution. Thus, in the presence of $Cu^{2+}$, $Aβ_{1-40}$ oscillates between an aggregated and soluble state dependent upon the [$H^+$].

$Aβ_{1-40}$ aggregation by $Co^{2+}$, like $Zn^{2+}$, was pH insensitive and per mole induced a similar level of aggregation. Unlike $Zn^{2+}$, $Aβ_{1-40}$ binding of $Co^{2+}$ may be employed for the structural determination of the pH insensitive binding site given its nuclear magnetic capabilities (See FIG. 2C).

The biphasic relationship of Aβ solubility with pH mirrors the conformational changes previously observed by CD spectra within the N-terminal fragment (residues 1–28) of Aβ (reviewed in (Soto, C., et al., *J. Neurochem.* 63:1191–1198 (1994)); α-helical between pH 1–4 and>7, but β-sheet between pH 4–7. The irreversible aggregates of Aβ formed at pH 5.5 supports the hypothesis that the β-sheet conformation is a pathway for Aβ aggregation into amyloid fibrils. Since aggregates produced by $Zn^{2+}$ and $Cu^{2+}$ under mildly acidic conditions (FIGS. 5A and 5B) are chelator/pH reversible, their conformation may be the higher energy α-helical conformation.

These results now indicate that there are three physiologically plausible conditions which could aggregate Aβ: pH (FIGS. 1, 4A–4C; Fraser, P. E., et al., *Biophys. J.* 60:1190–1201 (1991); Barrow, C. J. and Zagorski, M. G., *Science* 253:179–182 (1991); Burdick, D., *J. Biol. Chem.* 267:546–554 (1992); Barrow, C. J., et al., *J. Mol. Biol.* 225:1075–1093 (1992); Zagorski, M. G. and Barrow, C. J., *Biochemistry* 31:5621–5631 (1992); Kirshenbaum, K. and Daggett, V., *Biochemistry* 34:7629–7639 (1995); Wood, S. J., et al., *J. Mol. Biol.* 256:870–877 (1996)), [$Zn^{2+}$] (FIGS. 1, 2A and 2B, 4A–4C; Bush, A. I., et al., *J. Biol. Chem.* 269:12152 (1994); Bush, A. I., et al, *Science* 265:1464 (1994); Bush, A. I., et al., *Science* 268:1921 (1995); Wood, S. J., et al., *J. Mol. Biol.* 256:870–877 (1996)) and under mildly acidic conditions, [$Cu^{2+}$] (FIGS. 2A, 4A–4C, 5B). Interestingly, changes in metal ion concentrations and p11 are common features of the inflammatory response to injury. Therefore, the binding of $Cu^{2+}$ and $Zn^{2+}$ to Aβ may be of particular importance during inflammatory processes, since local sites of inflammation can become acidic (Trehauf, P. S. & McCarty, D. J., *Arthr. Rheum.* 14:475–484 (1971); Menkin, V., *Am. J. Pathol.* 10:193–210 (1934)) and both $Zn^{2+}$ and $Cu^{2+}$ are rapidly mobilized in response to inflammation (Lindeman, R. D., et al., *J. Lab. Clin. Med.* 81:194–204 (1973); Terhune, M. W. & Sandstead, H. H., *Science* 177:68–69 (1972); Hsu, J. M., et al., *J. Nutrition* 99:425–432 (1969); Haley, J. V., *J. Surg. Res.* 27:168–174 (1979); Milaninio, R., et al., *Advances in Inflammation Research* 1:281–291 (1979); Frieden, F., in *Inflammatory Diseases and Copper,* Sorenson, J. R. J., ed, Humana Press, New Jersey (1980), pp. 159–169).

Serum copper levels increase during inflammation, associated with increases in ceruloplasmin, a $Cu^{2+}$ transporting protein that may donate $Cu^{2+}$ to enzymes active in processes of basic metabolism and wound healing such as cytochrome oxidase and lysyl oxidase (Giampaolo, V., et al., in *Inflammatory Diseases and Copper,* Sorenson, J. R. J., ed, Humana Press, New Jersey (1980), pp. 329–345; Peacock, E. E. and van Winkle, W., in Wound Repair, W. B. Saunders Co., Philadelphia, pp. 145–155) (1976)). Since the release of $Cu^{2+}$ from ceruloplasmin is greatly facilitated by acidic environments where the cupric ion is reduced to its cuprous form (Owen, C. A., Jr., *Proc. Soc. Exp. Biol. Med.* 149:681–682 (1975)), periods of mild acidosis may promote an environment of increased free $Cu^{2+}$. Similarly, aggregation of another amyloid protein, the acute phase reactant serum amyloid P component (SAP) to the cell wall polysaccharide, zymosan, has been observed with $Cu^{2+}$ at acidic pH (Potempa, L. A., et al., *Journal of Biological Chemistry* 260:12142–12147 (1985)). Thus, exchange of $Cu^{2+}$ to $A\beta_{1-40}$ during times of decreased pH may provide a mechanism for altering the biochemical reactivity of the protein required by the cell under mildly acidic conditions. Such a function may involve alterations in the aggregation/adhesive properties (FIGS. 1–5B) or oxidative functions of $A\beta$ at local sites of inflammation.

While the pathogenic nature of $A\beta_{1-42}$ in AD is well described (Maury, C. P. J., *Lab. Investig.* 72:4–16 (1995); Multhaup, G., et al., *Nature* 325:733–736 (1987)), the function of the smaller $A\beta_{1-40}$ remains unclear. The present data suggest that $Cu^{2+}$-binding and aggregation of $A\beta$ will occur when the pH of the microenvironment rises. This conclusion can be based on the finding that the reaction is $[H^+]$ and $[Cu^{2+}]$ dependent and reversible within a narrow, physiologically plausible, pH window. This is further supported by the specificity and high affinity of $Cu^{2+}$ binding under mildly acidic conditions compared to the constant $Zn^{2+}$-induced aggregation (and binding) of $A\beta_{1-40}$ over a wide pH range (6.2–8.5). The brain contains high levels of both $Zn^{2+}$ (~150 $\mu M$; Frederickson, C. J. *International Review of Neurobiology* 31:145–237 (1989)) and $Cu^{2+}$ (~100 $\mu M$; Warren, P. J., et al., *Brain* 83:709–717 (1960); Owen, Calif., *Physiological Aspects of Copper,* Noyes Publications, Park Ridge, N.J. (1982), pp 160–191). Intracellular concentrations are approximately 1000 and 100 fold higher than extracellular concentrations. This large gradient between intracellular and extracellular compartments suggests a highly energy dependent mechanism is required in order to sequester these metals within neurons. Therefore, any alterations in energy metabolism, or injury, may affect the reuptake of these metal ions and promote their release into the extracellular space, and together with the synergistic affects of decreased pH (see above) induce membrane bound $A\beta_{1-40}$ to aggregate. Since increased concentrations of $Zn^{2+}$ and $Cu^{2+}$, and decreased pH, are common features of all forms of cellular insult, the initiation of $A\beta_{1-40}$ function likely occurs in a coordinated fashion to alter adhesive and/or oxidative properties of this membrane protein essential for maintaining cell integrity and viability. That $A\beta_{1-40}$ has such a high affinity for these metal ions, indicates a protein that has evolved to respond to slight changes in the concentration of extracellular metal ions. This is supported by the fact that aggregation in the presence of Cu is approx. 30% at pH 7.1, the pH of the brain (Yates, C. M., et al., *J. Neitrochem.* 55:1624–1630 (1990)), but 85% at pH 6.8. Taken together, our present results indicate that $A\beta_{1-40}$ may have evolved to respond to biochemical changes associated with neuronal damage as part of the locally mediated response to inflammation or cell injury. Thus, it is possible that $Cu^{2+}$ mediated $A\beta_{1-40}$ binding and aggregation might be a purposive cellular response to an environment of mild acidosis.

The deposition of amyloid systemically is usually associated with an inflammatory response (Pepys, M. B. & Baltz, M. L., *Adv. Immunol.* 34:141–212 (1983); Cohen, A. S., in *Arthritis and allied Conditions,* D. J. McCarty, ed., Lea and Febiger, Philadelphia, pp. 1273–1293 (1989); Kisilevsky, R., *Lab. Investig.* 49:381–390 (1983)). For example, serum amyloid A, one of the major acute phase reactant proteins that is elevated during inflammation, is the precursor of amyloid A protein that is deposited in various tissues during chronic inflammation, leading to secondary amyloidosis (Gorevic, P. D., et al., *Ann. NY Acad. Sci.* 380.393 (1982)). An involvement of inflammatory mechanisms has been suggested as contributing to plaque formation in AD (Kisilevsky, R., *Mol. Neurobiol.* 49:65–66 (1994)). Acute-phase proteins such as alpha 1-antichymotrypsin and c-reactive protein, elements of the complement system and activated microglial and astroglial cells are consistently found in AD brains.

The rapid appearance, within days of $A\beta$ deposits and APP immunoreactivity following head injury (Roberts, G. W., et al., *Lancet.* 338:1422–1423 (1991); Pierce, J. E. S., et al., *Journal of Neuroscience* 16:1083–1090 (1996)), rather than the more gradual accumulation of $A\beta$ into more dense core amyloid plaques over months or years in AD may be compatible with the release of $Zn^{2+}$, $Cu^{2+}$ and mild acidosis in this time frame. Thus, pH/metal ion mediated aggregation may form the basis for the amorphous $A\beta$ deposits observed in the aging brain and following head injury, allowing the maintenance of endothelial and neuronal integrity while limiting the oxidative stress associated with injury that may lead to a diminishment of structural function.

Since decreased cerebral pH is a complication of aging (Yates, C. M., et al., *J. Neurochem.* 55:1624–1630 (1990)), these data indicate that Cu and Zn mediated $A\beta$ aggregation may be a normal cellular response to an environment of mild acidosis. However, prolonged exposure of $A\beta$ to an environment of lowered cerebral pH may promote increased concentrations of free metal ions and reactive oxygen species, and the inappropriate interaction of $A\beta_{1-42}$ over time promoting the formation of irreversible $A\beta$ oligomers and it's subsequent deposition as amyloid in AD. The reversibility of this pH mediated $Cu^{2+}$ aggregation does however present the potential for therapeutic intervention. Thus, cerebral alkalinization may be explored as a therapeutic modality for the reversibility of amyloid deposition in vivo.

Example 2

Free Radical Formation and SOD-like activity of Alzizeimer's Aβ Peptides

Materials and Methods a) Determination of $Cu^+$ and $Fe^{2+}$

This method is modified from a protocol assaying serum copper and iron (Landers, J. W., et al., *Amer. Clin. Path.* 29:590 (1958)). It is based on the fact that there are optimal visible absorption wavelengths of 483 nm and 535 nm for $Cu^+$ complexed with bathocuproinedisulfonic (BC) anion and $Fe^{2+}$ coordinated by bathophenanthrolinedisulfonic (BP) anion, respectively.

Determination of molar absorption of these two complexes was accomplished essentially as follows. An aliquot of 500 μl of each complex (500 μM, in PBS pH 7.4, with ligands in excess) was pipetted into 1 cm-pathlength quartz cuvette, and their absorbancies were measured. Their molar absorbancy was determined based on Beer-Lambert's Law. $Cu^+$-BC has a molar absorbancy of 2762 $M^{-1}$ $cm^{-1}$, while $Fe^{2+}$-BP has a molar absorbancy of 7124 $M^{-1}$ $cm^{-1}$.

Determination of the equivalent vertical pathlength for $Cu^+$-BC and $Fe^{2+}$-BP in a 96-well plate was carried out essentially as follows. Absorbencies of the two complexes with a 500 μM, 100 μM, 50 μM, and 10 μM concentration of relevant metal ions ($Cu^+$, $Fe^{2+}$) were determined both by 96-well plate readers (300 μL) and UV-vis spectrometer (500 μL), with PBS, pH 7.4, as the control blank. The resulting absorbancies from the plate reader regress against absorbancies by a UV-vis spectrometer. The slope k from the linear regression line is equivalent to the vertical pathlength if the measurement is carried out on a plate. The results are:

|  | k(cm) | $r^2$ |
|---|---|---|
| $Cu^+$—BC | 1.049 | 0.998 |
| $Fe^{2+}$—BP | 0.856 | 0.999 |

With molar absorbancy and equivalent vertical pathlength in hand, the concentrations (μM) of $Cu^+$ or $Fe^{2+}$ can be deduced based on Beer-Lambert's Law, using proper buffers as controls.

$$\text{for } Fe^{2+}: \quad [Fe^{2+}] (\mu M) = \frac{\Delta A \ (535 nm)}{(7124 \times 0.856)} \times 10^6$$

$$\text{for } Cu^+: \quad [Cu^+] (\mu M) = \frac{\Delta A \ (483 nm)}{(2762 \times 1.049)} \times 10^6$$

where ΔA is absorbancy difference between sample and control blank.

b) Determination of $H_2O_2$

This method is modified from a $H_2O_2$ assay reported recently (Han, J. C., et al., *Anal. Biochem.* 234:107 (1996)). The advantages of this modified $H_2O_2$ assay on 96-well plate include high throughput, excellent sensitivity (~1 μM), and the elimination of the need for a standard curve of $H_2O_2$, which is problematic due to the labile chemical property of $H_2O_2$.

Aβ peptides were co-incubated with a $H_2O_2$-trapping reagent (Tris(2-carboxyethyl)-phosphine hydrochloride, TCEP, 100 μM) in PBS (pH 7.4 or 7.0) at 37° C. for 30 mins. Then 5,5'-dithio-bis(2-nitrobenzoic acid) (DBTNB, 100 μM) was added to react with remaining TCEP. The product of this reaction has a characteristic absorbance maximum of 412 nm [18]. The assay was adapted to a 96-well format using a standard absorbance range (see FIG. 11).

The chemical scheme for this novel method is:

Scheme I

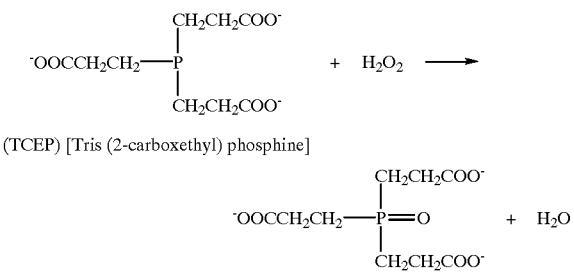

(TCEP) [Tris (2-carboxethyl) phosphine]

Scheme II

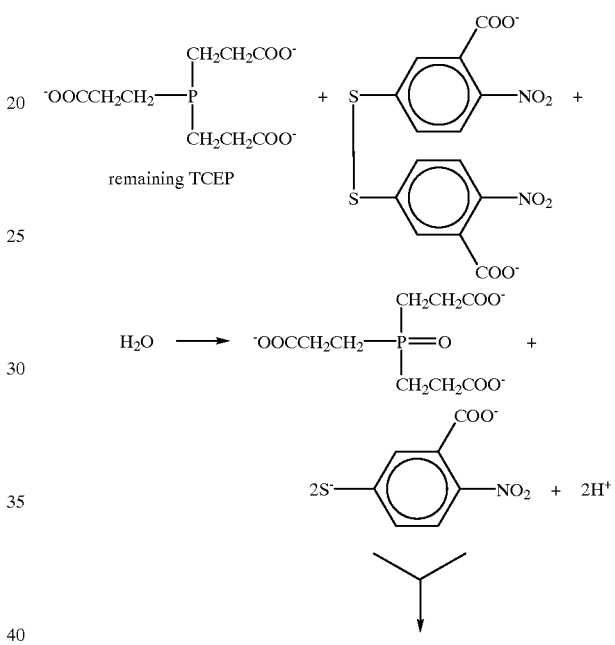

has characteristic optimal absorption peak at 412 nm with 14,150 $M^{-1}$ $cm^{-1}$ molar extinction coefficient TCEP•HCl was synthesized by hydrolyzing tris (2-cynoethyl) phosphine (purchased from Johnson-Mathey (Waydhill, Mass.)), in refluxing aqueous HCl (Burns, J. A., et al., *J. Org. Chem.* 56:2648 (1991)) as shown below.

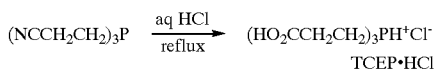

In order to carry out the above-described assay in a 96-well plate, it was necessary to calculate the equivalent vertical pathlength of 2-nitro-5-thiobenzoic acid (TMB) in a 96-well plate. This determination was carried out essentially as described for $Cu^+$-BC and $Fe^{2+}$-BP in Example 5. The resulting absorbancies from the plate reader regress against absorbancies by a UV-vis spectrometer. The slope k from the linear regression line is equivalent to the vertical pathlength if the measurement is carried out on a plate. The results are:

| k | r2 |
|---|---|
| 0.875 | 1.00 |

The concentration of $H_2O_2$ can then be deduced from the difference in absorbance between the sample and the control (sample plus 1000 U/µl catalase)

$$[H_2O_2]\ [\mu M] = \frac{\Delta A\ (412nm)}{(2 \times 0.875 \times 14150)}$$

c) Determination of OH•

Determination of OH• was performed as described in Gutteridge et al. *Biochim. Biophys. Acta* 759: 38–41 (1983).

d) $Cu^+$ Generation by Aβ: Influence of $Zn^{2+}$ and pH

Aβ (10 µM in PBS, pH 7.4 or 6.8, as shown) was incubated for 30 minutes (37° C.) in the presence of $Cu^{2+}$ 10 µM±$Zn^{2+}$ 10 µM). $Cu^+$ levels (n=3, ±SD) were assayed against a standard curve. These data indicate that the presence of $Zn^{2+}$ can mediate the reduction of $Cu^{2+}$ in a mildly acidic environment. The effects of zinc upon these reactions are strongly in evidence but complex. Since the presence of 10 µM zinc will precipitate the peptide, it is clear that the peptide possesses redox activity even when it is not in the soluble phase, suggesting that cortical Aβ deposits will not be inert in terms of generating these highly reactive products. Cerebral zinc metabolism is deregulated in AD, and therefore levels of interstitial zinc may play an important role in adjusting the $Cu^+$ and $H_2O_2$ production generated by Aβ. The rat homologue of Aβ$_{1-40}$ does not manifest the redox reactivity of the human equivalent. Insulin, a histidine-containing peptide that can bind copper and zinc, exhibits no $Cu^{2+}$ reduction.

e) Hydrogen Peroxide Production by Aβ species

Aβ$_{1-42}$ (10 µM) was incubated for 1 hr at 37° C., pH 7.4 in ambient air (first bar), continuous argon purging (Ar), continuous oxygen enrichment ($O_2$) at pH 7.0 (7.0), or in the presence of the iron chelator desferioxamine (220 µM; DFO). Variant Aβ species (10 µM) were tested: Aβ$_{1-40}$ (Aβ$_{1-40}$), rat Aβ$_{1-40}$ (rAβ$_{1-40}$), and scrambled Aβ$_{1-40}$ (sAβ$_{1-40}$) were incubated for 1 hr at 37° C., pH 7.4 in ambient air. Values (mean±SD, n=3) represent triplicate samples minus values derived from control samples run under identical conditions in the presence of catalase (10 U/ml). The details of the experiment are as follows: Aβ peptides were co-incubated with a $H_2O_2$-trapping reagent (Tris(2-carboxyethyl)-phosphine hydrochloride, TCEP, 100 µM) in PBS (pH 7.4 or 7.0) at 37° C. for 30 mins. Then 5,5'-dithio-bis(2-nitrobenzoic acid) (DTNB, 100 µM) was added to react with remaining TCEP, the product has a characteristic absorbance maximum of 412 mm. The assay was adapted to a 96-well format using a standard absorbance range.

Results and Discussion

Aβ exhibits Metal-dependent and Independent Redox Activity

Figure 10:
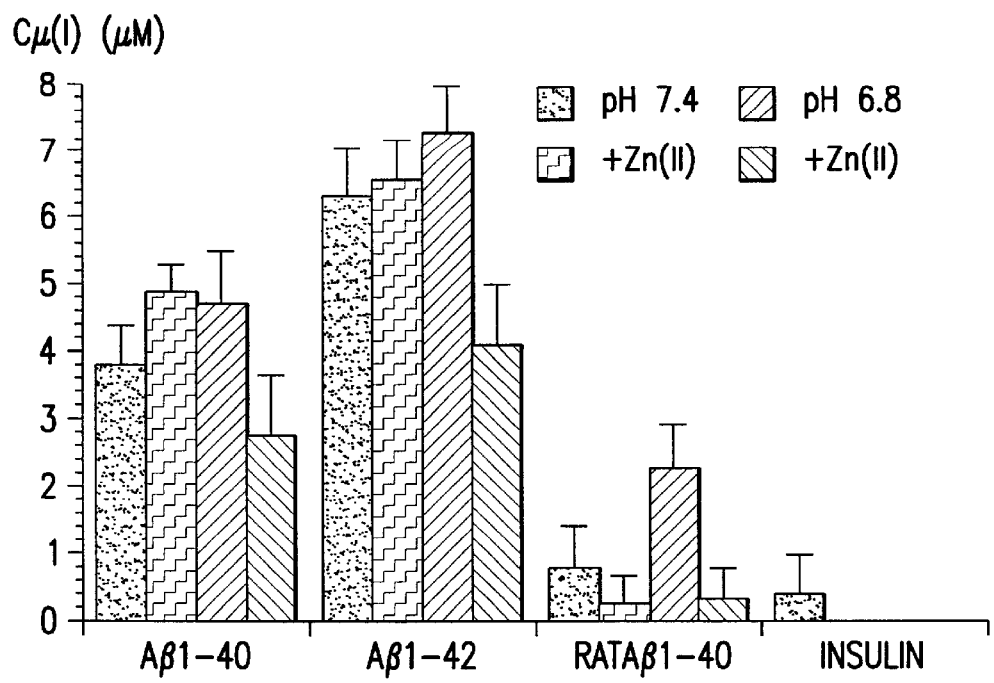
FIG. 10 is a graph showing $Cu^+$ generation by $A\beta$.
Figure 11:
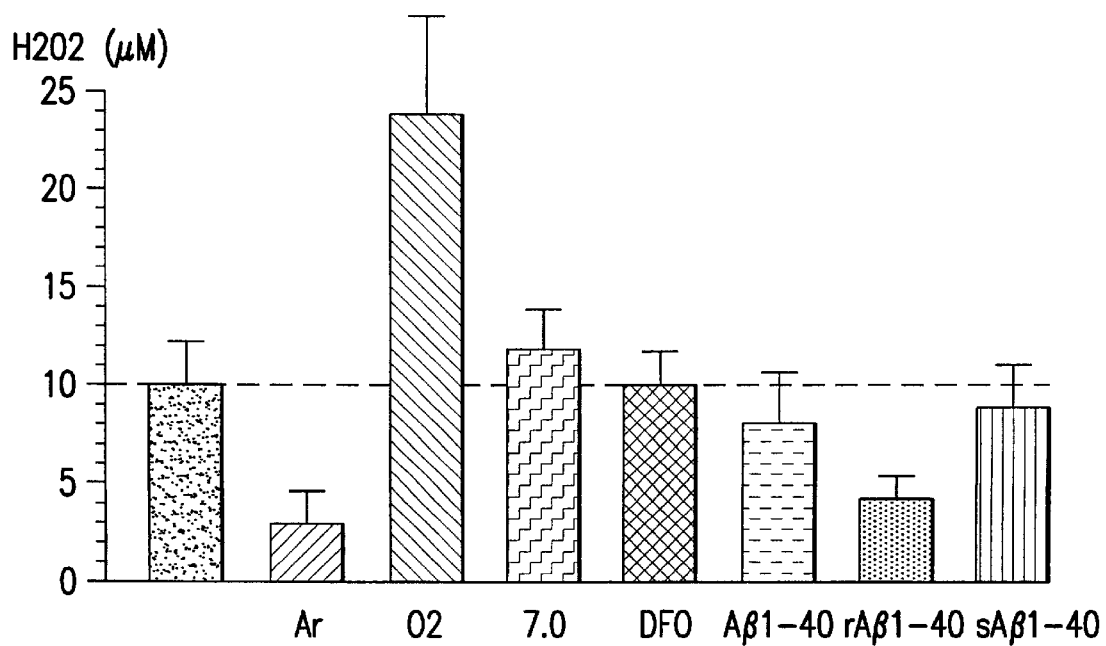
FIG. 11 is a graph showing $H_2O_2$ production by $A\beta$.

Because Aβ was observed to be covalently linked by Cu, the ability of the peptide to reduce metals and generate hydroxyl radicals was studied. The bathocuproine and bathophenanthroline reduced metal assay technique employed by Multhaup et al. was used in order to determine that APP itself possesses a $Cu^{2+}$ reducing site on its ectodomain (Multhaup, G., et al., *Science* 271:1406 (1996)). It has been discovered that Aβ possesses a striking ability to reduce both $Fe^{3+}$ to $Fe^{2+}$, and $Cu^{2+}$ to $Cu^+$, modulated by $Zn^{2+}$ and pH (6.6–7.4) (See FIG. 10). It is of great interest that the relative redox activity of the peptides studied correlates so well with their relative pathogenicity viz Aβ$_{1-42}$>Aβ$_{1-40}$>ratAβ in all redox assays studied. Since one of the caveats in using the reduced metals assay is that the detection agents can exaggerate the oxidation potential of $Cu^{2+}$ or Fe (III), other redox products were explored by assays where no metal ion indicators were necessary. It was discovered that hydrogen peroxide was rapidly formed by Aβ species (FIG. 11). Thus, Aβ produces both $H_2O_2$ and reduced metals whilst also binding zinc. Structurally, this is difficult to envisage for a small peptide, but we have recently shown that Aβ is dimeric in physiological buffers. Since $H_2O_2$ and reduced metal species are produced in the same vicinity, these reaction products are liable to produce the highly toxic hydroxyl radical by Fenton chemistry, and the formation of hydroxyl radicals from these peptides has now been shown with the thiobarbituric acid assay. The formation of hydroxyl radicals correlates with the covalent polymerization of the peptide (FIG. 9) and can be blocked by hydroxyl scavengers. Thus the concentrations of Fe, Cu, Zn & $H^+$ in the brain interstitial milieu could be important in facilitating precipitation and neurotoxicity for Aβ by direct (dimer formation) and indirect ($Fe^{2+}$/Cu and $H_2O_2$ formation) mechanisms.

Figure 6:
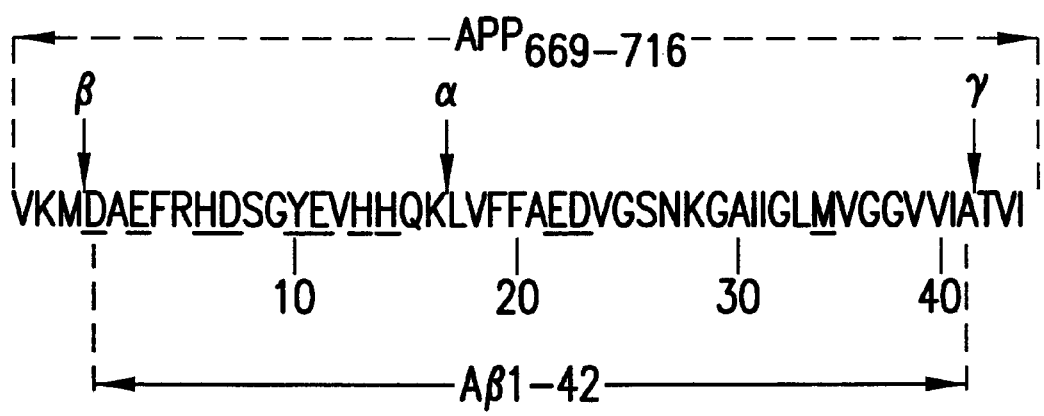
FIG. 6 shows the amino acid sequence of $APP_{669-716}$ near $A\beta_{1-42}$. Rat $A\beta$ is mutated (R5G, Y10F, H13R; bold). Possible metal-binding residues are underlined.
Figure 7:
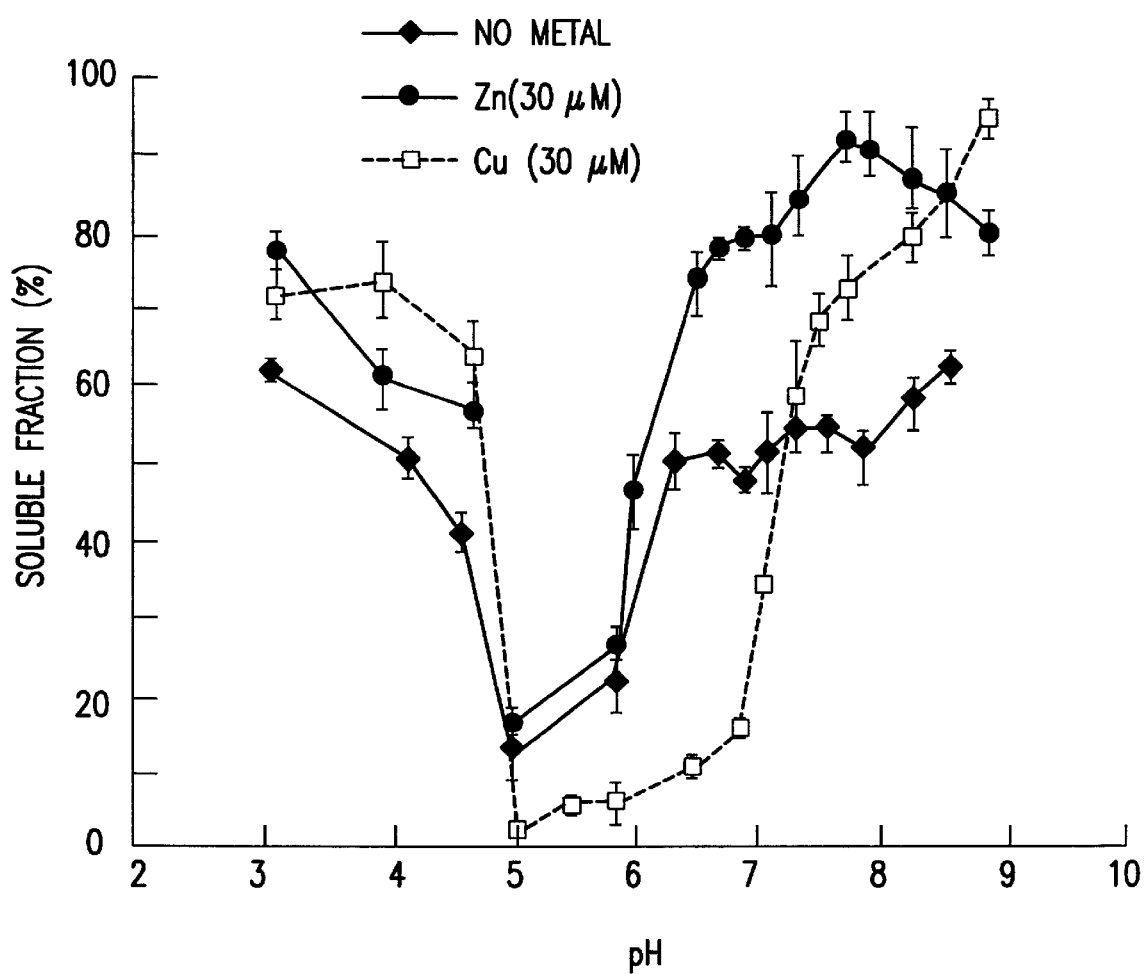
FIG. 7 is a graph showing the effects of pH, $Zn^{2+}$ or $Cu^{2+}$ upon $A\beta$ deposit formation.

$H_2O_2$ production by Aβ explains the mechanism by which $H_2O_2$ has been described to mediate neurotoxicity (Behl, C. et al., *Cell* 77:827 (1994)), previously thought to be the product of cellular overproduction alone. Interestingly, the scrambled Aβ peptide (same size and residue content as FIG. 6) produces appreciable $H_2O_2$ but no hydroxyl radicals. This is because the scrambled Aβ peptide is unable to reduce metal ions. This leads to the conclusion that what makes Aβ such a potent neurotoxin is its capacity to produce both reduced metals and $H_2O_2$ at the same time. This "double whammy" can then produce hydroxyl radicals by the Fenton reaction, especially if the $H_2O_2$ is not rapidly removed from the vicinity of the peptide. Catalase and glutathione peroxidase are the principal means of catabolizing $H_2O_2$, and their levels are low in the brain, especially in AD, perhaps explaining the propensity of Aβ to accumulate in brain tissue.

FIG. 11 shows that the production of $H_2O_2$ is oxygen dependent, and further investigation has indicated that Aβ can spontaneously produce the superoxide radical ($O_2^-$) in the absence of metal ions. This property of Aβ is particularly exaggerated in the case of Aβ$_{1-42}$, probably explaining why this peptide is more neurotoxic and more enriched than Aβ$_{1-40}$ in amyloid. $O_2^-$ generation will be subject to spontaneous dismutation to generate $H_2O_2$, however, this is a relatively slow reaction, although it may account for the majority of the $H_2O_2$ detected in our Aβ assays. $O_2^-$ is reactive, and the function of superoxide dismutase (SOD) is to accelerate the dismutation to produce $H_2O_2$ which is then catabolized by catalase and peroxidases into oxygen and water. The most abundant form of SOD is Cu/Zn SOD, mutations of which cause another neurodegenerative disease, amyotrophic lateral sclerosis (Rosen, D., et al, *Nature* 364:362 (1993)). Since Aβ, like Cu/Zn SOD, is a dimeric protein that binds Cu and Zn and reduces $Cu^{2+}$ and $Fe^{3+}$, we studied the $O_2^-$ dismutation behavior of Aβ in the µsec time-scale using laser pulse photolysis. These experiments have shown that Aβ exhibits Fe/Cu-dependent SOD-like activity with rate constants of dismutation at ≈$10^8$ $M^{-1}$ $sec^{-1}$, which are strikingly similar to SOD. Hence, Aβ appears to be a good candidate to possess the same function as SOD, and therefore may function as an antioxidant. This may explain why oxidative stresses cause it to be released by cells (Frederikse, P. H., et al., *Journal of Biological Chemistry* 271: 10169 (1996)). However, if $A\beta_{1-42}$ is involved in the reaction to oxidative stress, or if the $H_2O_2$ clearance is compromised at the cellular level, $A\beta$ will accumulate, recruiting more $O_2$ and producing more $O_2^-$ leading to a vicious cycle and localizing tissue peroxidation damage and protein cross-linking.

Example 3

Therapeutic Agents for Inhibition of Metal-Mediated Production of Reactive Oxygen Species Materials and Methods a) Synthesis of Peptides Synthetic $A\beta$ peptides $A\beta_{1-40}$ and $A\beta_{1-42}$ were synthesized by the W. Keck Laboratory, Yale, Conn. In order to verify the reproducibility of the data obtained with these peptides, confirmatory data were obtained by reproducing experiments with these $A\beta$ peptides synthesized and obtained from other sources: Glabe laboratory, University of California, Irvine, Calif., Multhaup Laboratory, University of Heidelberg, U.S. Peptides, Bachem, and Sigma. Rat $A\beta$ was synthesized and characterized by the Multhaup Laboratory, University of Heidelberg. $A\beta_{1-28}$ was purchased from U.S. Peptides, Bachem, and Sigma. $A\beta$ peptide stock solutions were prepared in chelex-100 resin (BioRad) treated water and quantified.

b) Metal Reduction Assay

The metal reduction assay was performed using a 96-well microtiter plate (Costar) based upon a modification of established protocols (Landers, J. W., et al., *Amer. Clin. Path.* 29:590 (1958); Landers, J. W., et al., *Clinica Chimica Acta* 3:329 (1958)). Polypeptides (10 μM) or Vitamin C (100 μM), metal ions (10 μM, $Fe(NO_3)_3$ or $Cu(NO_3)_2$), and reduced metal ion indicators, bathophenanthrolinedisulfonic acid (BP, for $Fe^{2+}$, Sigma, 200 μM) or bathocuproinedisulfonic acid (BC, for $Cu^+$, Sigma, 200 RM), were coincubated in phosphate buffered saline (PBS), pH 7.4, for 1 hr at 37° C. The metal ion solutions were prepared by direct dilution in the buffer from their aqueous stocks purchased from National Institute of Standards and Technology (NIST). Absorbencies were then measured at 536 nm ($Fe^{2+}$-BP complex) and 483 nm ($Cu^+$-BC complex), respectively, using a 96-well plate reader (SPECTRAmax 250, Molecular Devices, Calif.). In control samples, both metal ion and indicator were present to determine the background buffer signal. As a further control, both metal ion and peptide were present in the absence of indicator to estimate the contribution of light scattering due to turbidity to the absorbencies reading at these wavelengths. The net absorbances ($\Delta A$) at 536 nm or 483 nm were obtained by deducting the absorbencies from these controls from the absorbencies generated by the peptide and metal in the presence of the respective indicator.

The concentrations of reduced metal ions ($Fe^{2+}$ or $Cu^+$) were quantified based on the formula: $Fe^{2+}$ or $Cu^+$ $(\sim M)=A*10^6/(L*M)$, where L is the measured equivalent vertical pathlength for a well of 300 μL volume as described in the instrument's specifications manual (0.856 cm for $Fe^{2+}$; 1.049 cm for $Cu^+$); M is the known molecular absorbance ($M^{-1}$ $cm^{-1}$) which is 7124 (for $Fe^{2+}$-BP complex) or 2762 (for $Cu^+$-BC complex).

c) $H_2O_2$ Assay

The $H_2O_2$ assay was performed in a UV-transparent 96-well microtiter plate (Molecular Devices, Calif.), according to a modification of an existing protocol (Han, J. C., et al., *Anal. Biochem.* 234:107 (1996); Han et al., *Anal. Biochem.* 220: 5–10 (1994)). Polypeptides (10 μM) or Vitamin C (10 μM), $Fe^{3+}$ or $Cu^{2+}$ (1 μM) and a $H_2O_2$ trapping agent-Tris(2-Carboxyethyl)Phosphine hydrochloride (TCEP, Pierce, 50 μLM)-were co-incubated in PBS buffer (300 AL), pH 7.4, for 1 hour at 37° C. Under identical conditions, catalase (Sigma, 100 U/mL) was substituted for the polypeptides, to serve as a control signal representing 0 μM $H_2O_2$. Following incubation, the unreacted TCEP was detected by 5,5-Dithio-bis(2-Nitrobenzoic acid) (DTNB, Sigma, 50 KLM) which generates 2 moles of the colored product. The reactions are:

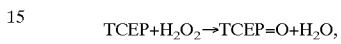

$TCEP+H_2O_2 \rightarrow TCEP=O+H_2O$, then the remaining TCEP is reacted with DTNB:

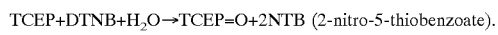

$TCEP+DTNB+H_2O \rightarrow TCEP=O+2NTB$ (2-nitro-5-thiobenzoate).

The amount of $H_2O_2$ produced was quantified based on the formula: $H_2O_2$ $(\mu M)=hA* 106/(2*L*M)$, where hA is the absolute absorbance difference between a sample and catalase-only control at 412 nm wavelength; L=0.875 cm, the equivalent vertical pathlength obtained from the platereader manufacturer's specifications; M is the molecular absorbance for NTB (14150 $M^{-1}$ $cm^{-1}$ at 412 nm).

TCEP is a strong reducing agent, and, hence, will artifactually react with polypeptides that contain disulfide bonds. This was determined not to be a source of artifact for the measurement of $H_2O_2$ generation from $A\beta$, which does not possess a disulfide bond.

d) Estimation of $O_2^-$

The spectrophotometric absorption peak for $O_2^-$ is 250 nm where its extinction coefficient is much greater than that of $H_2O_2$ (Bielski et al., *Philos Trans R Soc Lond B Biol Sci.* 311: 473–482 (1985)). The production of $O_2^-$ was estimated by measuring the spectrophotometric absorption of polypeptides (10 μM, 300 μL) after incubation for one hour in PBS, pH 7.4, at 37° C., using a 96-well plate reader. The corresponding blank was the signal from PBS alone. An absolute baseline for the signal generated by the peptide was not achievable in this assay since the absorption peak for tyrosine (residue 10 of $A\beta$) is close (254 nm) to the absorption peak for $O_2^-$. However, attenuation of the absorbance by co-incubation with superoxide dismutase (100 U/mL) indicated that the majority of the absorbance signal was due to the presence of $O_2^-$.

e) Thiobarbituric Acid Reaction Substance (TBARS) Assay—OH•

The Thiobarbituric Acid-Reactive Substance (TBARS) assay for incubation mixtures with $Fe^{3+}$ or $Cu^{2+}$ was performed in a 96-well microtiter format modified from established protocols (Gutteridge et al. *Biochim. Biolphys. Acia* 759: 38–41 (1983)). $A\beta$ peptide species (10 μM) or Vitamin C (100 μM), were incubated with $Fe^{3+}$ or $Cu^{2+}$ (1 μM) and deoxyribose (7.5 mM, Sigma) in PBS, pH 7.4. Following incubation (37° C., 1 hour), glacial (17 M) acetic acid and 2-thiobarburic acid (1%, w/v in 0.05 M NaOH, Sigma) were added and heated (100° C., 10 min). The final mixtures were placed on ice for 1–3 minutes before absorbencies at 532 nm were measured. The net absorbance change for each sample were obtained by deducting the absorbance from a control sample consisting of identical chemical components except for the Vitamin C or $A\beta$ peptides.

Results and Discussion

Oxygen radical involvement in human aging, the predominant risk factor for Alzheimer's disease (AD), was first proposed by Harman in 1956 (Harman, D., *J. Gerontol.* 11:298 (1956)) and increasing evidence has implicated oxidative stress in the pathogenesis of AD. Apart from metabolic signs of oxidative stress in AD-affected neocortex such as increased glucose-6-phosphate dehydrogenase activity (Martins, R. N., et al., *J. Neurochem.* 46:1042–1045 (1986)) and increased heme oxygenase-1 levels (Smith, M. A., et al., *Am. J. Pathol.* 145:42 (1994)), there are also numerous signs of oxygen radicalmediated chemical attack 5uch as increased protein and free carbonyls (Smith, C. D., et al., *Proc. Natl. Acad. Sci. USA* 88:10540 (1991); Hensley, K., et al., *J. Neurochem.* 65:2146 (1995); Smith, M. A., et al., *Nature* 382:120 (1996)), lipid peroxidation adducts (Palmer, A. M. & Burns, M. A., *Brain Res.* 645:338 (1994); Sayre, L. M. et al., *J. Neurochem.* 68:2092 (1997)), peroxynitrite-mediated protein nitration (Good, P. F., et al., *Am. J. Pathol.* 149:21 (1996); Smith, M. A., et al., *Proc. Natl. Acad. Sci. USA* 94:9866 (1997)), and mitochondrial and nuclear DNA oxidation adducts (Mecocci, P., et al., *Ann. Neurol.*, 34:609–616 (1993); Mecocci, P., et al., *Ann. Neurol.*, 36:747–751 (1994)). Recently, treatment of individuals with the antioxidant vitamin E has been reported to delay the progression of clinical AD (Sano, M. et al., *N. Engl. J. Med.* 336:1216 (1997)).

A relationship seems likely to exist between the signs of oxidative stress and the characteristic $A\beta$ collections (Glenner, G. G. & Wong, C., *Biochem. Biophys. Res. Commun.* 120:885 (1984)) found in the cortical interstitium and cerebrovascular intima media in AD. The brain regional variation of oxidation biomarkers corresponds with amyloid plaque density (Hensley, K., et al., *J. Neurochem.* 65:2146 (1995)). Indeed, neurons cultured from subjects with Down's syndrome, a condition complicated by the invariable premature deposition of cerebral $A\beta$ (Rumble, B., et al., *N. Engl. J. Med.* 320:1446 (1989)) and the overexpression of soluble $A\beta_{1-42}$ in early life (Teller, J. K., et al., *Nature Medicine* 2:93 (1996)), exhibit lipid peroxidation and apoptotic cell death caused by increased generation of hydrogen peroxide (Busciglio, J. & Yankner, B. A., *Nature* 378:776 (1995)). Synthetic $A\beta$ peptides have been shown to induce lipid peroxidation of synaptosomes (Butterfield, D. A., et al., *Biochem. Biophys. Res. Commun.* 200:710 (1994)), and to exert neurotoxicity (Behl, C., et al., *Cell* 77:817 (1994); Mattson, M. P., et al., *J. Neurochem.* 65:1740 (1995)) or vascular endothelial toxicity through a mechanism that involves the generation of cellular superoxide/hydrogen peroxide ($O_2^-/H_2O_2$) and is abolished by the presence of SOD (Thomas, T., et al., *Nature* 380:168 (1996) or catalytic synthetic $O_2^-/H_2O_2$ scavengers (Bruce, A. J., et al., *Proc. Natl. Acad. Sci. USA* 93:2312 (1996). Antioxidant vitamin E and the spin-trap compound PBN have been shown to protect against $A\beta$-mediated neurotoxicity in vitro (Goodman, Y., & Mattson, M. P., *Exp. Neulrol.* 128:1 (1994); Harris, M. E., et al, *Exp. Neurol.* 131:193 (1995)).

$A\beta$, a 39–43 amino acid peptide, is produced (Haass, C., et al., *Nature* 359:322 (1992); Seubert, P., et al., *Nature* 359:325 (1992); Shoji, M., et al., *Science* 258:126 (1992)) by constitutive cleavage of the amyloid protein precursor (APP) (Kang, J., et al., *Nature* 325:733 (1987); Tanzi, R. E., et al., Nature Genet (1993)) as a mixture of polypeptides manifesting carboxyl-terminal heterogeneity. $A\beta_{1-40}$ is the major soluble $A\beta$ species in biological fluids (Vigo-Pelfrey, C., et al., *J. Netrochem.* 61:1965 (1993)) and $A\beta_{1-42}$ is a minor soluble species, but is heavily enriched in interstitial plaque amyloid (Masters, C. L., et al., *Proc. Natl. Acad. Sci. USA* 82:4245 (1985); Kang, J. et al., *Nature* 325:733 (1987); Prelli, F., et al., *J. Neurochem.* 51:648 (1988); Roher et al. *J. Cell Biol.* 107:2703–2716 (1988); Roher et al., *J. Neurochem.* 61:1916–1926 (1993); Miller, D. L,., et al., *Arch. Biochem. Biophys.* 301:41 (1993)). The discovery of pathogenic mutations of APP close to or within the $A\beta$ domain (van Broeckhoven, C., et al., *Science* 248:1120 (1990); Levy, E., et al., *Science* 248:1124 (1990); Goate, A., et al., *Nature* 349:704 (1991); Murrell, J., et al., *Science* 254:94 (1991); Mullan, M., et al., Nature Genet 1:345 (1992)) indicates that the metabolism of $A\beta$ is involved with the pathophysiology of this predominantly sporadic disease. Familial AD-linked mutations of APP, presenilin-1 and presenilin-2 correlate with increased cortical amyloid burden and appear to induce an increase in the ratio of $A\beta_{1-42}$ as part of their common pathogenic mechanism (Suzuki, N., et al., *Science* 264:1336 (1994); Scheuner et al., *Nat Med.*, 2(8):864–870 (1996); Citron, M., et al., *Nature Medicine* 3:67 (1997)). However, the mechanism by which $A\beta_{1-42}$ exerts more neurotoxicity than $A\beta_{1-40}$ and other $A\beta$ peptides (Doré, S., et al., *Proc. Natl. Acad. Sci. USA* 94:4772 (1997)) remains unclear.

One of the models proposed for $A\beta$ neurotoxicity is based on a series of observations of $A\beta$-generated oxyradicals generated by a putative $A\beta$ peptide fragmentation mechanism which is $O_2$-dependent, metal-independent and involves the sulfoxation of the methionine at $A\beta$ residue 35 (Butterfield, D. A., et al., *Biochem. Biophys. Res. Commun.* 200:710 (1994); Hensley, K., et al., *Proc. Natl. Acad. Sci. USA* 91:3270 (1994); Hensley, K., et al., *Ann N Y Acad Sci.*, 786: 120–134 (1996)). $A\beta_{25-35}$ peptide has been reported to exhibit $H_2O_2$-like reactivity towards aqueous $Fe^{2+}$, nitroxide spin probes, and synaptosomal membrane proteins (Butterfield, D. A., et al., *Life Sci.* 58:217 (1996)), and $A\beta_{40}$ has also been reported to generate the hydroxyl radical by mechanisms that are unclear (Tomiyama, T., et al., *J. Biol. Chem.* 271:6839 (1996)). However, there has been no quantitative appraisal of the ROS-generating capacity of $A\beta_{1-42}$ versus that of $A\beta_{1-40}$ and other $A\beta$ variants, to date.

$A\beta$ is a metal binding protein which saturably binds zinc via a histidine-mediated specific high affinity site ($K_D$=107 nM) as well as by low affinity binding ($K_D$=5.2 $\mu$M). The high-affinity zinc binding site was mapped to a stretch of contiguous residues between positions 6–28 of the $A\beta$ sequence (Bush, A. I., et al., *J. Biol. Chem.* 269:12152 (1994)). Concentrations of zinc$\geq$1 gM rapidly induce aggregation of human $A\beta_{1-40}$ solutions (Bush, A. I., et al., *Science* 265:1464 (1994)), in reversible manner which is dependent upon the dimerization of peptide in solution, its alpha-helical content, and the concentration of NaCl (Huang, X., et al., *J. Biol. Chem.* 272:26464–26470 (1997)). Rat/mouse $A\beta_{1-40}$ ("rat $A\beta$", with substitutions o $R_5 \rightarrow G$, $Y_{10} \rightarrow F$, and $H_{13} \rightarrow R$, as compared to human $A\beta$) binds zinc less avidly (a single binding site, $K_A$=3.8 $\mu$M) and, unlike the human peptide, is not precipitated by zinc at concentrations$\leq$25 $\mu$M. Since zinc is concentrated in the neocortex, we hypothesized that the differential solubility of the rat/mouse $A\beta$ peptide in the presence of zinc may explain the scarcity with which these animals form cerebral $A\beta$ deposits (Johnstone, E. M., et al., *Mol. Brain Res.* 10:299 (1991); Shivers, B. D., et al., *EMBO J.* 7:1365 (1988)).

We have also observed interactions of $A\beta$ with $Cu^{2+}$, which stabilizes dimerization of $A\beta_{1-40}$ on gel chromatography (Bush, A. I., et al., *J. Biol. Chem.* 269:12152 (1994)), and which binds to the peptide with an affinity estimated to be in the low picomolar range. $Fe^{2+}$ has been observed to induce partial aggregation of $A\beta$ (Bush, A. I., et al., *Science* 268:1921 (1995)), and to induce SDS-resistant polymerization of the peptide (Dyrks, T., et al., *J. Biol. Chem.*

267:18210–18217 (1992)). We hypothesized that the interactions of Aβ with Fe and Cu may contribute to the genesis of the oxidation insults that are observed in the AD-affected brain. This is because $Fe^{3+}$ and $Cu^{2+}$ are redox-active metal ions that are concentrated in brain neurons, and may participate in the generation of ROS by transferring electrons in their reduced state (reviewed in Markesbery, 1997).

The levels of Cu and Fe, and their binding proteins, are dysregulated in AD (Diebel, M. A., et al., *J. Neurol. Sci.* 143:137 (1996); Good, P. F., et al., *Ann. Neurol.* 31:286 (1992); Robinson, S. R., et al., *Alzheimer's Research* 1:191 (1995); Thompson, C. M., et al., *Neuroloxicology* 9:1 (1988); Kennard, M. L., et al., *Nature Medicine* 2:1230 (1996); Connor, J. R., et al., Neurosci. Lett. 159:88 (1993)) and may therefore lead to conditions that could promote ROS production. While a direct role for Aβ in metal-dependent ROS generation has not been described, the peptide's physiochemical interation with transition metals, the presence of ferritin (Grudke-lqbal, I., et al., *Acta Neuropathol.* 81:105 (1990)) and redox reactive iron (Smith, M. A., et al., *Proc. Natl. Acad. Sci. USA* 94:9866 (1997)) in amyloid lesions, and the facilitation of $A\beta_{1-40}$ neurotoxicity in cell culture by nanomolar concentrations of iron (Schubert, D. & Chevion, M., *Biochem. Biophys. Res. Commun.* 216:702 (1995)), collectively support such a possibility.

We report the simultaneous production of $H_2O_2$ and reduced metal ions by Aβ, with the consequent generation of the hydroxyl radical. The amounts of reduced metal and ROS were both greatest when generated by $A\beta_{1-42} > A\beta_{1-40} >> $ rat $A\beta_{1-40}$, $A\beta_{1-40}$ and $A\beta_{1-28}$, a chemical relationship that correlates with the relative neurotoxicity of these peptides. These data describe a novel, $O_2^-$ and biometal-dependent pathway of ROS generation by Alzheimer Aβ peptides which may explain the occurrence of oxidative stress in AD brain.

a) Metal Ion Reduction by Aβ Peptides

Figure 13B:
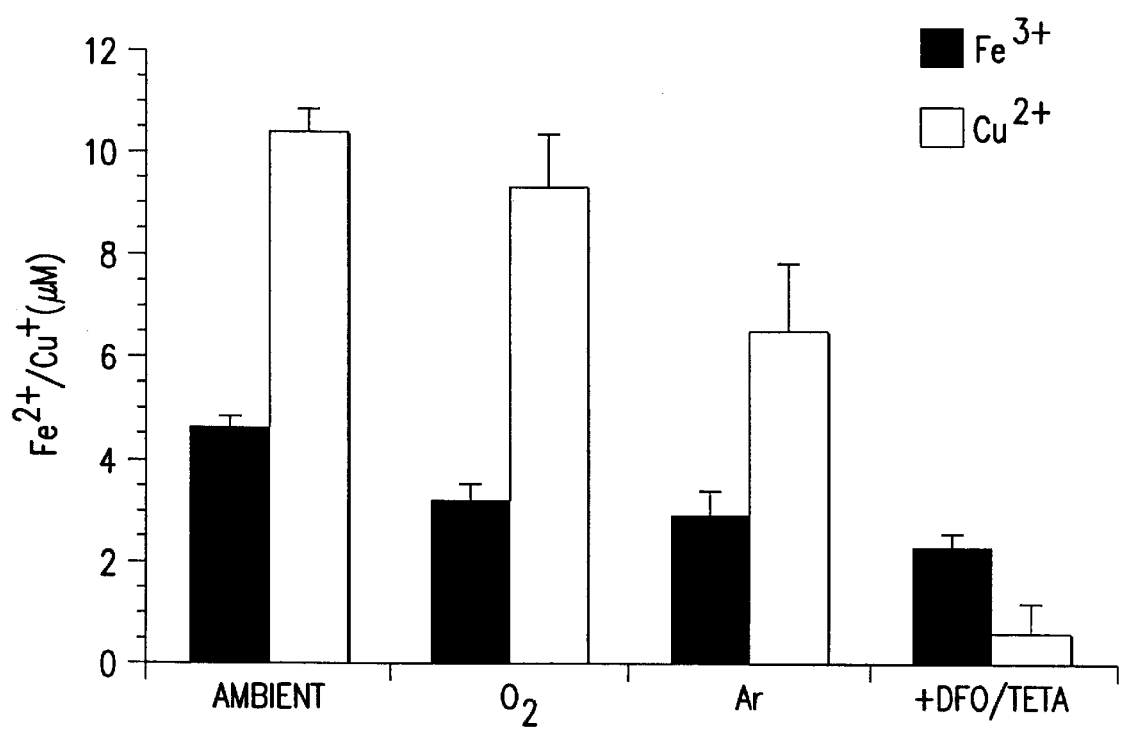

To determine whether Aβ peptides possess metal-reducing properties, the ability of Aβ peptides (Example 1) to reduce $Fe^{3+}$ and $Cu^{2+}$, compared to Vitamin C and other polypeptides (Example 2) was measured. Vitamin C, serving as a positive control, reduced $Cu^{2+}$ efficiently (FIG. 13A). However, the reduction of $Cu^{2+}$ by $A\beta_{1-42}$ was as efficient, reducing all of the available $Cu^{2+}$ during the incubation period. $A\beta_{1-40}$ reduced 60% of the available $Cu^{2+}$, whereas rat $A\beta_{1-40}$ and $A\beta_{1-28}$ reduced no $Cu^{2+}$. The reduction of $Cu^{2+}$ by BSA (25%) and insulin (10%) was less efficient than that by the human Aβ peptides, and was not unexpected since these polypeptides possess cysteine residues and reduce $Cu^{2+}$ in the process of forming disulfide bonds.

$Fe^{3+}/Fe^{2+}$ has lower standard reduction potential (0.11 V) than $Cu^{2+}/Cu^+$ (0.15 V) does under our experimental conditions (Miller, D. M., et al., Free *Radical Biology & Medicine* 8:95 (1990)), and, in general, $Fe^{3+}$ was reduced with less efficiency by Vitamin C and the polypeptides that reduced $Cu^{2+}$. Vitamin C reduced 15% of the available $Fe^{3+}$, however $A\beta_{1-42}$ was the most efficient (50%) of the agents tested for $Fe^{3+}$ reduction, reducing more $Fe^{3+}$ in the incubation period than Vitamin C (15%), $A\beta_{1-40}$ (12%) and BSA (8%). Rat $A\beta_{1-40}$, $A\beta_{1-28}$ and insulin did not significantly facilitate the reduction of $Fe^{3+}$. Analysis of $A\beta_{1-42}$ and $A\beta_{1-40}$ after incubation with $Cu^{2+}$ and $Fe^{3+}$ under these conditions revealed that there was no apparent mass modification of the peptides on mass spectrometry, and no change in its migration pattern on sodium dodecyl sulfate polyacrylamide gel electrophoresis (SDS PAGE), nor evidence for increased aggregation of the peptides by turbidometry or sedimentation analysis, suggesting that the peptides were not consumed or modified during the reduction reaction. Under these conditions, the complete kinetics of the peptide-mediated reactions cannot be appreciated (the presence of $A\beta_{1-42}$ induced the total consumption of the $Cu^{2+}$ substrate within the incubation period), but a striking relationship exists between the relative efficiencies of the various Aβ peptides to reduce $Cu^{2+}/Fe^{3+}$ in this system and their respective participation in amyloid neuropathology.

Since the dissolved $O_2$ in the buffer vehicle may be expected to react with the reduced metals being generated [Reaction (1)], the effect of modulating the $O_2$ tension in the buffer upon the generation of reduced metals by the Aβ peptides (FIG. 13B) was examined. Prior to the addition of Vitamin C or polypeptide, the buffer vehicle was continuously bubbled for 2 hours at 20° C. with 100% $O_2$ to create conditions of increased $O_2$ tension, or Argon to create anaerobic conditions. Increasing the $O_2$ tension slightly reduced the levels of reduced metals being detected, probably due to the diversion of a fraction of the $Fe^{2+}/Cu^+$ being generated to Reaction (1), and, if $H_2O_2$ is being produced as a product of Reaction (2), the recruitment of $Fe^{2+}/Cu^+$ into the Fenton reaction [Reaction (3)]. However, performing the reaction under anaerobic (Argon purged) conditions also slightly reduced the levels of reduced metals being detected. This may be because some of the reduction of $Fe^{3+}/Cu^{2+}$ is due to reaction with $O_2^-$:

$$M^{(n+1)+} + O_2^- \rightarrow M^{n+} + O_2 \qquad \text{Reaction (5)}$$

To determine whether the reduction of metal ions in the presence of Aβ was due to the action of the peptide or the generation of $O_2^-$ by the peptide, the effects of metal ion chelators on the generation of reduced metal ions (FIG. 13B) was studied. It was found that coincubation of $A\beta_{1-42}$ with the relatively $Fe^{3+}$-specific chelator desferrioxamine (DFO) under ambient oxygenation conditions nearly halved the production of $Fe^{2+}$. Coincubation of $A\beta_{1-42}$ with the high-affinity $Cu^{2+}$ chelator TETA abolished 95% of the $Cu^+$ generated by the peptide under ambient oxygenation conditions. These data indicate that the majority of the $Cu^+$ and a significant amount of the $Fe^{2+}$ produced by $A\beta_{1-42}$ are due to the direct action of the peptide and not indirectly due to the production of $O_2^-$.

The inhibitory effects of chelation upon Aβ-mediated reduction of metal ions indicates that Aβ probably directly coordinates $Fe^{3+}$ and $Cu^{2+}$, and also that these chelating agents are not potentiating the redox potential of the metals ions, suggested to be an artifactual mechanism for the generation of reduced metal species (Sayre, L. M. et al., *Science* 274:1933 (1996)). The reasons for DFO being less effective than TETA in attenuating metal reduction may relate to the respective (unknown) binding affinities for $Fe^{3+}$ and $Cu^{2+}$ to the Aβ peptide, the stereochemistry of the coordination of the metal ions by the peptide, and the abilities of the chelating agents to affect electron transfer after coordinating the metal ion.

The reduction of metal ions by Aβ must leave the peptide, at least transiently, radicalized, in agreement with the electron paramagnetic resonance (EPR) findings of lensley et al., *Proc. Natl. Acad. Sci.* 91:3270 (1994). In their report, DFO, EDTA or Chelex 100 could not abolish the EPR signal generated by $A\beta_{25-35}$ in PBS, leading these investigators to conclude that the radicalization of Aβ was metal-independent. However, the inventors have found that after treatment with Chelex 100 the concentrations of Fe and Cu in PBS are still as high as ≈0.5 μM (8), which could be sufficient to induce the radicalization of the peptide after metal reduction. Since DFO does not abolish the reduction of $Fe^{3+}$ by $A\beta_{1-42}$ (FIG. 13B), and since EDTA has been observed to potentiate Fe-mediated Fenton chemistry (Samuni et al., Eur. *J. Biochem.* 137:119–124(1983)), it is suspected that Hensley and colleagues may have inadvertently overlooked the contribution of metal reduction to $A\beta$-mediated radical formation.

Rat $A\beta_{1-40}$ did not reduce metal ions, and has been shown to have attenuated binding of $Zn^{2+}$ (Bush et al., *Science*, 265:1464 (1994)). A similar attenuation of $Cu^{2+}$ and $Fe^{3+}$ binding by rat $A\beta_{1-40}$ compared to human $A\beta_{1-40}$ is anticipated. These data also indicate that the rat $A\beta$ substitutions in human $A\beta$'s zinc binding domain towards the peptide's amino terminus (Bush et al., *J. Biol. Chem.*, 269:12152 (1994)) involve residues that mediate the metal-reducing properties of the peptide. However, the hydrophobic carboxyl-terminal residues were also critical to the reduction properties of $A\beta$. That $A\beta_{1-28}$ did not reduce metal ions indicates that an intact $Zn^{2+}$-binding site (Bush et al., *J. Biol. Chem.* 269:12152 (1994)) is insufficient to facilitate the metal reduction reaction. The mechanism by which the two additional hydrophobic residues (Ile and Ala) on $A\beta_{1-42}$ so substantially enhance the peptide's redox activity compared to $A\beta_{1-40}$ is still unclear.

It has been observed that sulfoxation of the methionine residue at $A\beta$ position 35 accompanies the EPR changes seen during the incubation of $A\beta_{25-35}$ for 3 hours in PBS at 37° C. (Hensley, K., et al., *Ann N Y Acad Sci.*, 786: 120–134 (1996)), however, no evidence was found for a modification of $A\beta_{1-40}$ and $A\beta_{1-42}$ after mass spectrophotometric examination of the peptides incubated under conditions as described. Therefore, $A\beta$-mediated metal reduction, and the subsequent $A\beta$-mediated redox reactions described below, appear to be achieved by a mechanism that differs from that previously reported.

b) Production of $H_2O_2$ by $A\beta$ Peptides

Figure 14A:
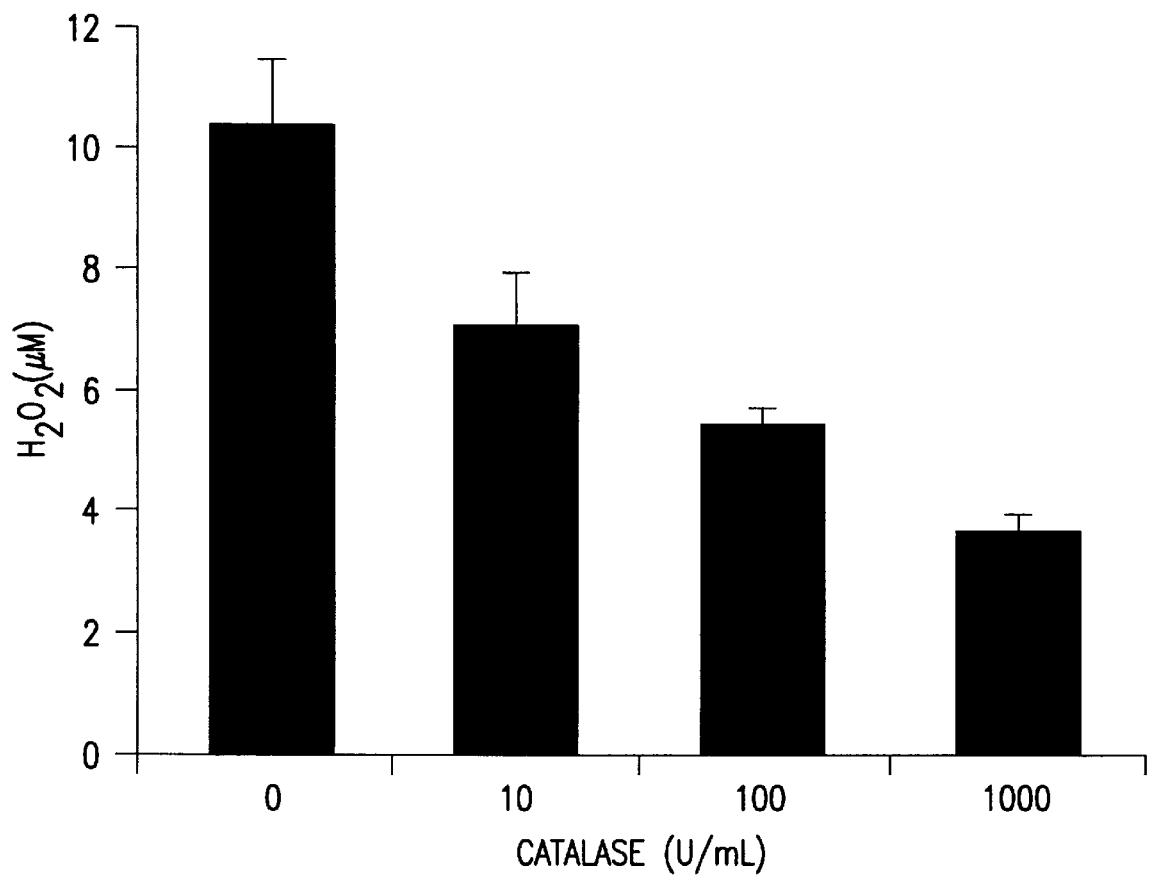
FIGS. 14A–14E are graphical representations showing production of $H_2O_2$ from the incubation of $A\beta$ in the presence of substoichiometric amounts of $Fe^{3+}$ or $Cu^{2+}$.
Figure 14B:
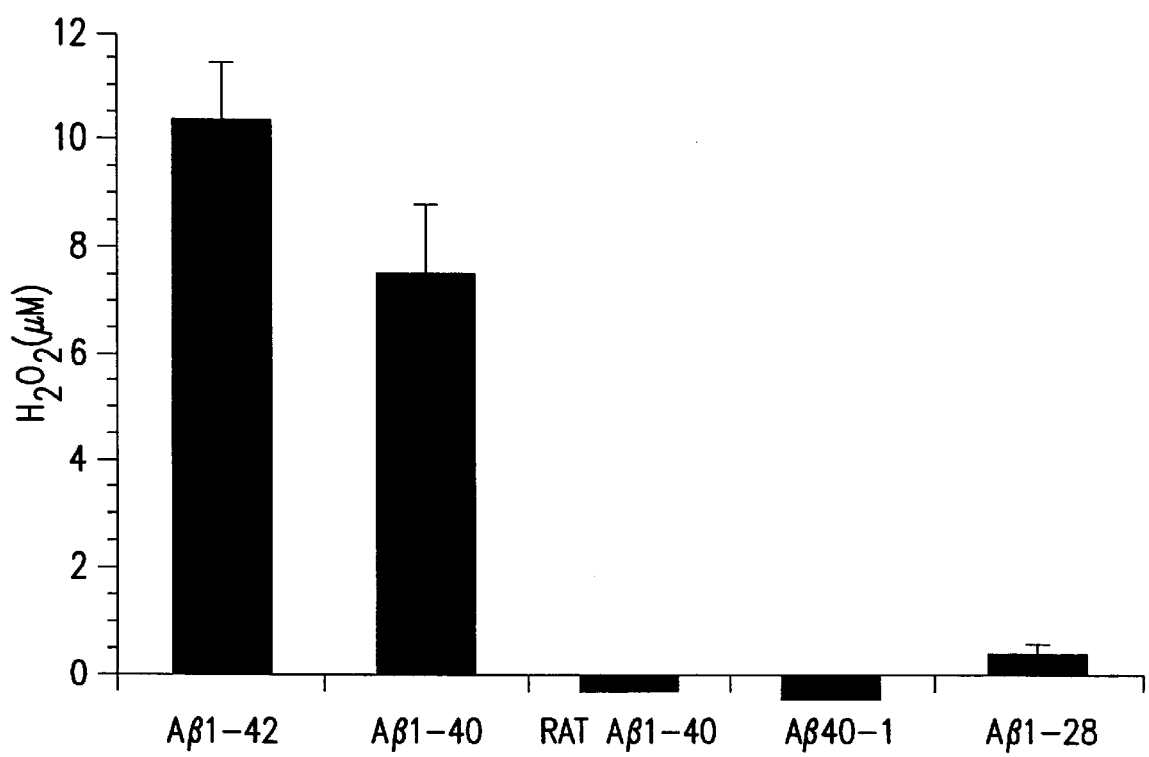

The reduced metal ions produced by $A\beta$ were expected to generate $O_2^-$ and $H_2O_2$ by Reactions (1) and (2). To study this, a novel assay was developed (Example 3) which detected the generation of 10 $\mu$M $H_2O_2$ by $A\beta_{1-42}$ in the presence of 1 $\mu$M $Fe^{3+}$ under ambient $O_2$ conditions (FIG. 14A). To validate the assay, coincubation with catalase was observed to abolish the $H_2O_2$ signal in a dose dependent manner. The amount of $H_2O_2$ produced by the various $A\beta$ peptides was studied, and observed that the order of the production of $H_2O_2$ by the $A\beta$ variants was $A\beta_{1-42} > A\beta_{1-40} >>$ rat $A\beta_{1-40} - A\beta_{1-28}$, (FIG. 14B), paralleling the amounts of metal reduction by the same peptides (FIG. 13A).

Figure 14C:
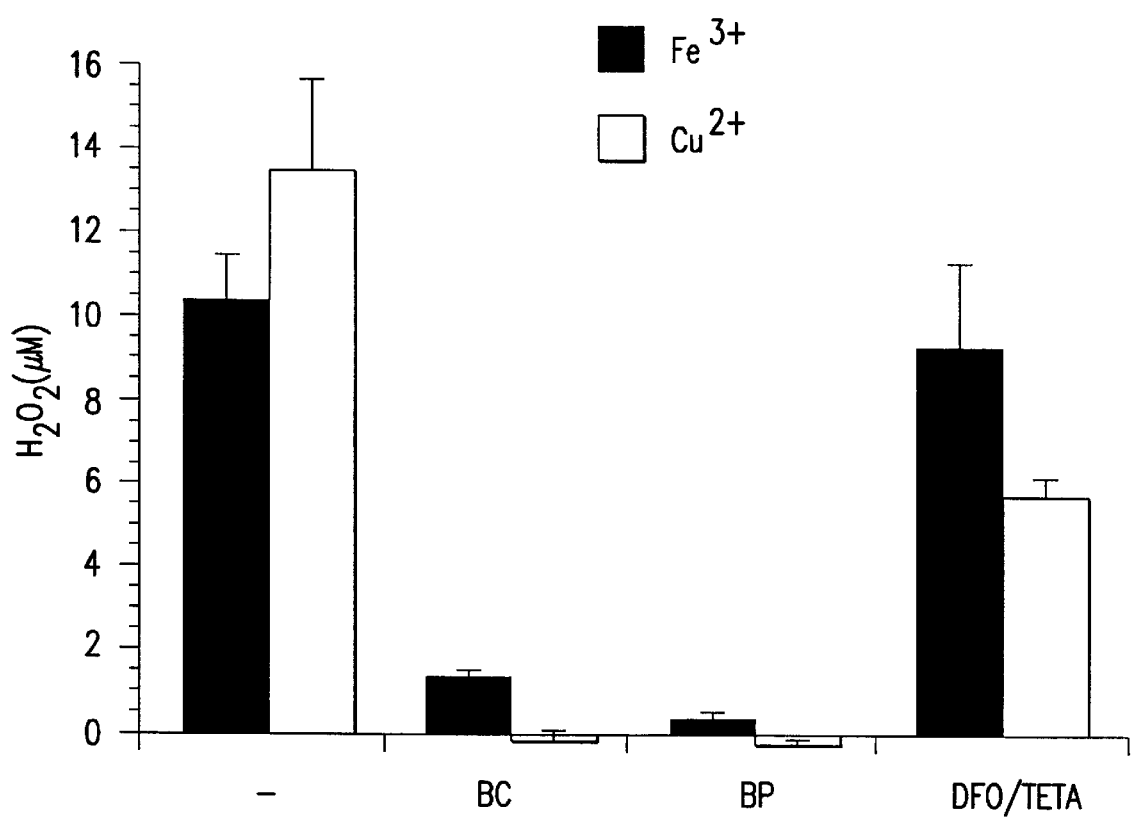

$H_2O_2$ formation is likely to be mediated first by $O_2$-dependent $O_2^-$ formation [Reaction (1)], followed by dismutation [Reaction (2)]. To appraise the contribution of Reaction (1) to $H_2O_2$ formation, $H_2O_2$ formation by $A\beta_{1-42}$ in the presence of chelators was measured (FIG. 14C). The amount of $H_2O_2$ formed in the presence of 1 $\mu$M $Cu^{2+}$ was 25% greater than the amount formed in the presence of 1 $\mu$M $Fe^{3+}$. Coincubation with DFO had no effect on $H_2O_2$ formation in the presence of 1 $\mu$M $Fe^{3+}$. However, TETA, and the $Cu^+$-specific indicator BC, both substantially inhibited the formation of $H_2O_2$ in the presence of 1 $\mu$M $Cu^{2+}$. The reasons why DFO partially inhibited $Fe^{3+}$ reduction, but was unable to inhibit $H_2O_2$ formation are unclear. These data indicate that the formation of $H_2O_2$ by $A\beta$ is dependent upon the presence of substoichiometric amounts of $Cu^+/(II)$. The possibility that formation of $H_2O_2$ in the presence of $Fe^{3+}$ was due to the presence of trace quantities of $Cu^{2+}$ cannot be excluded.

BC and BP, agents that specifically complex reduced metal ions, were far more effective than DFO and TETA at inhibiting $H_2O_2$ formation by $A\beta$ (FIG. 14C) but the reasons for this are not clear. The relatively $Fe^{2+}$-specific complexing agent, BP, inhibited $H_2O_2$ formation in the presence of $Cu^{2+}$, and the relatively $Cu^+$-specific complexing agent, BC, inhibited $H_2O_2$ formation in the present of $Fe^{3+}$, suggesting that these agents are not totally specific in their metal ion affinities. The formation of $H_2O_2$ by $A\beta$ in the absence of BC or BP confirms that the reduction of metals is not contingent upon the artifactual enhancement of the metal ions' redox potentials (Sayre, L. M., *Science* 274:1933 (1996)).

Figure 14D:
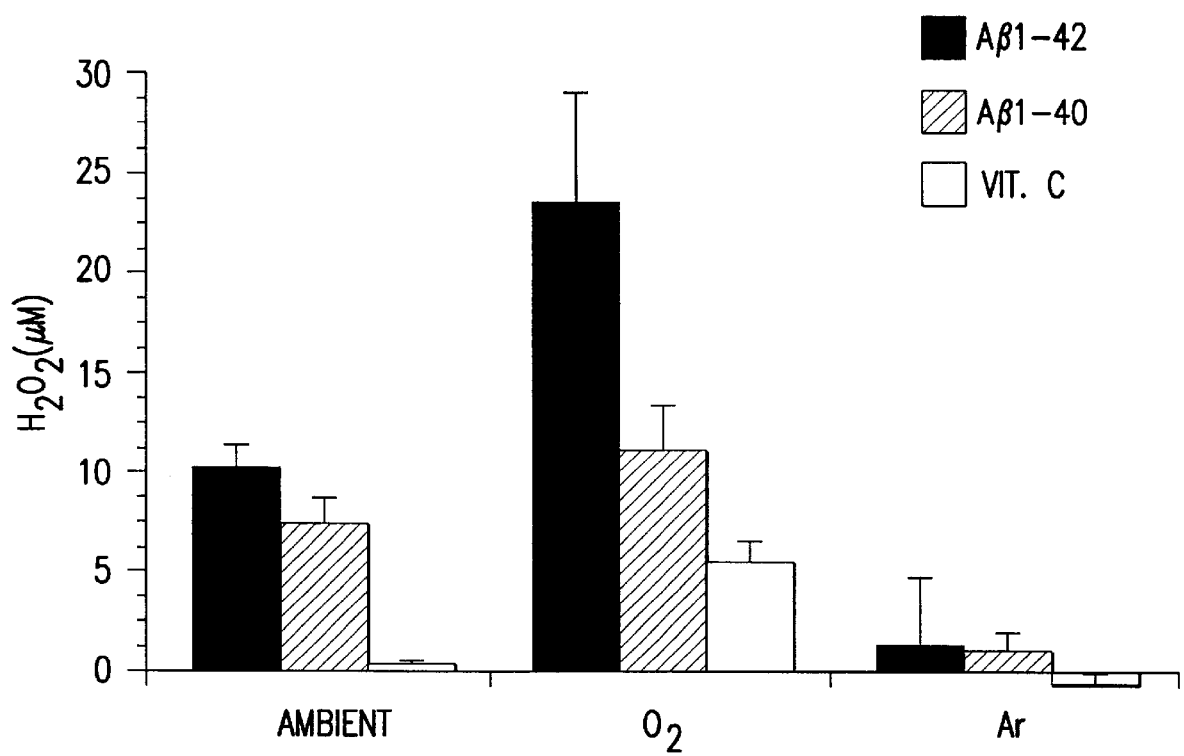
Figure 14E:
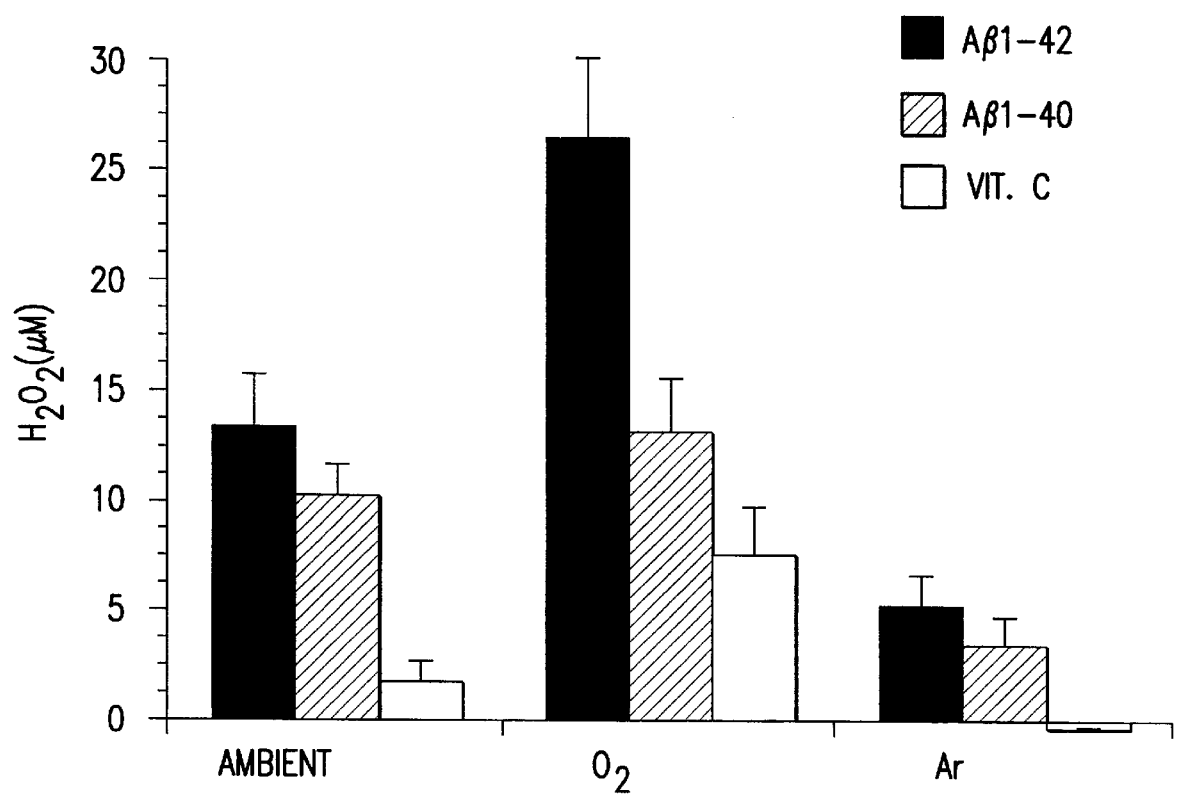

To determine whether the formation of $O_2^-/H_2O_2$ by $A\beta$ is merely due to the reduction of metal ions, or whether $A\beta$ also facilitates the recruitment of the substrates in Reaction (1), the generation of $H_2O_2$ by $A\beta_{1-42}$, $A\beta_{1-40}$ and Vitamin C under different $O_2$ tensions in the presence of 1 $\mu$M $Fe^{3+}$ (FIG. 14D) or 1 $\mu$M $Cu^{2+}$ (FIG. 14E) was studied. The presence of Vitamin C was used as a control measure to determine the amount $H_2O_2$ that is generated by the presence of reduced metals alone. In the presence of either metal ion, there was a significant increase in the amount of $H_2O_2$ produced under higher $O_2$ tensions. The presence of either $A\beta_{1-42}$ and $A\beta_{1-40}$ generated more $H_2O_2$ ($A\beta_{1-42} > A\beta_{1-40}$) than Vitamin C under any $O_2$ tension studied, and generated $H_2O_2$ under conditions where Vitamin C produced none, even though reduced metal ions must be present due to the activity of Vitamin C. Therefore, under these ambient and argon-purged conditions, the reduction of metal ions is insufficient to produce $H_2O_2$. These data indicate that $A\beta$ indeed facilitates the recruitment of $O_2$ into Reaction (1) more than would be expected by the interaction of the metals reduced by $A\beta$ with the passively dissolved $O_2$. Under relatively anaerobic conditions, the $A\beta$ peptides were observed to still produce $H_2O_2$ in the presence of $Cu^{2+}$ (FIG. 14E). This is probably due to the ability of $A\beta$ to recruit $O_2$ into Reaction (1) under conditions of very low $O_2$ tension. Since $O_2$ is preferentially dissolved in hydrophobic environments (Halliwell and Gutteridge, *Biochem. J.*, 219:1–14 (1984)), it seems that the hydrophobic carboxyl-terminus of $A\beta$ could attract $O_2$, serving as a reservoir for the substrate.

c) Evidence of the Superoxide Anion Formed by the $A\beta$ -metal Complex

Figure 15A:
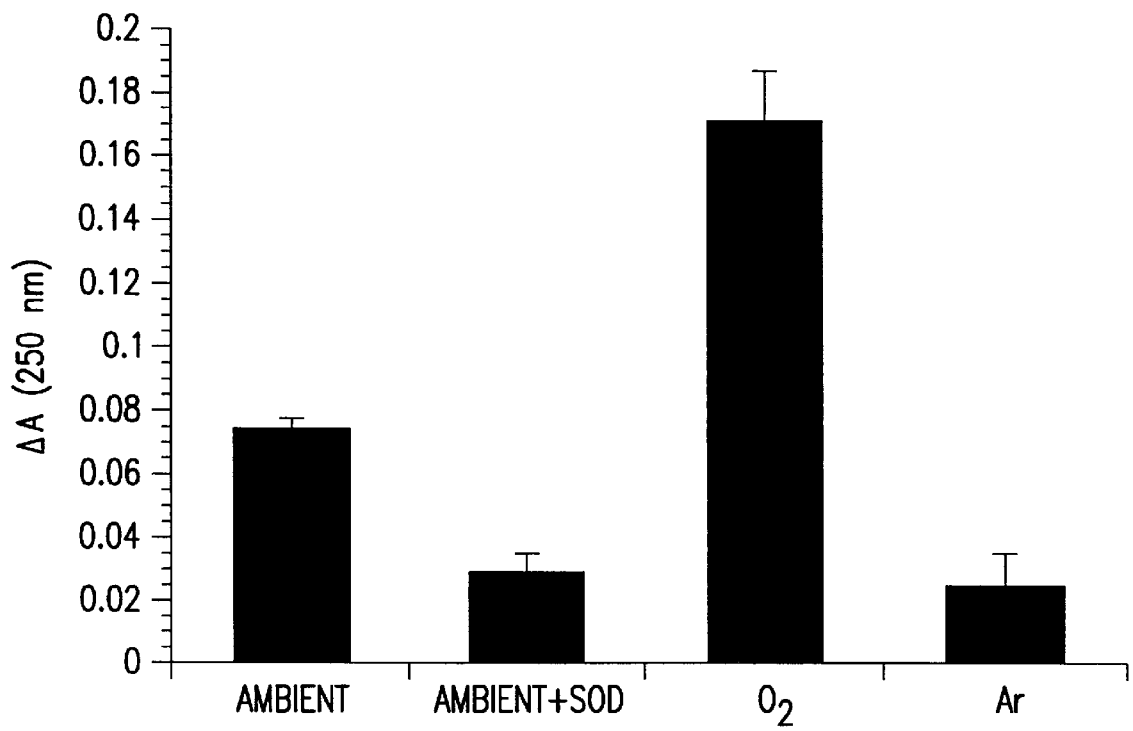
FIGS. 15A and 15B are graphical representations showing superoxide anion detection.

To confirm the production of $O_2^-$ by $A\beta$, the absorbance of the peptide in solution at 250 nm, the absorbance peak of $O_2^-$ (FIG. 15A) was measured. The absorbance generated by $A\beta_{1-42}$ in the presence of 1 $\mu$M $Fe^{3+}$ was 60% reduced when co-incubated with SOD, increased in the presence of high $O_2$ tension and abolished under anaerobic conditions. These data support the likelihood that $A\beta$ generates $H_2O_2$ by first generating $O_2^-$.

Figure 15B:
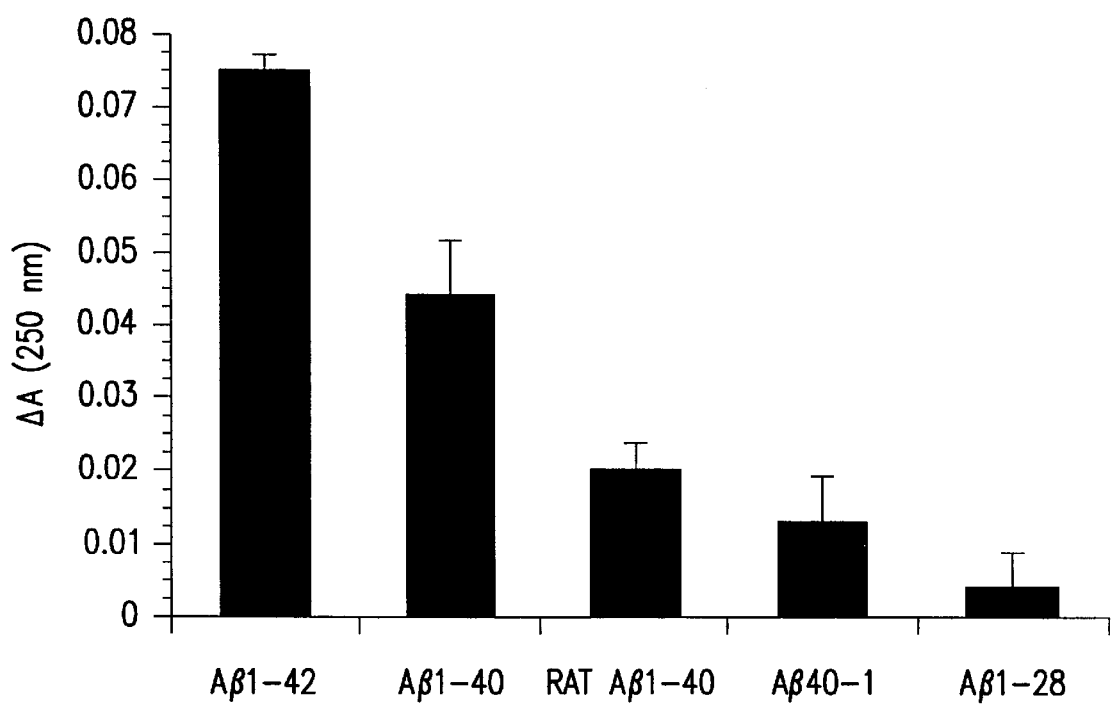

The absorbance changes at 250 nm for the various $A\beta$ peptides in PBS (FIG. 15B) paralleled the production of $H_2O_2$ from the same peptides (FIG. 14B), but the reason for the $A_{250}$ being much greater for $A\beta_{1-42}$ compared to $A\beta_{1-40}$ is unclear. It is likely that a fraction of the total $H_2O_2$ generated by $A\beta$ is decomposed by the Fenton reaction [Reaction (3)]. Therefore, the amount of $H_2O_2$ detected may be an attenuated reflection of the amount of $O_2^-$ detected.

d) Detection of Hydroxyl Radicals Generated from the $A\beta$-metal Complex

Figure 16A:
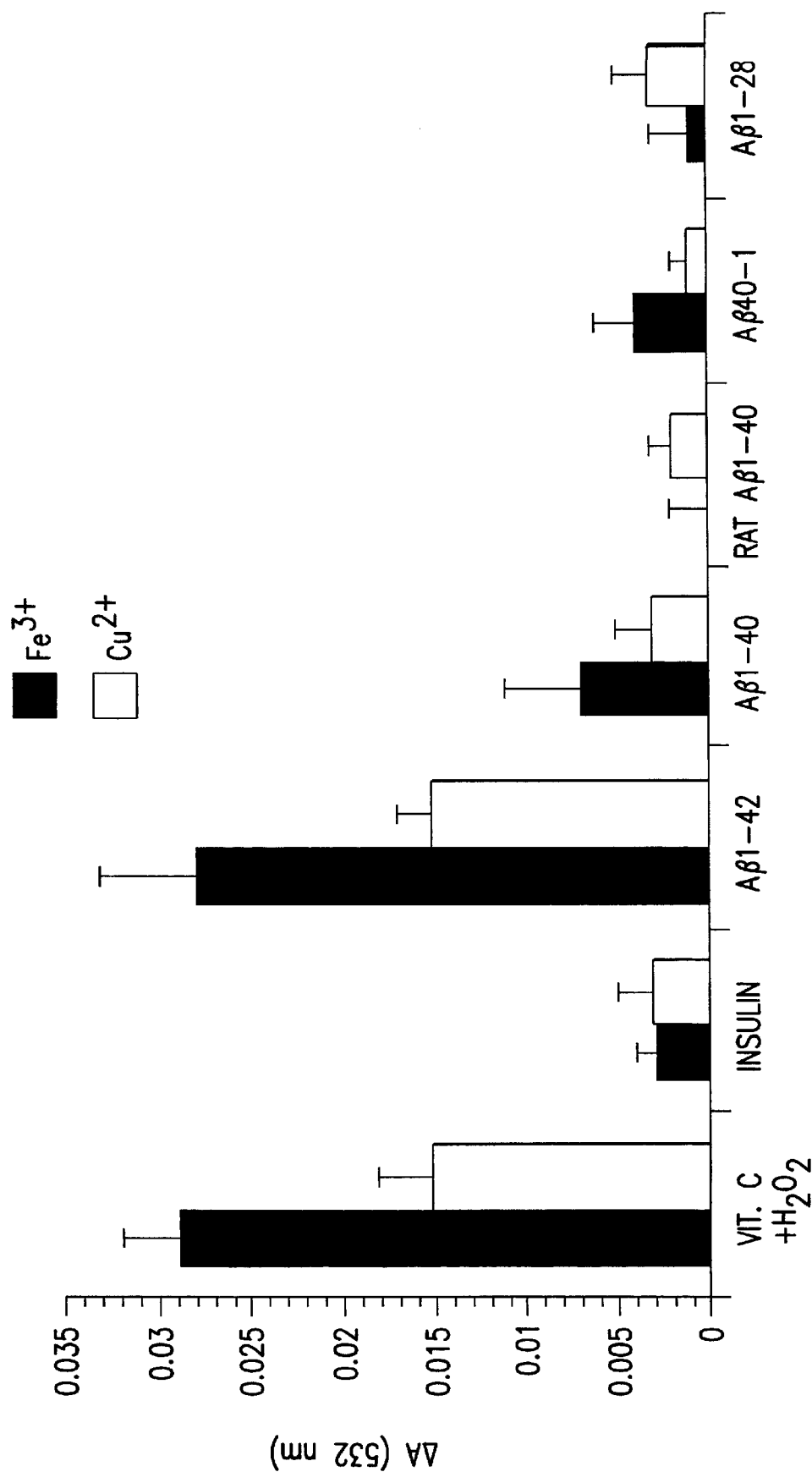
FIGS. 16A and 16B are graphical representations showing production of the hydroxyl radical (OH•) from the incubation of $A\beta$ in the presence of substoichiometric amounts of $Fe^{3+}$ or $Cu^{2+}$.

Having demonstrated that human $A\beta$ peptides simultaneously produce $H_2O_2$ and reduced metals, it was determined whether the hydroxyl radical was formed by the Fenton or Haber-Weiss reactions [Reactions (3) and (4)]. A modified TBARS assay was employed to detect OH• released from co-incubation mixtures of $A\beta$ peptides and 1 $\mu$M $Fe^{3+}$ or $Cu^{2+}$. As expected, $A\beta_{1-42}$ produced more OH• than $A\beta_{1-40}$, and rat $A\beta$ did not generate OH• (FIG. 16A). In contrast to the amount of $Fe^{2+}$ and $Cu^+$ produced (FIG. 13A), Aβ generated more OH• in the presence of $Fe^{3+}$ than in the presence of $Cu^{2+}$. This may be because $Fe^{2+}$ is more stable than $Cu^+$, which may be more rapidly oxidized by Reaction (1). Therefore, the $Fe^{2+}$ generated by Aβ may have a greater opportunity than the $Cu^+$ generated to react with $H_2O_2$. It is also possible that the contribution of the Haber-Weiss reaction to the production of OH• [Reaction (5)] is greater in the presence of $Fe^{3+}$ than in the presence of $Cu^{2+}$.

Figure 16B:
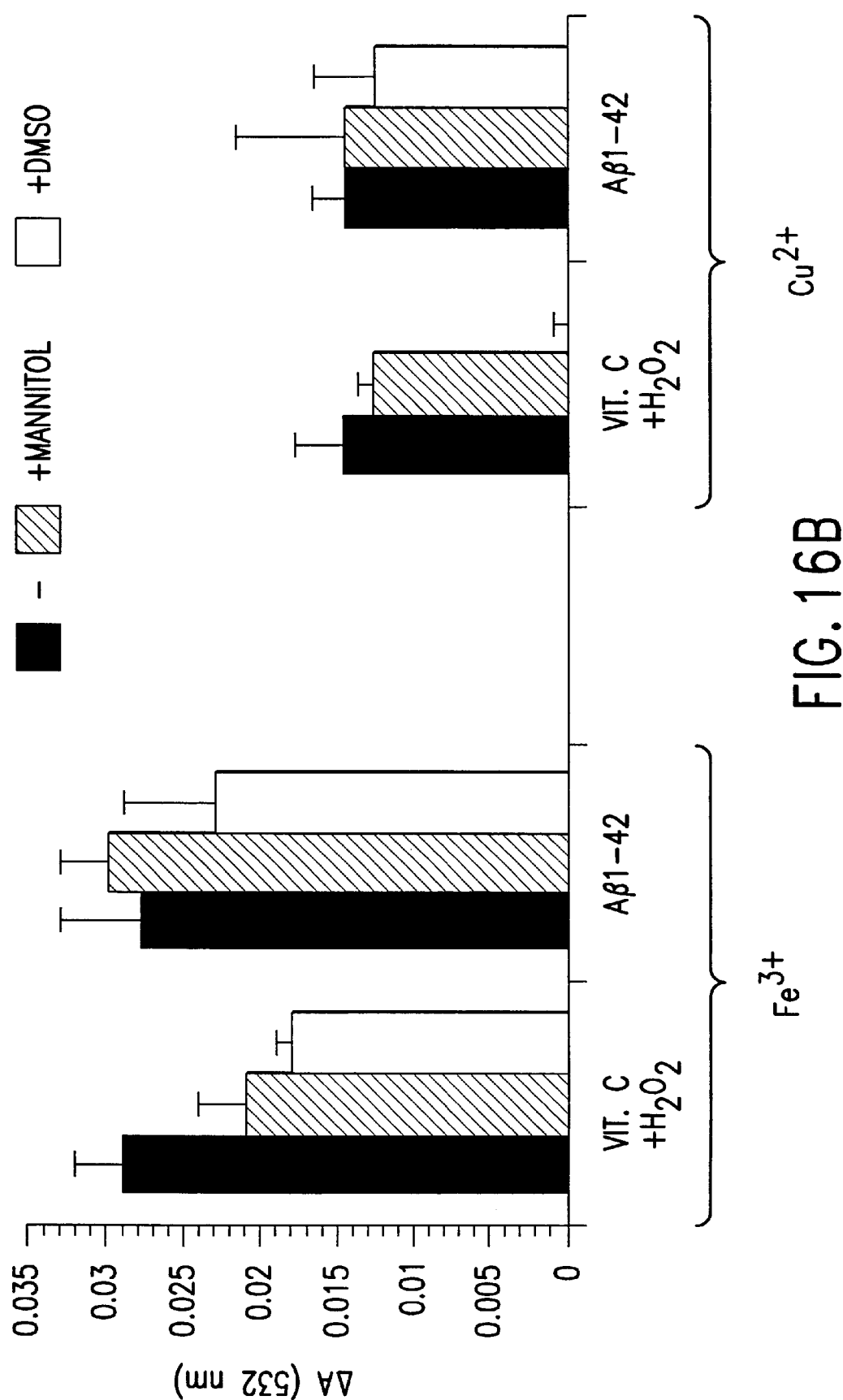

The effects of the OH• scavengers, dimethyl sulfoxide (DMSO) and mannitol, upon $Aβ_{1-42}$-mediated OH• generation were studied. Whereas these agents suppressed the generation of OH• by Vitamin C in the presence of $Fe^{3+}$, and DMSO suppressed the generation of OH• by Vitamin C in the presence of $Cu^{2+}$, neither were able to quench the generation of OH• by $Aβ_{1-42}$, whether in the presence of $Fe^{3+}$ or $Cu^{2+}$ (FIG. 16B). This suggests that these scavengers cannot encounter the OH• generated by Aβ before the TBARS reagent does.

e) Similarity Between Bleomycin-Fe and Aβ-Fe/Cu Complexes

The present Examples provide evidence for a model by which Fe/Cu and $O_2$ are mediators and substrates for the production of OH• by Aβ (FIGS. 16A and 16B) in a manner that depends upon the presence and length of the peptide's carboxyl terminus. The brain neocortex is an environment that is rich in both $O_2$ and Fe/Cu, which may explain why this organ is predisposed to Aβ-mediated neurotoxicity, if this mechanism is confirmed in vivo. The transport of Fe, Cu and Zn in the brain is largely energy-dependent. For example, the copper-transporting gene for Wilson's disease is an ATPase (Tanzi, R. E. et al., *Nature Genetics* 5:344 (1993)), and the re-uptake of zinc following neurotransmission is highly energy-dependent (Assaf, S. Y. & S. H. Chung, *Nature*, 308:734–736 (1984); Howell et al., *Nature*, 308:736–738 (1984)).

There is increasing evidence for lesions of brain energy metabolism in aging and AD (Parker et al., *Neurology*, 40:1302–1303 (1990); (Mecocci et al., *Ann. Neurol.* 34:609–616 (1993); Beal, M. F. *Neurobiol.* Aging 15 (Suppi 2):S171–S174(1994)). Therefore, damage to energy-dependent brain metal homeostasis may be an upstream lesion for the genesis of Aβ deposition in AD. Most brain biometals are bound to proteins or other ligands, however, according to our findings, only Aβ small fraction of the available metals needs to be derailed to the Aβ-containing compartment to precipitate the peptide and to activate its ROS-generating activities. The generation of ROS described herein depends upon the sub-stoichiometric amounts of $Fe^{3+}/Cu^{2+}$ (1:10, metal:Aβ), and it was estimated that 1% of the zinc that is released during neurotransmission would be sufficient to precipitate soluble Aβ in the synaptic vicinity (Huang, X. et al., *J. Biol. Chem.* 272:26464–26470 (1997)).

A polypeptide which generates both substrates of the Fenton reaction in sufficient quantities to form significant amounts of the OH• radical is unusual. Therefore, Aβ collections in the AD-affected brain are likely to be a major source of the oxidation stress seen in the effected tissue. One recent report describes that Aβ is released by the treatment of the mammalian lens in culture with $H_2O_2$ (Frederikse, P. H., et al., *J. Biol. Chem.* 271:10169 (1996)). If a similar response mechanism to $H_2O_2$ stress exists in neocortex, then the increasing $H_2O_2$ concentration generated by the accumulating Aβ mass in the AD-affected brain may induce the production of even more Aβ leading to a vicious cycle of Aβ accumulation and ROS stress.

The simultaneous production of Fenton substrates by Aβ is a chemical property that is brought into therapeutic application in the oxidation mechanism of the bleomycin-iron complex. Bleomycin is a glycopeptide antibiotic produced by *Streptomyces verticillus* and is a potent antitumor agent. It acts by complexing $Fe^{3+}$ and then binding to tumor nuclear DNA which is degraded in situ by the generation of OH• (Sugiura, Y., et al., *Biochem. Biophys. Res. Commun.* 105:1511(1997)). Similar to Aβ-$Fe^{3+}/Cu^{2+}$ complexes, incubation of bleomycin in aqueous solution also engenders the production of $O_2^-$, $H_2O_2$ and OH• in an $Fe^{3+}$-dependent manner. DFO could not inhibit $H_2O_2$ production from the Aβ-$Fe^{3+}/Cu^{2+}$ complex, and similarly, DFO does not inhibit the OH•-mediated DNA damage caused by the bleomycin-$Fe^{3+}$ complex. Also, low-molecular-mass OH• scavengers mannitol and DMSO were unable to inhibit the generation of OH• by Aβ-$Fe^{3+}/Cu^{2+}$, and are similarly unable to inhibit OH• production from bleomycin-$Fe^{3+}$.

It is proposed herein that inhibition of Aβ-mediated OH• provides means of treatment, e.g. therapy, by compounds that are Fe or Cu chelators. The clinical administration of DFO was reported as being effective in preventing the progression of AD (Crapper-McLachlan, D. R. et al., *Lancet* 337:1304 (1991)); however, since DFO chelates $Zn^{2+}$ as well as $Fe^{3+}$ and Al(III), the effect, if verifiable, may not have been due to the abolition of the redox activity of Aβ, but may have been due to the disaggregation of $Zn^{2+}$-mediated Aβ deposits (Cherny, R. A. et al., *Soc. Neurosci. Absir.* 23:(abstract)(1997)) which may have reduced cortical Aβ burden and, consequently, oxidation stress.

f) Oxidative Stress and Alzheimer's Disease Pathology

Autopsy tissue from AD subjects has been reported to exhibit higher basal TBARS formation than control material (Subbarao, K. V. et al., *J. Neurochem.* 55:342 (1990); Balazs, L. and M. Leon, *Neurochem. Res.* 19:1131 (1994); Lovell et al., *Neurology* 45:1594 (1995)). These observations could be explained, on the basis of the present findings, as being due to the reactivity of the Aβ content within the tissue. $Aβ_{1-40}$ recently has been shown to generate TBARS in a dose-dependent manner when incubated in cell culture, however TBARS reactivity was reduced by pre-treating the cells with trypsin which also abolished the binding of the peptide to the RAGE receptor (Yan et al., *Nature* 382:685 (1996)). One possibility for this result is that the RAGE receptor tethers an Aβ microaggregate sufficiently close to the cell to permit increased penetration of the cell by $H_2O_2$ which may then combine with reduced metals within the cell to generate the Fenton reaction. Alternatively, Aβ may generate the Fenton chemistry at the RAGE receptor. The resulting attack of the cell surface by the highly reactive OH• radical, which reacts within nanometers of its generation, may have been the source of the positive TBARS assay.

APP also reduces $Cu^{2+}$, but not $Fe^{3+}$, at a site in its amino terminus (Multhaup, G., et al., *Science* 271:1406–1409 (1996)), adjacent to a functional and specific $Zn^{2+}$-binding site that modulates heparin binding and protease inhibition (Bush et al., 1993; Van Nostrand, 1995). Therefore, the amino terminus of APP reiterates an association with transition metal ions that is found in the Aβ domain. This intriguing theme of tandem Cu/Zn interaction and associated redox activity found in two soluble fragments of the parent protein may indicate that the function and metabolism of APP could be related to biometal homeostasis and associated redox environments.

The present findings indicate that the manipulation of the brain biometal environment with specific agents acting directly (e.g. chelators and antioxidants) or indirectly (e.g. by improving cerebral energy metabolism) holds promise as a means for therapeutic intervention in the prevention and treatment of Alzheimer's disease.

Example 4

Resolubilization of Aβ

Considerable evidence now indicates that the accumulation of Aβ in the brain cortex is very closely related to the cause of Alzheimer's disease. Aβ is a normal component of biological fluids whose function is unknown. Aβ accumulates in a number of morphologies varying from highly insoluble amyloid to deposits that can be extracted from post-mortem tissue in aqueous buffer. The factors behind the accumulation are unknown, but the inventors have systematically appraised the solubility of synthetic Aβ peptide in order to get some clues as to what kind of pathological environment could induce the peptide to precipitate.

It was found that Aβ has three principal vulnerabilities—zinc, copper and low pH. The precipitation of Aβ by copper is dramatically exaggerated under mildly acidic conditions (e.g., pH 6.9), suggesting that the cerebral lactic acidosis that complicates Alzheimer's disease could contribute to the precipitation of Aβ were this event to be mediated by copper. A consideration of the involvement of zinc and copper in plaque pathology is contemplatable since the regulation of these metals in the brain has been shown to be abnormal in AD.

Recently direct evidence has been obtained indicating that these metals are integral components of the Aβ deposits in the brain in AD. It was found that zinc- and copper-specific chelators (including clioquinol) dramatically redissolve a significant proportion (up to 70%) of Aβ extracted from post-mortem AD affected brain tissue, compared to the amount extracted from the tissue by buffer in the absence of chelators.

These data support a strategy of redissolving Aβ deposits in vivo by chelation. Therefore, clioquinol is an excellent candidate for further development since it chelates both copper and zinc, and since it is hydrophobic, is enriched in the brain. Interestingly, a reported success in attempting to slow down the progression of Alzheimer's disease used a chelation strategy with desferrioxamine. The authors (Crapper-McLachlan, D. R., et al., 337:1304 (1991), thought that they were chelating aluminum, but desferrioxamine is also a chelator of copper and zinc. Treatment with desferrioxamine is impractical because the therapy requires twice daily deep intramuscular injections which are very painful, and also causes side effects such as anaemia due to iron chelation.

Resolubilization of Metal-induced Aβ Aggregates by Chelators

Figure 17:
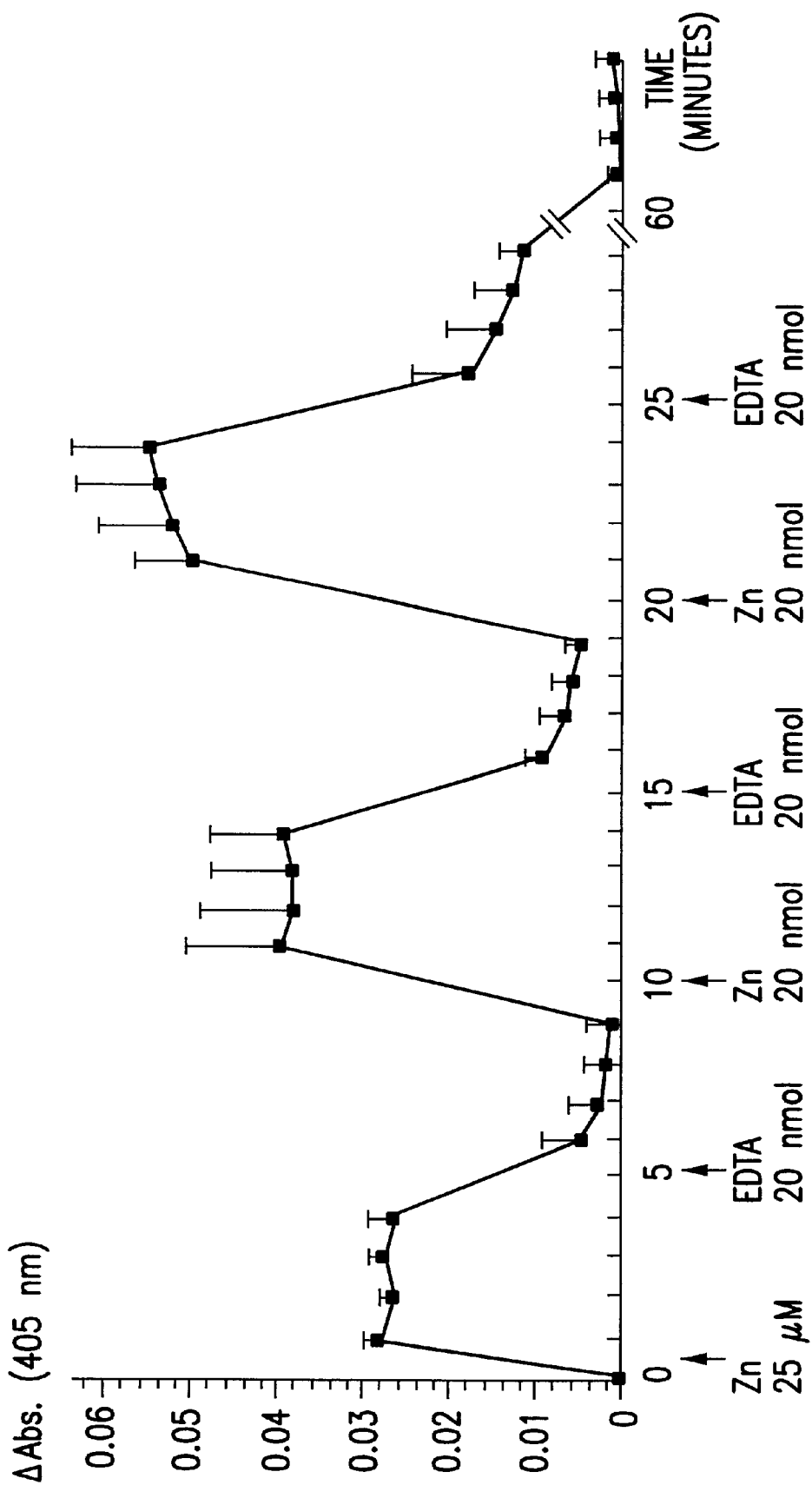
FIG. 17 shows the reversibility of zinc-induced $A\beta_{1-40}$ aggregation with EDTA. Aggregation induced by pH 5.5 was not reversible in the same manner.
Figure 18:
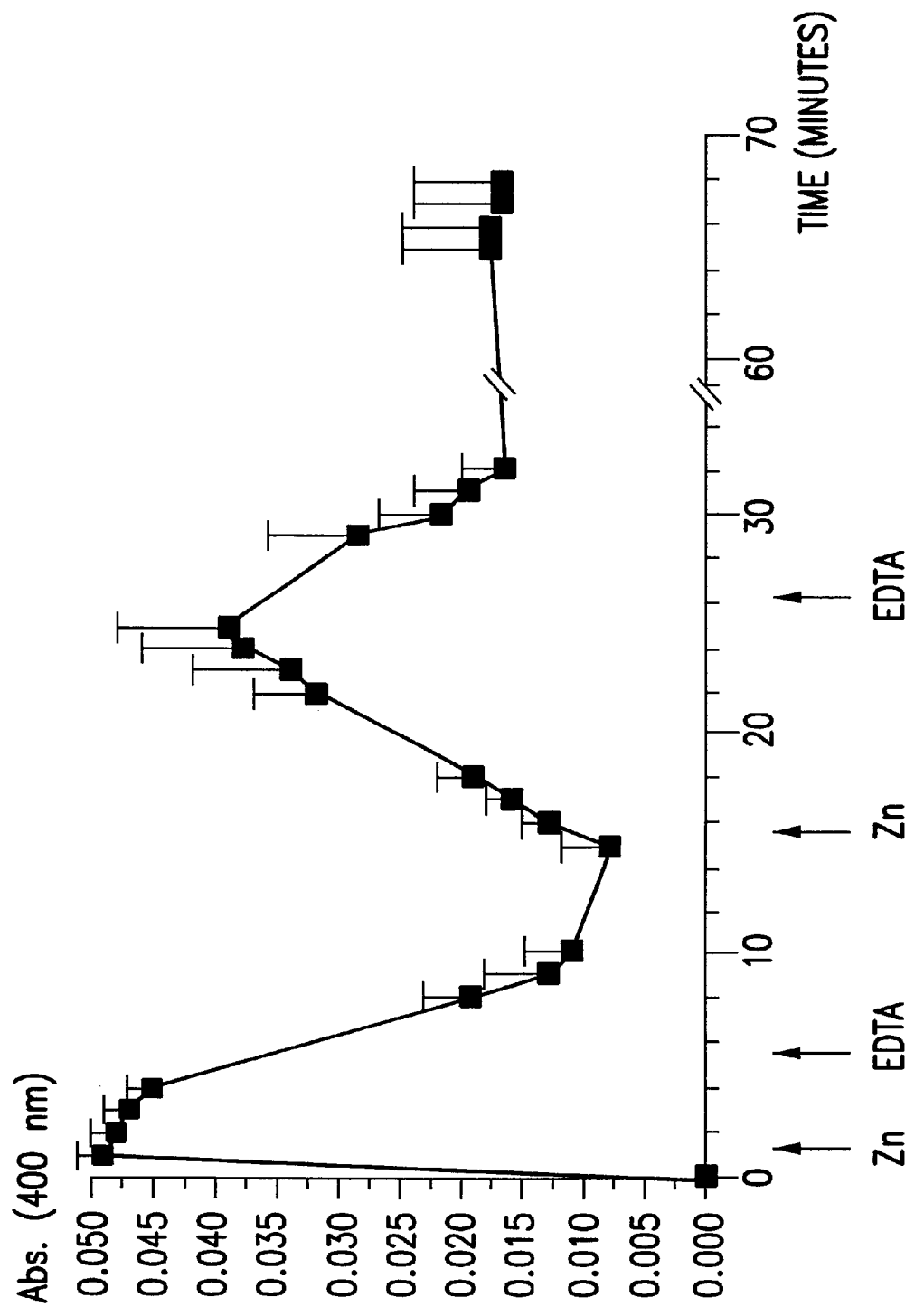
FIG. 18 shows the reversibility of zinc-induced aggregation of $A\beta_{1-40}$ mixed with 5% $A\beta_{1-42}$.

Aβ (10 ng/well in TBS) aggregation was induced by addition of $ZnCl_2$ (25 μM), $CuCl_2$ (5 μM) or acidic conditions (pH 5.5). Aggregates were transferred to a 0.2 μ nylon membrane by filtration. The aggregates were then washed (200 μl/well) with TBS alone, TBS containing 2 μM EDTA, or TBS containing 2 μM clioquinol. The membrane was fixed, probed with the anti-Aβ monoclonal antibody 6E10, and developed for exposure to F,CL-film. FIG. 17 shows relative signal strength as determined by transmittance analysis of the ECL-film, calibrated against known amounts of the peptide. Values are expressed as a percentage of Aβ signal after washing with TBS alone.

Both EDTA and clioquinol treatments were more effective than TBS alone at resolubilizing the retained (aggregated) Aβ when the peptide was precipitated by Zn or Cu (see FIG. 17). When Aβ was precipitated by pH 5.5 however, it was not resolubilized more readily by either chelator compared to TBS washing alone. The pH 5.5 precipitate contains a much greater proportion of beta-sheet amyloid than the Aβ precipitates formed by Zn or Cu.

Example 5

Aβ Extraction from Human Brain Post-Mortem Samples

The inventors have recently characterized zinc-mediated Aβ deposits in human brain (Cherny, R. A., et al., *Soc. Neurosci Abstr.* 23:(Abstract) (1997)). It was recently reported that there is a population of water-extractable Aβ deposit in the AD-affected brain (Kuo, Y-M., et al., *J. Biol. Chem.* 271:4077–81 (1996)). The inventors hypothesized that homogenization of brain tissue in water may dilute the metal content in the tissue, so lowering the putative zinc concentration in Aβ collections, and liberating soluble Aβ subunits by freeing Aβ complexed with zinc [$Zn^{2+}$].

To test this hypothesis, the brain tissue preparation protocol of Kuo and colleagues was replicated, but phosphate-buffered saline pH 7.4 (PBS) was substituted as the extraction buffer, achieving similar results. Highly sensitive and specific anti-Aβ monoclonal antibodies (Ida, N., et al., *J. Biol. Chem.*, 271:22908 (1996)) were used to assay Aβ extraction by western blot. Next, the extraction of the same material was repeated with PBS in the presence of chelators of varying specificities (Table 1), and it was determined that the presence of a chelator increased the amount of Aβ in the soluble extract several-fold (FIGS. 19A–19C, 20A and 20B, 25A; Table 2).

The amount of Aβ detected in the pellet fraction of each sample is correspondingly lower, indicating that the effect of the chelator is upon the disassembly of the Aβ aggregate, and not by inhibition of an Aβ-cleaving metalloprotease (such as insulin degrading enzyme cleavage of Aβ reported recently by Dennis Selkoe at the 27th Annual Meeting for the Society for Neuroscience, New Orleans). The extraction of sedimentable Aβ into the soluble phase correlated only with the extraction of zinc from the pellet, and not with any other metal assayed (Table 3). Examination of the total amount of protein released by the treatments revealed that chelation was not merely liberating more proteins in a non-specific manner.

TABLE 1

Dissociation Constants for Metal Ions of Various Chelators Used to Extract Human Brain Aβ.

| CHELATOR | Ca | Cu | Mg | Fe | Zn | Al | Co |
|---|---|---|---|---|---|---|---|
| EGTA | 10.9 | 17.6 | 5.3 | 11.8 | 12.6 | 13.9 | 12.4 |
| BDTA | 10.7 | 18.8 | 8.9 | 14.3 | 16.5 | 16.5 | 16.5 |
| Penicillamine | 0 | 18.2 | 0 | 0 | 10.2 | 0 | 0 |
| TPEN | 3.0 | 20.2 | 0 | 14.4 | 15.4 | 0 | 0 |
| Bathophenanthroline | 0 | 8.8 | 0 | 5.6 | 6.9 | 0 | 0 |
| Bathocuproine (BC) | 0 | 19.1 ($Cu^+$) | 0 | 0 | 4.1 | 0 | 4.2 |

LogK is illustrated for the chelators, where K=[ML]/[M][L]. Different chelators have greatly differing affinities for metal ions, as shown. TPEN is relatively specific for Zn and Cu, and has no affinity for Ca and Mg (which are far more abundant metal ions in tissues). Bathocuproine (BC) has high affinity for zinc and for cuprous ions. Whereas all the chelators examined have a significant affinity for zinc, EGTA and EDTA have significant affinities for Ca and Mg.

The ability of chelators to extract Aβ from post-mortem brain tissue was studied in over 40 cases (25 AD, 15 age-matched and young adult controls all confirmed by histopathology). While there is a lot of variation between samples as to what is the best concentration of given chelator for the optimum extraction of Aβ, there are no cases where a chelator does not, at some concentration, extract far more Aβ than PBS alone.

Figure 19A:
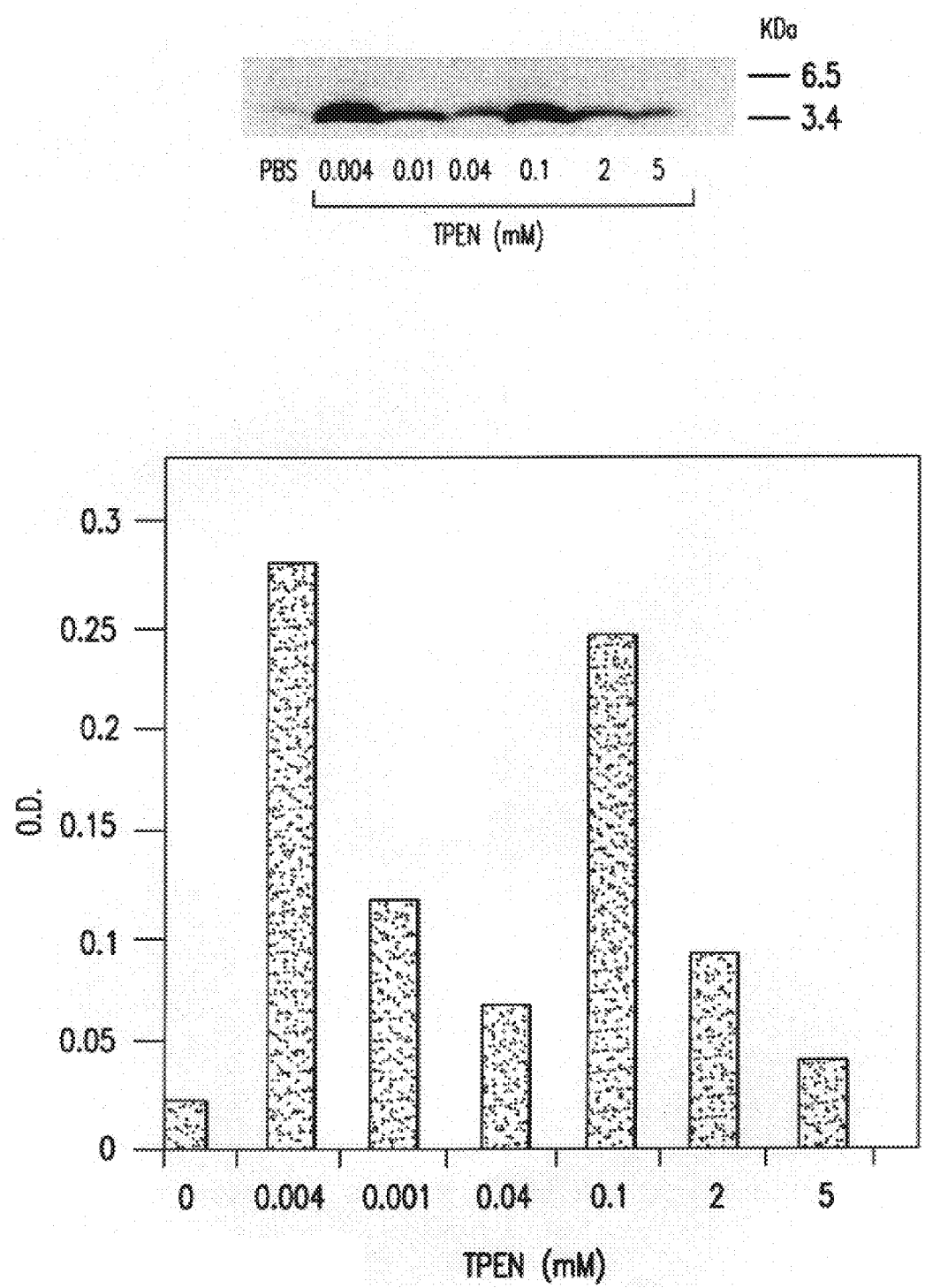
FIGS. 19A–19C show dilution curves for TPEN, EGTA, and bathocuproine, respectively, used in extracting a representative AD brain sample.
Figure 19B:
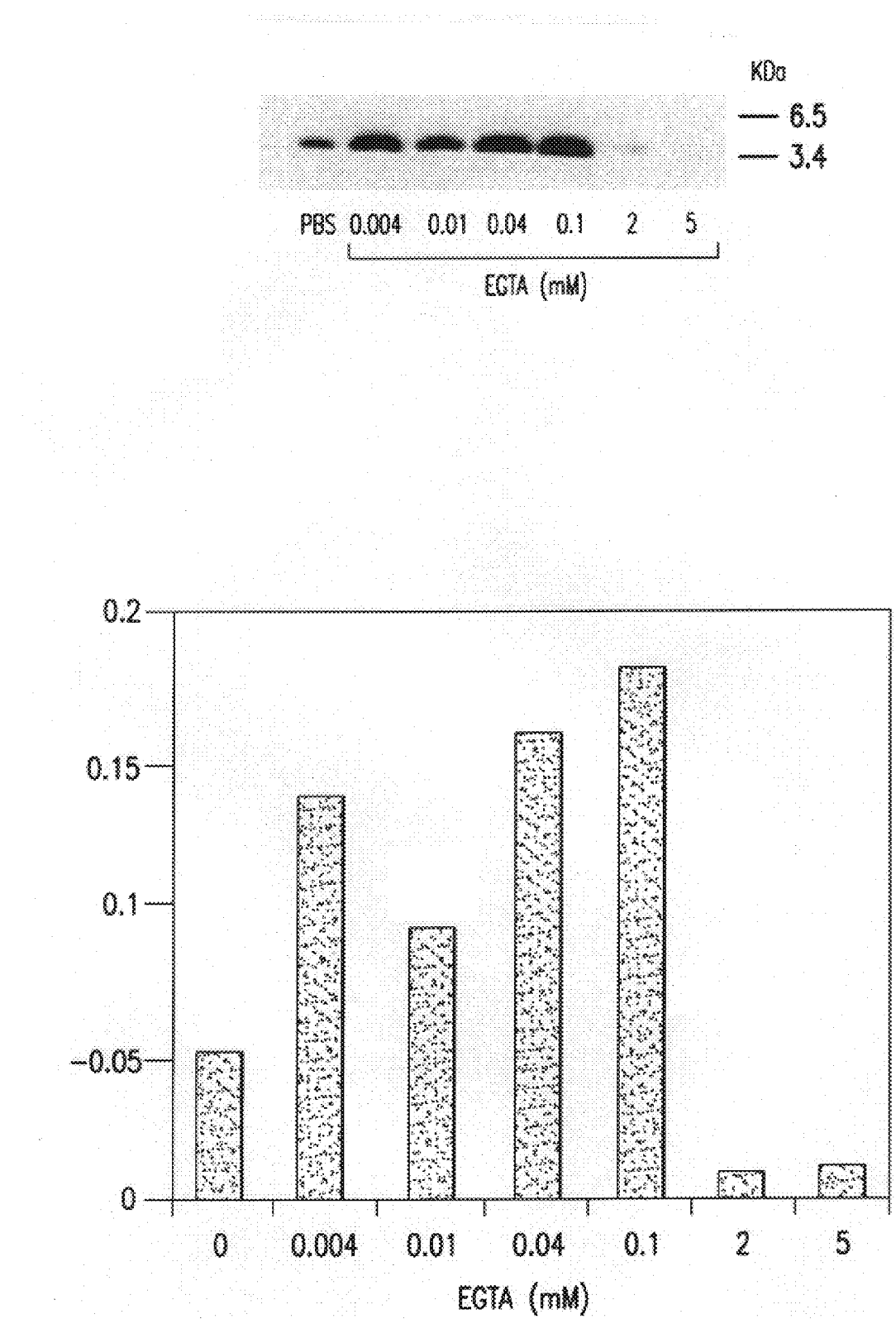
Figure 19C:
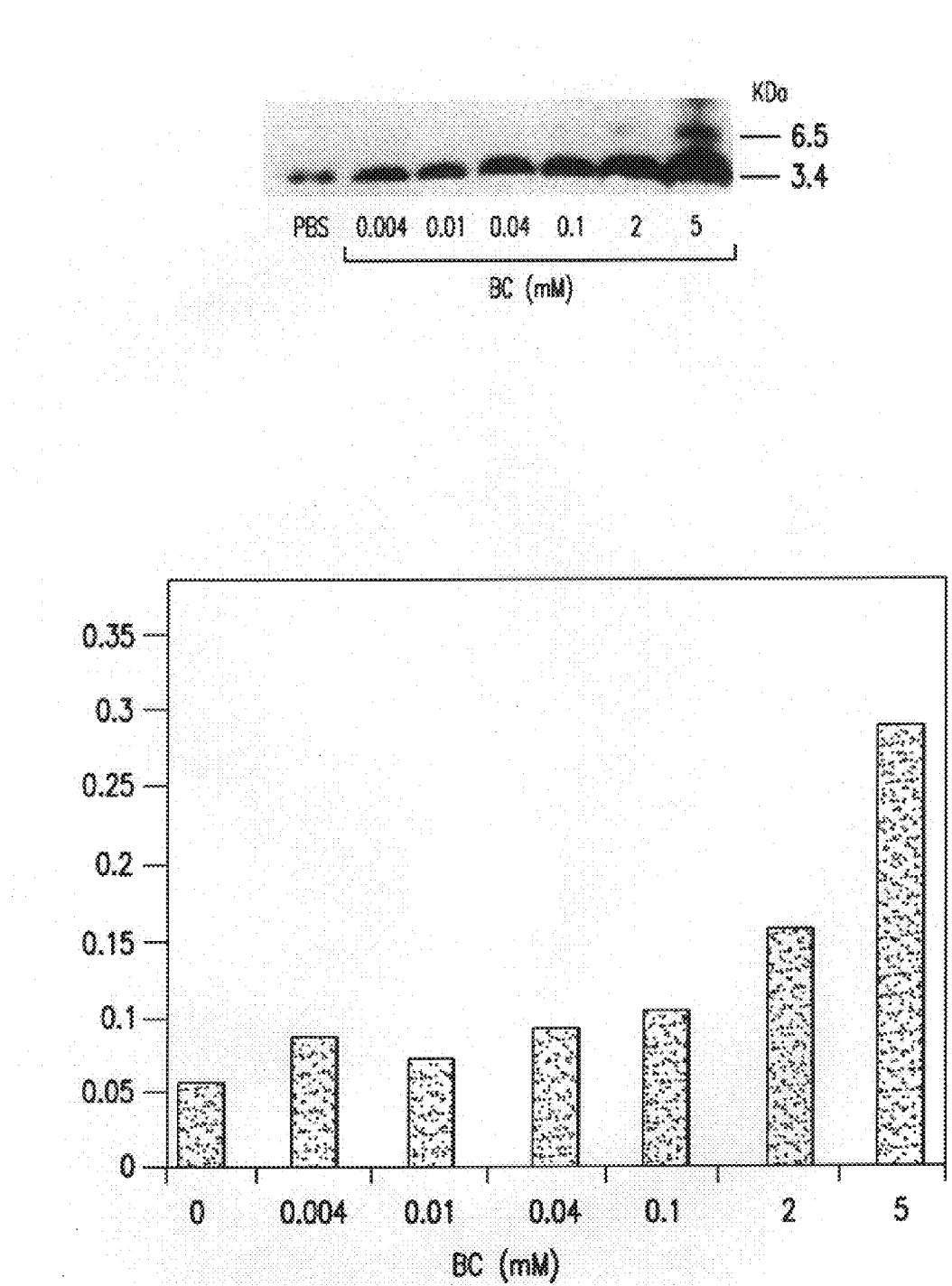

FIG. 19 shows that metal chelators promote the solubilization of Aβ from human brain sample homogenates. Representative curves for three chelators (TPEN, EGTA, Bathocuproine) used in extracting the same representative AD brain sample are shown. 0.5 g of prefrontal cortex was dissected and homogenized in PBS±chelator as indicated. The homogenate was then centrifuged (100,000 g) and the supernatant removed, and a sample taken for western blot assay using anti-Aβ specific antibodies after Tricine PAGE. Densitometry was performed against synthetic peptide standards. The blots shown here represent typical results. Similar results were achieved whether or not protease inhibitors were included in the PBS (extraction was at 4° C.). Furthermore, similar results were achieved when the brain sample was homogenized in PBS and then pelleted before treated with PBS±chelator. There is also a complex relationship between the dose of the chelator and the resultant resolubilization of Aβ (FIGS. 19A–C). For the same given sample, neither TPEN nor EGTA could increase the extraction of Aβ in a does-dependent manner. Rather, although concentrations of chelators could be very effective in the low micromolar range (e.g., TPEN 4 μM, FIG. 19A), higher concentrations induced a paradoxical loss of recovery. This kind of response was found in every case examined. The extraction of Aβ is abolished by adding exogenous zinc, but is enhanced by adding magnesium. Preliminary in vitro data indicate that whereas Mg has no effect on the precipitation of Aβ, its presence enhances the peptide's resolubilization following zinc-induced precipitation. Therefore, the "polyphasic" profile of chelator extraction of Aβ, with higher concentrations of TPEN and EGTA inducing a loss of recovery, may be explained by the chelation of Mg that is only expected to occur after the chelation of zinc when the relative abundance of Mg in the sample, and the relative dissociation constants of TPEN and EGTA are considered.

In contrast, bathocuproine (BC) exhibits a clear dose-dependent increase in Aβ extraction from human brain, probably due to its relatively high specificity for zinc, although an interaction with trace amounts of $Cu^+$ or other metals not yet assayed, cannot be excluded.

Western blot analysis of extracts using $A\beta_{1-42}$-specific monoclonals revealed the presence of abundant $A\beta_{1-42}$ species. It was observed that ≈20% of AD cases exhibit clear SDS-resistant Aβ dimers in the soluble extract after treatment with chelators. These dimers are reminiscent of the neurotoxic $A\beta_{1-42}$ dimers that were extracted by Roher and colleagues from AD-affected brain (Roher, A. E., et al., *Journal of Biological Chemistry* 271:20631–20635 (1996)). An estimation of the proportion of total precipitated Aβ in the sample was achieved by extracting the homogenate pellet following centrifugation, into formic acid, and then performing a western blot on the extract following neutralization. The proportion of pelletable Aβ that is released by chelation treatment varies considerably from case to case, from as little as 30% to as much as 80%. In the absence of a chelator, no more than ≈10% of the total pelletable Aβ is extracted by PBS alone.

One preliminary emerging trend is that samples with a greater proportion of diffuse or vascular Aβ deposit are more likely to have their pelletable Aβ resolubilized by chelation treatment. Also, extraction of the tissue homogenate overnight with agitation greatly increases the amount of Aβ extracted in the presence of chelators (compared to PBS alone), when compared to briefer periods of extraction indicating that the disassembly of Aβ deposits by chelation treatment is a time-dependent reaction and is unlikely to be due to inhibition of a protease. A study of brain cortical tissue from one amyloid-bearing APP transgenic mouse indicates that, like human brain, homogenization in the presence of a chelator enhances the extraction of pelletable Aβ.

Effects of various chelators on the extraction of Aβ into the supernatant as a percentage change from control extractions is summarized below in Table 2.

TABLE 2

Effects of Various Chelators Upon Extraction of Aβ.
Effect of Chelators (% change from control)

| | TPEN | | EGTA | | BATHOCUP | |
|---|---|---|---|---|---|---|
| | 0.1 mM | 2.0 mM | 0.1 mM | 2.0 mM | 0.1 mM | 2.0 mM |
| Mean(n = 6) | 182 | 241 | 207 | 46 | 301 | 400 |
| +/−SD | 79 | 81 | 115 | 48 | 190 | 181 |

Densitometry of Aβ western blots (FIGS. 19A–19C) was performed for a series of 6 AD brain samples homogenized in the presence of chelators as indicated. The mean (±SD) increases in signal, above the signal generated by PBS extraction alone, are indicated in Table 2. A significantly increased amount of chelator-induced Aβ resolubilization was achieved by a 16 hour extraction with agitation in subsequent studies.

Table 3 shows a comparison between pellets of post-centrifugation homogenates in the presence and absence of a chelator (TPEN).

TABLE 3

Residual Metals in Pellets of Post-Centrifugation Homogenatesin the Presence and Absence of Chelator.

| METAL | Zn | Cu | Fe | Ca | Mg | Al |
|---|---|---|---|---|---|---|
| PBS alone mg/kg (SD) | 50.7 (12.0) | 11.9 (3.5) | 227 (69) | 202 (69) | 197 (94) | 44 (111) |
| +TPEN mg/kg (SD) | 33.2* (9.8) | 9.8 (3.1) | 239 (76) | (210) (89) | 230 (94) | 65 (108) |

Frontal cortex from AD (n=6) and healthy controls (n=4) was homogenized in the presence and absence of PBS±TPEN (0.1 mM). After ultracentrifugation of the homogenate, the pellets were extracted into concentrated HCl and measured for metal content by ion coupled plasma - atomic emission spectroscopy (ICP-AES).

Figure 20A:
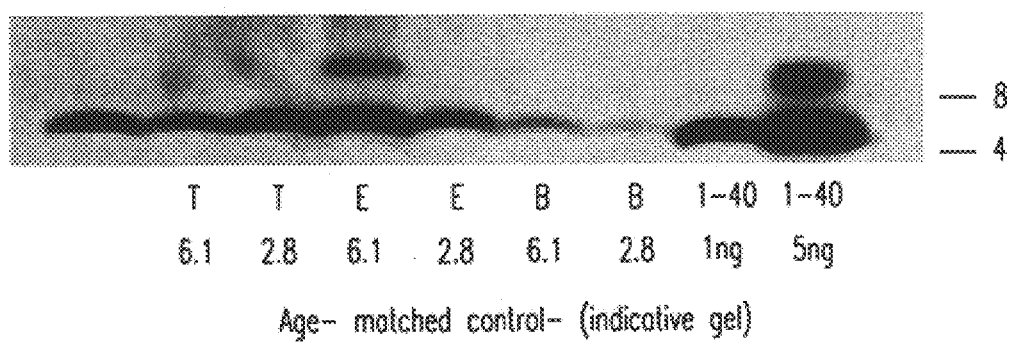
FIGS. 20A and 20B—FIG. 20A shows a western blot of chelation response in a typical AD brain.
Figure 20B:
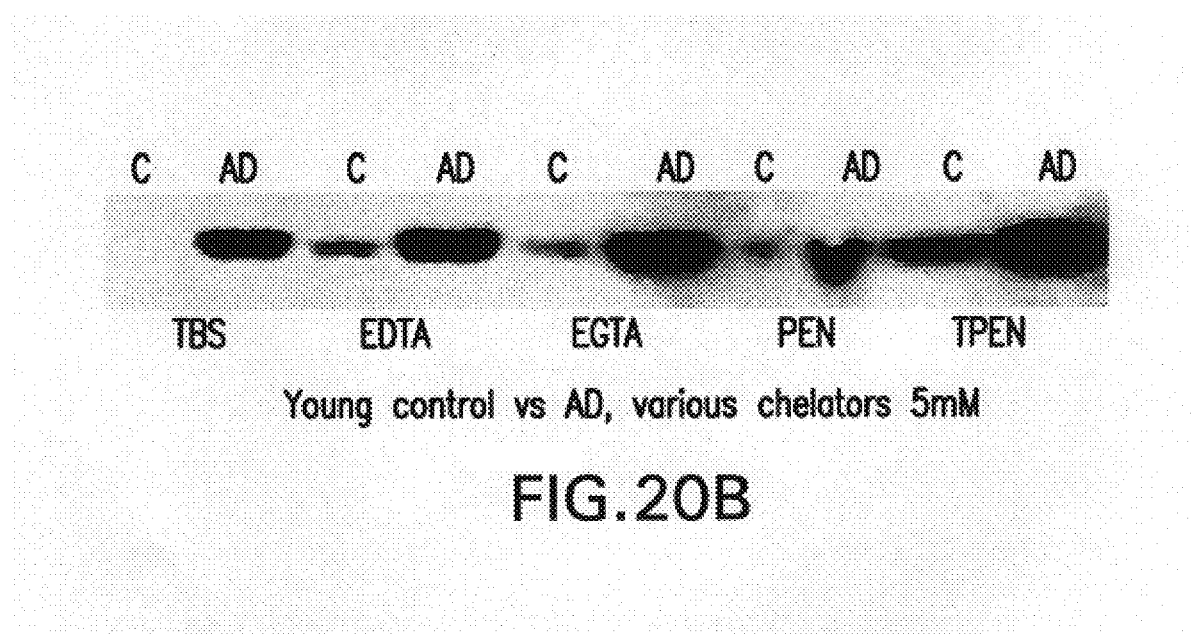

Using the same technique, zinc-mediated assembly of Aβ in normal brains was shown. FIGS. 20A and 20B show sedimentable Aβ deposits in healthy brain tissue. The effects of chelators in enhancing Aβ extraction from brain homogenates is also observed in normal tissue. FIG. 20A illustrates a western blot with anti-Aβ antibody of material extracted from a 27-year-old individual with no history of neurological disorder. T=TPEN, E=EGTA, B=bathocuproine. Bathocuproine is much less effective in extracting Aβ from control tissue than from AD tissue. These data are typical of 15 cases.

As expected, far less total Aβ is present in normal brain samples compared to AD brain samples, although the content of Aβ increases with age. It is possible that these findings in young adult brains represent the zinc-mediated initiation of amyloid formation in deposits that, in youth, are too diffuse to be detected by immunohistochemistry.

Figure 21:
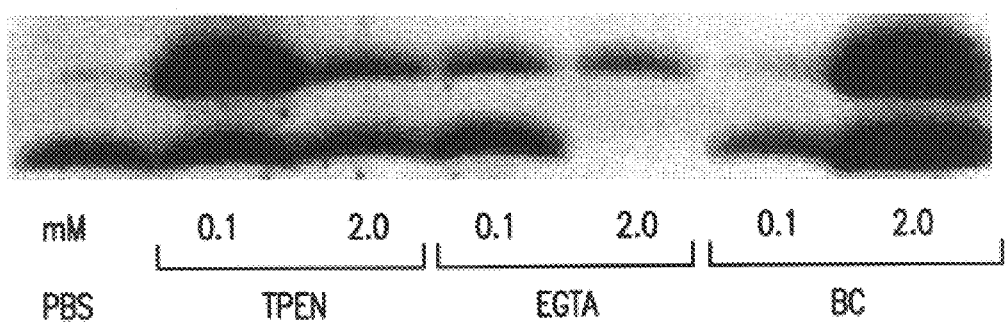
FIG. 21 shows an indicative blot from AD brain extract. The blot shows that chelation treatment results in disproportionate solubilization of $A\beta$ dimers, while PBS alone does not.

Roher and others have suggested that dimers of Aβ are the toxic component of amyloid. As shown in FIG. 21, dimers appear in response to chelation in disproportion to the monomeric signal (treatment with PBS alone does not generate soluble dimers). This suggests that Aβ deposits are being dismantled by the chelators into SDS-resistant dimeric structural units.

Figure 22:
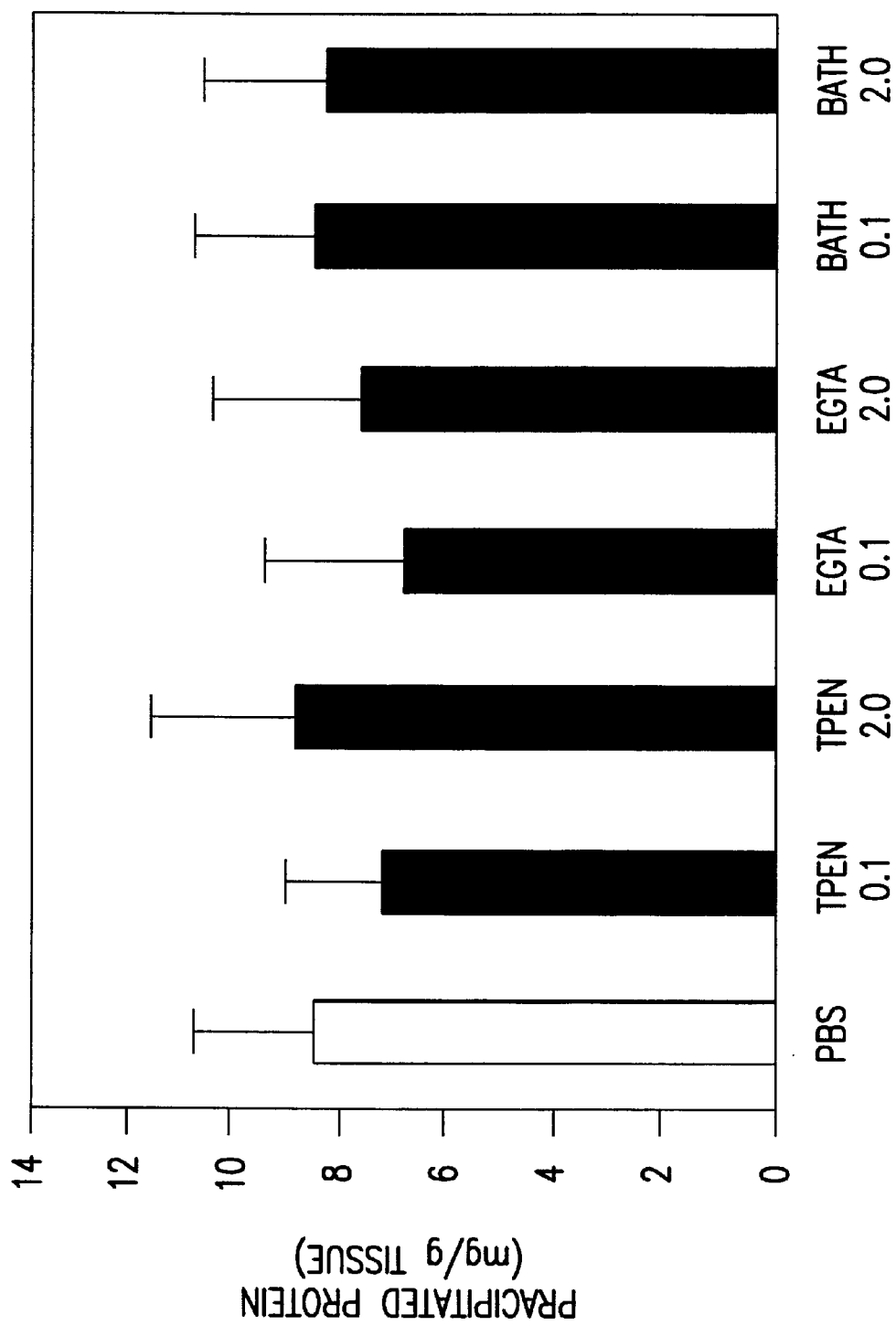
FIG. 22 shows that recovery of total soluble protein is not affected by the presence of chelators in the homogenization step.

FIG. 22 shows that the recovery of total soluble protein is not affected by the presence of chelators in the homogenization step. The proportionality of extracted subfractions, calculated based on total protein as determined by formic acid extraction, should not be prone to artifact based on chelator-specific affects.

Example 6

Resolubilization of Aβ by Clioquinol

In one previous attempt to use metal chelation as a therapeutic for AD, Crapper-McLachlan and colleagues (Crapper-McLachlan, D. R., et al., 337:1304 (1991)) administered intramuscular desferrioxamine (DFO) daily to a small cohort of AD patients, and reported that their treatment attenuated the progression of the disease. Replication of this study has not been attempted.

The inventors attributed the beneficial effect to the removal of aluminum; however, they have conceded in presentations at meetings (e.g. International Conference on Alzheimer's Disease, 1992, Padua) that postmortem metal analysis on brain tissue from subjects in the study indicated that although aluminum levels were lower than placebo controls, zinc and iron levels were also lower in the brains of subjects treated with DFO. This is because, like all chelators, DFO has only a relative specificity for aluminum, but will also complex with zinc and iron. There appears to be no report on a histopathological analysis of post-mortem brain Aβ content in the subjects who took DFO compared to the controls.

The administration of DFO, a painful intramuscular injection, is fraught with complications including the non-specific problems of chelation therapies (e.g. anemia). Although the results of Crapper-McLachlan and colleagues remain contentious and have not yet been reproduced, the possibility that the beneficial effects they reported were due to the partial removal of zinc from brain Aβ collections cannot be excluded. DFO is a charged molecule that does not easily penetrate the blood-brain barrier, and, as such, is not an ideal candidate for the removal of zinc from Aβ deposits, especially as its affinity for zinc is relatively low. Therefore, a more suitable candidate compound to attempt a trial of Aβ Dissolution in APP Tgs was sought.

Clioquinol (iodochlorhydroxyquin, 5-chloro-7-iodo-8-hydroxyquinoline, MW 305.5) is a USP drug that chelates zinc [K(Zn)=12.5, K(Cu)=15.8, K(Ca)=8. 1, K(Mg)=8.6], is hydrophobic, has a low general toxicity profile, and crosses the blood brain barrier (Padmanabhan et al., 1989). It therefore possesses some of the ideal prototypic properties for a candidate agent that could solubilize zinc-assembled Aβ deposits in vivo. It has been used as an oral antiamebic antibiotic, and as a topical antibiotic.

It has been demonstrated that clioquinol is rapidly absorbed from the gut of rats and mice where blood levels reached ≈1–10 μM within one hour of ingestion (Kotaki et al., *J Pharmacobiodyn*, 6(11):881–887 (1983)). Since the drug is hydrophobic, it passes rapidly into the brain, and then is rapidly excreted, so that a bolus dose of clioquinol is almost completely removed from the brain within three hours. It appears to be safe in many mammalian species, including rat and mouse (Tateishi, J., et al., *Lancet*, 2(7786) :1096 (1972); Tateishi, J., et al., *Acta Neuropathol.*, (Berl), 24(4):304–320 (1973)), and is still used as a veterinary antibiotic (Entero Vioform).

Clioquinol was withdrawn from use as an oral antibiotic for humans in the early 1970's when its ingestion in Japan was linked to a mysterious condition called subacute myelo-optic neuritis (SMON), a condition that resembles subacute combined degeneration of the cord caused by vitamin B12 deficiency. The mechanism of SMON has never been elucidated, but in the 1970's a considerable literature developed exploring the pathophysiology of clioquinol ingestion (Tateishi, J., et al.,*Lancet*, 2(7786):1096 (1972); Tateishi, J., et al., *Acta Neuropathol.*, (Berl), 24(4):304–320 (1973)). Several reports have demonstrated that clioquinol complexes with zinc in the brain, especially in areas enriched in synaptic vesicular zinc such as the temporal lobe (Shiraki, H. *Handhook of Clinical Neurology*, Vol. 37 (1979)). Indeed, over ingestion of clioquinol has been reported to induce amnesia in humans (Shiraki, H. *Handbook of Clinical Neurology*, Vol. 37 (1979)).

Because of its relatively safe profile in mice, and because there is a large literature on its pharmacology in this animal, clioquinol was chosen for study as a means to specifically chelate zinc from Aβ deposits in vitro (induced aggregates and brain samples). It is possible that the low concentrations of clioquinol shown to be effective in resolubilizing Aβ in the present invention may avoid the adverse SMON effect noted above. Thus, given its other pharmacological properties, clioquinol may hold promise as a effective agent in the treatment of AD in humans.

Dissolving Clioquinol

In order to obtain a solution of clioquinol in PBS, the following protocol was followed: 5.3 grams of clioquinol was suspended with agitation in 200 milliliter of n-decane. The undissolved material was settled, air dried, and weighed, based on which it was determined that only 2 % of the clioquinol had dissolved in the n-decane. 100 milliliter of the supernatant (light yellow) was agitated in 100 milliliter of PBS, pH 7.4. Next, the phases were allowed to separate. The lower phase (PBS) was collected and filtered to remove the residue which had formed at the phase interface upon extraction with the organic solvent. The concentration of clioquinol in the PBS was determined to be 800 nanomolar. This number was arrived at based on two assumptions: (1) 2% of the clioquinol was dissolved in the n-decane; and (2) the partitioning coefficient is 1/1750 with PBS at 1:1 mixture of n-decane to clioquinol.

Resolubilization of In Vitro Metal-Induced Aβ Augregates

Figure 23:
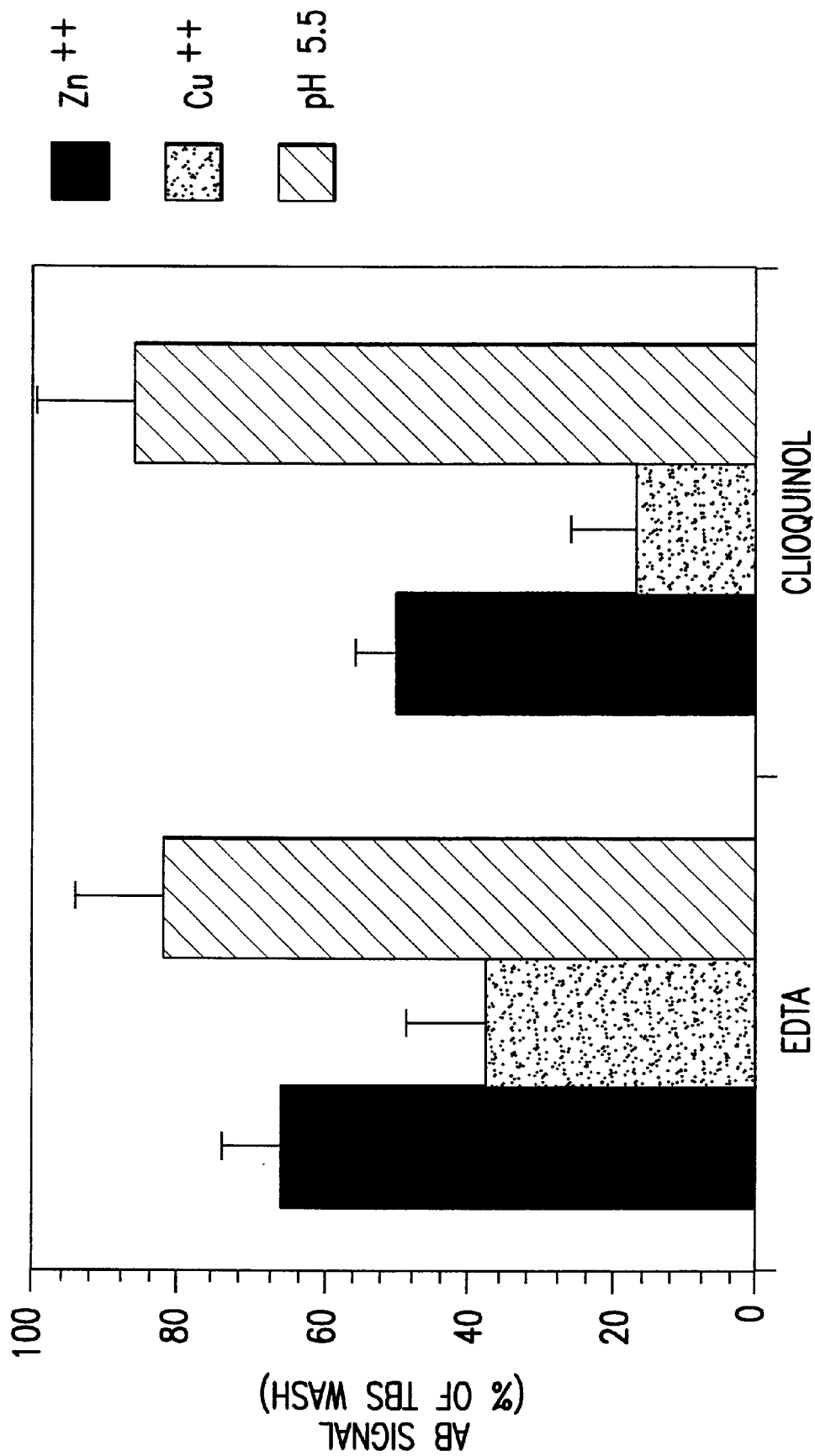
FIG. 23 is a graphical representation of resolubilization of Zn, Cu, or pH induced aggregates in vitro. Values arc expressed as a percentage of $A\beta$ signal after washing with TBS alone.

First, in order to appraise the efficacy of clioquinol in resolubilizing Aβ aggregates, its ability to resolubilize Aβ aggregates formed in vitro by the action of $Cu^{2+}$ or $Zn^{2+}$ upon $Aβ_{1-40}$ was examined FIG. 23 shows resolubilization of metal-induced Aβ aggregate by chelators. Aβ (10 ng/well in buffered saline) aggregation was induced by addition of metals (5 μM) or acidic conditions (pH 5.5). Aggregates were transferred to a 0.2 μ nylon membrane by filtration. The aggregates were then washed (200 μl/well) with TBS alone, TBS containing 2 μM EDTA or TBS with 2 μM clioquinol. The membrane was then fixed, probed with anti-Aβ monoclonal antibody 6E10 and developed for exposure to ECL-film. FIG. 23 shows the relative signal as determined by densitometric analysis of the ECL-film, calibrated against known amounts of the peptide. Values are expressed as a % of Aβ signal remaining on the filter after washing with TBS alone. Clioquinol is hydrophobic, so that the reagent must first be solubilized in an organic solvent, and then partitioned into the aqueous buffer according to established protocols.

Like EDTA (FIG. 17), clioquinol significantly resolubilized precipitated Aβ. $Cu^{2+}$ partially precipitates $A\beta_{1-40}$ (Bush, A. I., et al., Science 268:1921 (1995)) at pH 7.4. EDTA (2 μM) resolubilized 35% of a $Zn^{2+}$-induced Aβ precipitate, 60% of a $Cu^{2+}$-induced precipitate, and 15% of a pH 5.5-induced precipitate. In contrast, clioquinol (2 μM) was more effective at resolubilizing the $Zn^{2+}$-and $Cu^{2+}$-induced Aβ precipitates (50%, and 85%, respectively), but was also ineffective at resolubilizing the pH 5.5 precipitate (10%). Since the aggregate at pH 5.5 is predominantly β-sheet (Wood, S. J. et al, J. Mol. Bio., 256:870–877 (1996)), these data indicate that the resolubilization of Aβ by clioquinol/EDTA is likely to be due to specific chelation effects.

Extraction of Aβ from Samples of AD-Affected Brains

Figure 24:
FIG. 24 shows extraction of $A\beta$ from brain tissue with clioquinol. Undiluted (100%) clioquinol is 1.6 $\mu$M. S1 and S2 represent two sequential extractions from AD-affected tissue.
Figure 24:

Next the ability of clioquinol to extract Aβ deposits from human brain was examined. It was found that, like other zinc chelators, clioquinol efficiently increases the resolubilization of Aβ, compared to the amount of Aβ resolubilized from the pellet fraction of brain homogenate by PBS alone. FIG. 24 shows the effect of clioquinol upon the extraction of Aβ from Aβ-affected brain. Fragments of prefrontal cortex from individual post-mortem samples with the histopathological diagnosis of AD were homogenized in PBS, pH 7.4, and then pelleted after centrifugation. The pellets were then washed with agitation twice for 30 minutes, 4° C., with PBS or PBS containing clioquinol (100%=0.8 μM clioquinol). The suspension was then pelleted (10,000 g for 30 minutes) and the supernatant removed (S1) for western blot analysis using Aβ-specific antibodies (illustrated). The pellet was treated a second time in this experiment with agitation and centrifugation, and the second supernatant (S2) analyzed. The data show typical results by western blot.

In agreement with earlier findings which showed that the optimal concentration of chelator for the extraction of Aβ is idiosyncratic from case to case, and that there is a paradoxical diminution of Aβ extraction when the chelator concentration rises above the optimum, it was found that optimal clioquinol concentrations for Aβ resolubilization vary in a similar manner (e.g., Specimen #1=0.08 μM, #2=0.8 μM). It was also observed that apparently dimeric Aβ was more frequently observed on SDS-PAGE (illustrated), and that in these cases (e.g., Specimen #2) the first wash did not resolubilize much Aβ, but the second wash was very efficient at resolubilizing the peptide. It was surmised that the pellet mass may be coated with adventitial, non-Aβ, proteins that are removed by the first wash, allowing the second treatment access to the Aβ collection. Indeed, further studies have shown that both sustained (for 16 hours) and repeated exposure to the chelator increases the resolubilization of Aβ significantly.

Figure 25A:
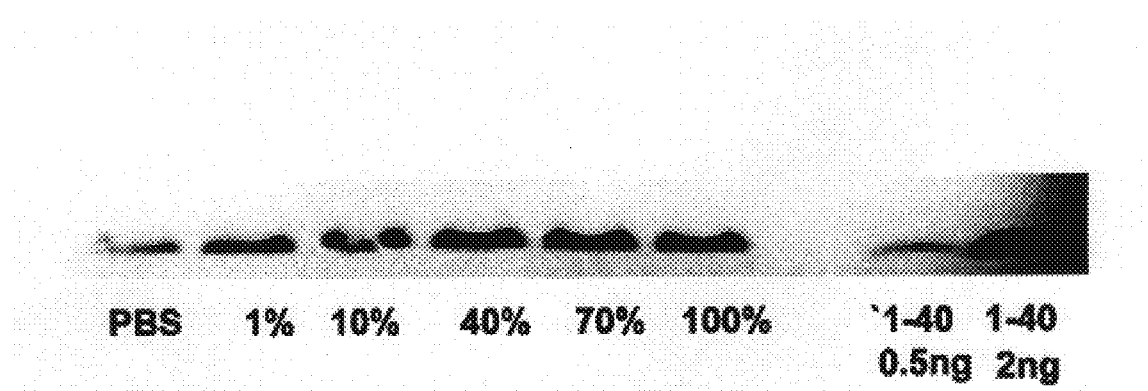
FIGS. 25A and 25B.
Figure 25B:
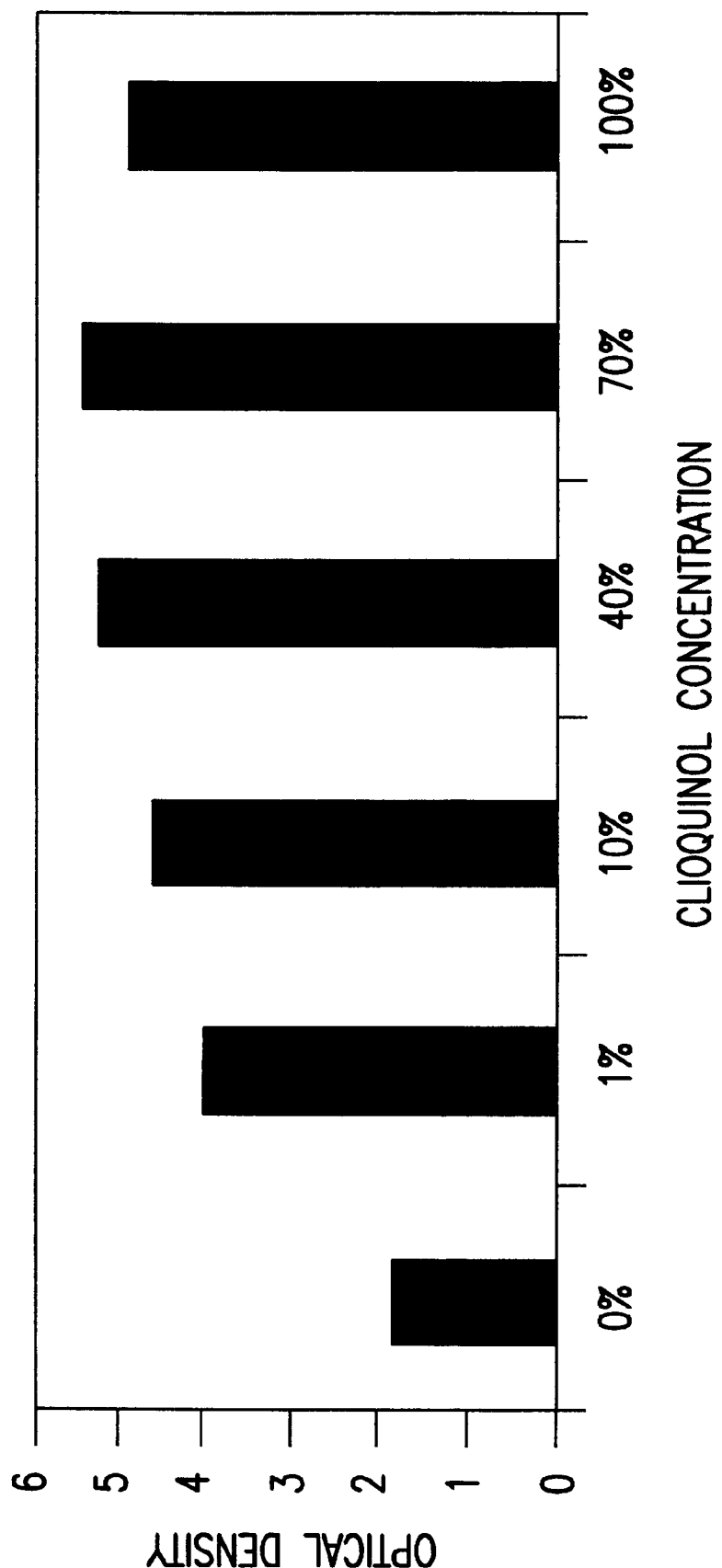

FIGS. 25A and 25B show the western blot and accompanying densitometric analysis of resolubilization of Aβ from AD-affected brain. FIG. 25A is a western blot showing the effect of clioquinol upon the resolubilization of Aβ from AD-affected brain. In this study, the brain specimen (from a different case than that of FIG. 24) was homogenized according to the protocols in FIG. 19. In this case a dose-dependent response to clioquinol was observed. Synthetic peptide standards that were used to calibrate densitometric quantification are shown in the two right-most lanes.

FIG. 25B is a chart showing densitometry performed upon the results in FIG. 25A, above. Proportional change in the amount of Aβ recovered in the extraction of Aβ by clioquinol from human brain is shown. As little as a 1% dilution of clioquinol in PBS (100%=0.8 μM) or 8 nM clioquinol is capable of doubling the recovery of Aβ in the soluble phase.

In sequential extraction experiments, as described above, clioquinol (1.12 μM) has been shown to result in a 2.5 fold increase in solubilization of Aβ relative to PBS alone (see FIGS. 25A and 25B). Significantly, the findings of the present invention show that very low (8 nM) concentrations of clioquinol may resolubilize more than twice the amount of Aβ compared to PBS buffer alone (see FIGS. 25A and 25B). This suggests that such low concentrations may be therapeutically effective in treating amyloidosis, preferably that occurring in AD-affected human subjects.

Example 7

Potentiation of Resolubilization of Amyloid from AD-Affected Brain Tissue

Aβ was extracted from cortical tissue obtained from three subjects with clinically and histopathologically confirmed Alzheimer's disease in the presence of 1.6 μM clioquinol (CQ), 2 mM bathocuproine (BC), CQ+BC or PBS. Soluble Aβ (ng/g tissue)was determined as described. Total Aβ was determined following formic acid extraction of otherwise untreated tissue.

Figure 26:
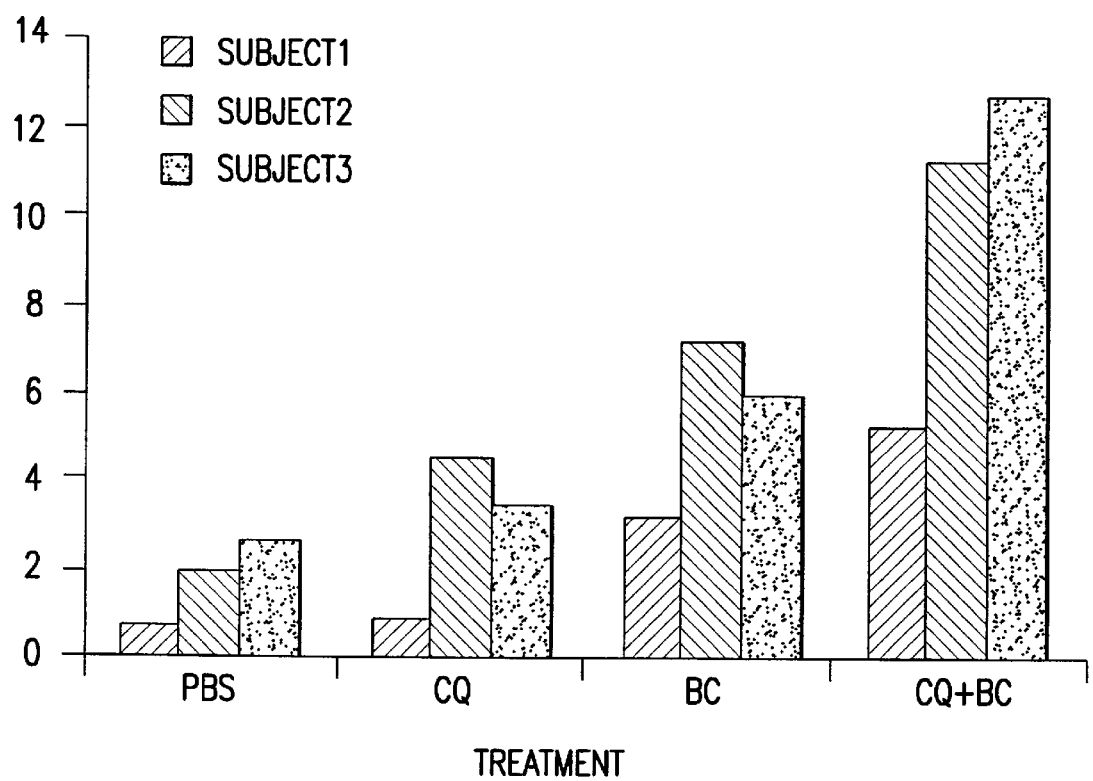
FIG. 26 is a graph showing the proportion of total Aβ extracted utilizing PBS buffer alone, clioquinol (CQ), bathocuproine (BC), or clioquinol together with bathocuproine (CQ+BC).

FIG. 26 illustrates the potentiation of Aβ resolubilization using clioquinol in combination with bathocuproine by graphically showing the proportion of total Aβ extracted. Table 4 below shows the data depicted in FIG. 26 and, in addition, shows each chelator or chelator combination in PBS buffer.

TABLE 4

Potentiation of Chelator-Promoted Aβ Solubilization

| Subject | PBS | CQ | BC | CQ + BC | CQ + PBS | BC + PBS | CQ + BC + PBS |
|---|---|---|---|---|---|---|---|
| 1 | 0.74 | 1.85 | 3.1 | 5 | 0.11 | 2.36 | 4.26 |
| 2 | 1.8 | 4.5 | 7.2 | 11.2 | 2.7 | 5.4 | 9.4 |
| 3 | 2.3 | 3.4 | 6 | 12.7 | 1.1 | 3.7 | 10.4 |

(% of total Aβ extracted)

The effect of clioquinol and bathocuproine combined is seen to be much more than additive. In subject 3, for example, the potentiated effect was over twice that of a simple additive effect (10.4 compared to 1.1 +3.7 or 4.8). These data suggest that combinations of clioquinol and bathocuproine may be particularly effective therapeutic combinations for the treatment of amyloidosis, in particular, the pathological Aβ-aggregation manifest in brains of those afflicted with Alzheimer's disease.

Example 8

Differential Effects of Chelation of Cerebral Aβ Deposits in AD-Affected Subjects Versus Age-Matched Controls and the Effect of Magnesium Experiments involving extraction of cerebral tissue from AD-affected subjects and non-AD, age-matched controls by chelation indicate different resolubilization responses of amyloid deposits between the two sample groups with regard to extraction by specific chelators.

Higher concentrations of chelators with relatively broad specificity (e.g. EGTA) result in less resolubilization of Aβ deposits. Experiments show that chelation of magnesium negatively affects resolubilization of Aβ deposits.

Materials and Methods

Cortical tissue was dissected from the frontal poles of frozen AD and age-matched normal brains for which histopathological and clinical documentation were provided. AD tissue was selected according to CERAD criteria (Mirra et al., *Neurology* 41:479–486 (1991)) with particular attention paid to the presence of neuritic plaques and neurofibrillary tangles. Histological examination of Aβ levels in normal specimens ranged from immunohistochemically undetectable to substantially present in the form of diffuse plaques.

Suitable quantities of gray matter from each subject were minced to serve as pools of homogenous tissue. Equal portions (0.5 g unless otherwise specified) were homogenized (Ika Ultaturax T-25, Janke and Kunkel, Staufen, Germany) for 3×30s periods at full speed with a 30 second rest between runs in 3 ml of ice-cold phosphate-buffered saline (PBS pH 7.4) containing a cocktail of protease inhibitors (Biorad, Hercules, Calif.—Note: EDTA was not included in the protease inhibitor mixture) or in the presence of chelators or metal ions prepared in PBS. To obtain the soluble fraction, the homogenates were centrifuged at 100,000×g for 30 min (Beckman J180, Beckman instruments, Fullerton, Calif.) and the supernatant collected in 1 ml aliquots and stored on ice or immediately frozen at −70° C. In each experiment, all protein was precipitated from 1 ml of supernatant from each treatment group using 1:5 ice cold 10% trichloracetic acid and pelleted in a bench top microfuge (Heraeus, Osteroder, Germany) at 10,000×g. The remaining pellet was frozen at −70° C.

The efficiency of the precipitation was validated by applying the technique to a sample of whole human serum, diluted 1:10, to which had been added 2 μg of synthetic $A\beta_{1-40}$ or $A\beta_{1-42}$ (W. Keck Laboratory, Yale University New Haven, Conn.). Protein in the TCA pellet was estimated using the Pierce BCA kit (Pierce, Rockford, Ill.). The total Aβ load of unextracted cortex was obtained by dissolving 0.5 g of grey matter in 2 ml of 90% formic acid, followed by vacuum drying and neutralization with 30% ammonia.

Precipitated protein was subjected to SDS polyacrylamide gel electrophoresis (SDS-PAGE) on Novex pre-cast 10–20% Tris-Tricine gels followed by Western transfer onto 0.2 μm nitrocellulose membrane (Biorad, Hercules, Calif.). Aβ was detected using the WO2, G210 or G211 monoclonal antibodies (Ida, N., et al., *J. Biol. Chem.*, 271:22908 (1996)) in combination with HRP-conjugated rabbit anti-mouse IgG (Dako, Denmark), and visualized using chemiluminescence (ECI, Amersham life Science, Little Chalfont, Buckinghamshire, UK). Each gel included two or more lanes containing known quantities of synthetic Aβ which served as internal reference standards. Blot images were captured by a Relisys scanner with transparency adapter (Teco Information Systems, Taiwan, ROC) and densitometry conducted using the NIH Image 1.6 program (National Institutes for Health, USA. Modified for PC by Scion Corporation, Frederick, Md.), calibrated using a step diffusion chart. For quantitation of Aβ in brain extracts, the internal reference standards of synthetic Aβ were utilized to produce standard curves from which values were interpolated.

Figure 27:
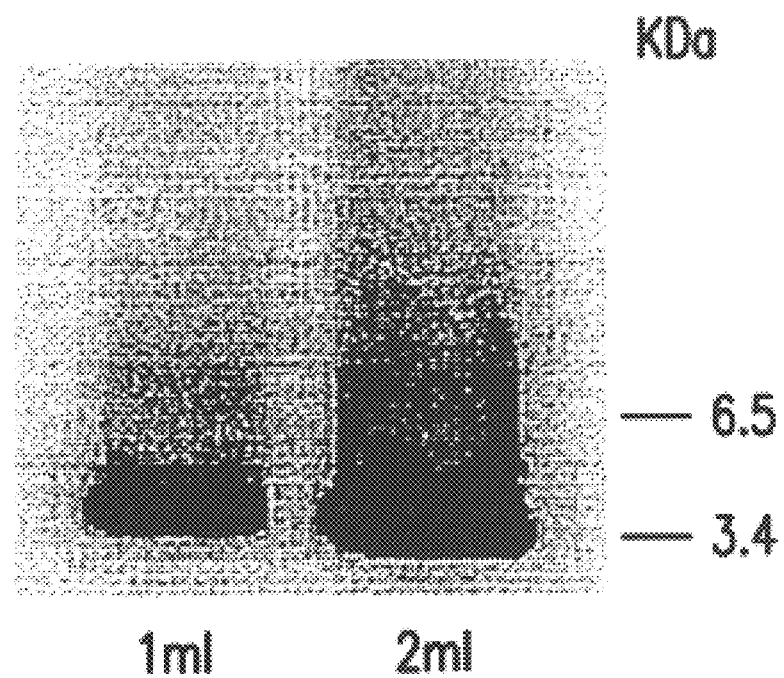
FIG. 27 shows that extraction volume affects Aβ solubilization.

In the experiments corresponding to the results shown in FIG. 27, duplicate 0.2 g samples of AD cortical tissue were homogenized and subjected to ultracentrifugation as described, but using either 1 ml or 2 ml of extraction buffer (PBS). Protein was precipitated from the entire supernatant and redissolved in 100 μl of sample buffer. Equal volumes of TCA-precipitated protein were subjected to Tris-Tricine SDS-PAGE and Aβ was visualized as described above.

Figure 28A:
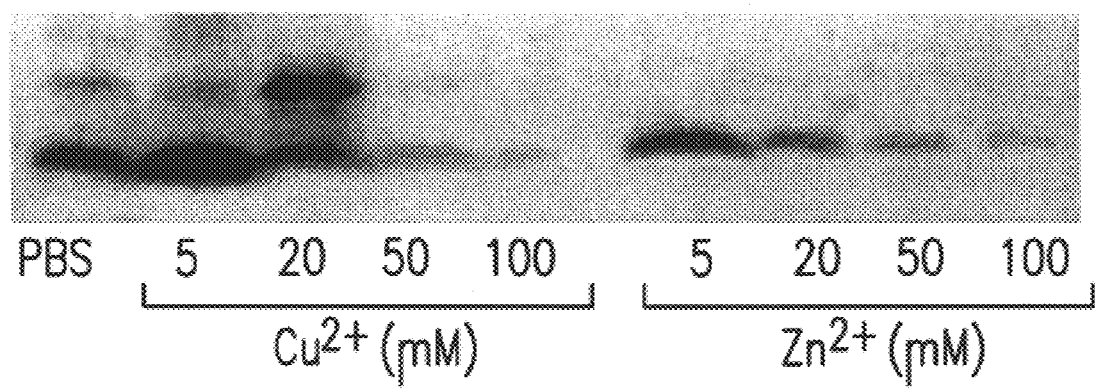
FIGS. 28A and 28B—FIG. 28A shows the effect of metals upon the solubility of brain-derived Aβ: copper and zinc can inhibit the solubilization of Aβ.

In the experiments corresponding to the results shown in FIG. 28A, 0.2 g specimens of frontal cortex from AD brain were homogenized in the presence of 2 ml of PBS or varying concentrations of $Cu^{2+}$ ($Cu(SO4)_2$) or $Zn^{2+}$ ($Zn(SO4)_2$). Aβ in the high speed supernatant was visualized as described above.

Figure 28B:
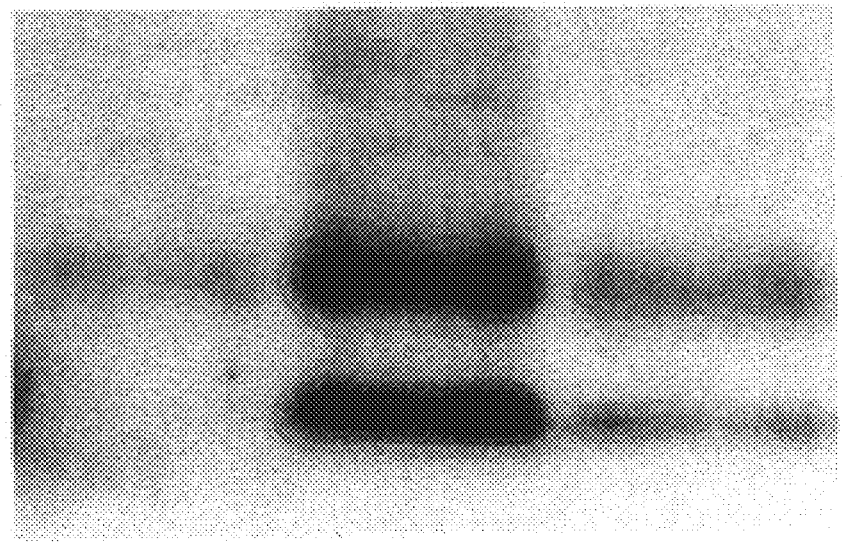

In the experiments corresponding to the results shown in FIG. 28B, 0.2 g specimens of frontal cortex from AD brain were homogenized in the presence of 2 ml or PBS or 2 mM EGTA. The homogenates were spun at 100,000×g for 30 min and the supernatant discarded. The remaining (metal depleted) pellets were rehomogenized in a further 2 ml of either PBS alone EGTA alone, 2 mM $Mg^{2+}$ ($Mg(Cl)_2\cdot 6H_2O$) in PBS or 2 mM $Ca^{2+}$ ($CaCl_2\cdot 2H_2O$) in PBS and the homogenate subjected to ultracentrifugation. Aβ in the soluble fraction was visualized as described above.

In the experiments corresponding to the results shown in FIGS. 29A and 29B, frontal cortex from AD (n=6) and age-matched, amyloid-positive (n=5) subjects were treated with PBS, TPEN, EGTA or BC (0.1 mM and 2 mM) and soluble Aβ assessed as described above.

In the experiments corresponding to the results shown in FIG. 30, representative AD (left panels) and aged-matched control specimens (right panels) were prepared as described in PBS or 5 mM BC. Identical gels were run and Western blots were probed with mAbs WO2 (raised against residues 5–16, recognizes $A\beta_{1-40}$ and $A\beta_{1-42}$), G210 (raised against residues 35–40, recognizes $A\beta_{1-40}$), or G211 (raised against residues 35–42, recognizes $A\beta_{1-42}$) (See Ida, N., et al., *J. Biol. Chem.*, 271:22908 (1996)).

Results and Discussion

To further explore the involvement of metal ions in the deposition and architecture of amyloid deposits, the inventors extracted brain tissue from histologically-confirmed AD-affected subjects and from subjects that were age-matched to AD-affected subjects but were not clinically demented (age-matched controls, "AC") in the presence of a variety of chelating agents and metals. Chelators were selected which displayed high respective affinities for zinc and/or copper relative to more abundant metal ions such as calcium and magnesium. See Table 5 below.

TABLE 5

Stability constants of metal chelators

| | Ca | Cu | Mg | Fe | Zn | Al | Co |
|---|---|---|---|---|---|---|---|
| EGTA | 10.86 | 17.57 | 5.28 | 11.8 | 12.6 | 13.9 | 12.35 |
| TPEN | 3 | 20.2 | n/a | 14.4 | 15.4 | n/a | n/a |
| BC | n/a | $Cu^{2+}$ 6.1 $Cu^+$ 19.1 | n/a | n/a | 4.1 | n/a | 4.2 | logK10 where K=[Metal.Ligand]/[Metal][Ligand]. From: NIST database of critically selected stability constants for metal complexes Version 2.0 1995.

A series of titration curves were prepared to determine the chelator concentration at which maximal response was obtained. In these experiments, selected chelators were limited to EGTA, TPEN and BC. FIGS. 19A–C show that chelators affect the solubilization of Aβ in a dose-dependent manner.

It was found that EGTA and TPEN elicited a significant enhancement in solubilization of Aβ in a pattern of response typified by peak values at or near 0.004 mM and 0.1 mM, and lower values at concentrations in between. Both chelators were increasingly ineffective at concentrations over 1 mM, and at 2 mM, FGTA virtually abolished the signal for Aβ. In contrast, BC elicited a typical concentration-dependent response with no decline in effectiveness in the low millimolar range even when extended to 20 mM. Total TCA-precipitated protein in the supernatant was assayed and found to be unaffected by either chelator kind or concentration.

Recent findings have demonstrated the presence of neurotoxic dimers in the soluble (Kuo, Y-M., el al., *J. Biol. Chem.* 271:4077–81 (1996)) and insoluble (Roher, A. E., et al., *Journal of Biological Chemistry* 271:20631–20635 (1996); Giulian, D. et al., *J. Nettrosci.*, 16:6021–6037 (1996)) fractions of Aβ extracts of the brains of AD individuals. FIG. 21 shows that chelator-promoted solubilization of Aβ elicits SDS-resistant dimers. Under the preparation conditions used, SDS-registant dimers were not generally observed in the extracts with PBS alone. Dimers were found to appear in response to chelator-promoted solubilization of Aβ however.

The signal for dimeric Aβ was frequently disproportionate to that of monomeric Aβ and the ratio varied with both the type and concentration of chelator used (FIG. 21). In contrast, when synthetic $Aβ_{1-40}$ was run under identical conditions, the monomer:dimer ratio reflected a predictable and reproducible concentration-dependent relationship. These data suggest that the dimers observed in extracts of human brain are predominantly an intermediate structural unit generated by the dissolution of amyloid, resulting in turn from the sequestration of metals by chelating agents.

FIG. 28A shows the effect of metals upon the solubility of brain-derived Aβ. Precipitation of Aβ was induced by adding either copper or zinc to unchelated extracts. The resulting signal for soluble Aβ was attenuated, the threshold concentration being between 20 and 50 $\mu$M for copper and between 5 and 20 $\mu$M for zinc. At concentrations greater than 100 $\mu$M solubility was abolished. Interestingly, at lower concentrations of copper there appears to be a transitional stage where Aβ is present in the dimeric form prior to complete aggregation, mirroring the intermediate stage dimers elicited by chelator-mediated solubilization.

In order to confirm that the chelators were effective at sequestering metals at the concentrations employed in these experiments, ICP was used to determine the residual levels of several metals in the post-centrifugation pellets retained from the experiment described in FIGS. 19A–19C. Of the six metals tested, zinc levels were reduced by TPEN in a dose dependent manner, whereas EGTA affected calcium and magnesium, particularly at higher concentrations. See Table 6 below.

TABLE 6

Residual Metal Levels in Post-Centrifugation (Extracted) Pellets

|  |  | Mg (mg/kg) | Al (mg/kg) | Ca (mg/kg) | Fe (mg/kg) | Zn (mg/kg) | Cu (mg/kg) |
|---|---|---|---|---|---|---|---|
|  | PBS | 202 | 36 | 573 | 411 | 60 | 13 |
| TPEN (mM) | 0.004 | 147 | 22 | 322 | 317 | 28 | 10 |
|  | 0.001 | 192 | 34 | 490 | 512 | 42 | 12 |
|  | 0.04 | 201 | 22 | 956 | 322 | 22 | 10 |
|  | 0.1 | 200 | 60 | 708 | 389 | 21 | 12 |
|  | 2.0 | 200 | 148 | 419 | 376 | 19 | 11 |
|  | 5.0 | 205 | 16 | 377 | 307 | 17 | 10 |
|  | PBS | 223 | 52 | 1186 | 266 | 45 | 11 |
| EGTA (mM) | 0.004 | 228 | 73 | 795 | 247 | 53 | 11 |
|  | 0.001 | 237 | 43 | 862 | 281 | 49 | 12 |
|  | 0.04 | 247 | 104 | 1402 | 438 | 71 | 13 |
|  | 0.01 | 213 | 61 | 675 | 272 | 54 | 13 |
|  | 2.0 | 191 | 62 | 519 | 238 | 27 | 13 |
|  | 5.0 | 168 | 27 | 455 | 230 | 18 | 12 |
| BC (mM) | 0.004 | 234 | 33 | 489 | 231 | 47 | 12 |
|  | 0.001 | 225 | 88 | 1306 | 275 | 47 | 13 |
|  | 0.04 | 226 | 38 | 753 | 248 | 56 | 15 |
|  | 0.01 | 223 | 73 | 762 | 256 | 49 | 13 |
|  | 2.0 | 254 | 42 | 1602 | 271 | 49 | 14 |
|  | 5.0 | 238 | 38 | 912 | 249 | 53 | 15 |

Metal levels were measured in 10 AD specimens treated with 0.1 mM TPEN. See Table 7 below. The observed increase in extractable Aβ correlated with significant depletion in zinc in every case and to a lesser extent, copper, when compared with PBS-treated tissue. No other metal tested was significantly influenced by treatment at this concentration.

TABLE 7

Residual Metal Levels (Based on 10 AD Specimens)

|  | Zn | Cu | Fe | Ca | Mg | Al |
|---|---|---|---|---|---|---|
| PBS | 50.7 | 11.9 | 227 | 202 | 197 | 44 |
| (+/−SEM) | (4.9) | (1.5) | (28.8) | (28.3) | (39.1) | (46.2) |
| TPEN | 33.2 | 9.8 | 239 | 210 | 230 | 65 |
| (+/−SEM) | (4.1) | (1.7) | (31.7) | (37.0) | (39.2) | (45.0) |

Given the precipitous decline in extractable Aβ observed when employing high concentrations of TPEN or EGTA (see FIG. 9), it was hypothesized that magnesium or calcium might also have a significant role in the Aβ solubility equilibrium. Magnesium or calcium added to the homogenization buffer produced no appreciable alteration in soluble Aβ. However, using an extract previously depleted of metals by high levels of EGTA, the addition of magnesium, and to a much lesser extent calcium, led to resolubilization of the precipitated Aβ. FIG. 28B shows that Aβ solubility in metal-depleted tissue samples is restored by supplementing with magnesium.

Mindful of the high variability observed between individual subjects, 6 AD and 5 aged-matched control brains were chosen at random to determine if the observed phenomena were broadly applicable. These specimens were subjected to chelation treatment at selected concentrations of 0.1 or 2.0 mM or with PBS alone. FIG. 29A shows that patterns of chelator-promoted solubilization of Aβ differ in AD and aged, non-AD tissue. The chelator-promoted solubilization of Aβ from AD brains represented an increase of up to 7-fold over that seen with PBS alone; the mean increase for BC being around 4 fold, and that for TPEN around 2 fold. Treatment with EGTA at 2 mM always produced a diminution in Aβ signal below that observed for the PBS control (See FIG. 29B).

The effects observed with non-demented, aged-matched controls were similar with respect to EGTA and TPEN. However, it is noteworthy that the effect of BC was much reduced. In some cases (FIG. 29A, lower panel), BC treatment caused an attenuation in soluble Aβ suggesting that the amyloid deposits in AD-affected brain respond to this chelator in a different fashion than the deposits predominating in non-demented elderly brain.

For each subject in the experiments of FIGS. 29A and 29B, the extractable Aβ was derived and calculated as a proportion of the total pre-extraction Aβ load See Table 8 and 9 below.

TABLE 8

AD-Affected Tissue

| AD | 1 | 2 | 3 | 4 | 5 | 6 | X | +/− SEM | X C/PBS |
|---|---|---|---|---|---|---|---|---|---|
| Total Aβ (μg/g) | 10.8 | 77.0 | 80.3 | 6.0 | 14.4 | 16.8 | 43.0 | 14.1 | |
| PBS μg/g | 0.74 | 1.39 | 1.04 | 0.07 | 3.0 | 0.06 | 1.05 | 0.44 | |
| (% of total) | (0.1) | (1.8) | (1.3) | (1.1) | (2.1) | (0.4) | (1.2) | (0.3) | |
| TPEN 2 mM μg/g | 0.21 | 3.40 | 1.80 | 5.50 | 5.00 | 0.28 | 2.73 | 0.85 | 2.60 |
| (% of total) | (0.2) | (4.4) | (2.25) | (9.2) | (3.5) | (1.75) | (4.6) | (0.9) | |
| BC2 mM μg/g | 0.31 | 5.54 | 3.62 | 6.05 | 6.03 | 0.54 | 4.10 | 0.86 | 3.90 |
| (% of total) | (0.3) | (7.2) | (4.5) | (10.0) | (4.2) | (3.4) | (5.4) | (1.2) | |

TABLE 9

Age-Matched Control Tissue

| AC | 1 | 2 | 3 | 4 | 5 | X | +/− SEM | X C/PBS |
|---|---|---|---|---|---|---|---|---|
| Total Aβ (μg/g) | 0.7 | 4.2 | 2.7 | 3.2 | 3.6 | 2.8 | 0.60 | |
| PBS μg/g | 0.17 | 0.13 | 0.18 | 0.10 | 0.66 | 0.25 | 0.10 | |
| (% of total) | (25.0) | (3.1) | (6.7) | (3.3) | (18.3) | (11.3) | (4.4) | |
| TPEN 2 mM μg/g | 0.22 | 0.38 | 0.26 | 0.09 | 1.06 | 0.40 | 0.17 | 1.6 |
| (% of total) | (32.0) | (9.0) | (9.7) | (3.0) | (29.5) | (16.7) | (5.1) | |
| BC 2 mM μg/g | 0.03 | 0.24 | 0.29 | 0.08 | 0.98 | 0.32 | 0.16 | 1.28 |
| (% of total) | (5) | (5.7) | (11.0) | (2.6) | (27.2) | (10.3) | (4.6) | |

Total Aβ for AD brains ranged from 6–80 μg/g wet weight tissue. The percentage of Aβ extractable (one extraction/centrifugation sequence) ranged from 0.33–10%. The corresponding values for aged-matched control brains were 0.68–4.2 μg/g total Aβ and 2.6–29.5% extractable.

In order to further investigate these different responses to chelators, triplicate blots of AD tissue and control tissue which displayed cerebrovascular and diffuse amyloid deposits were compared. FIG. 30 shows that chelation promotes the solubilization of $A\beta_{1-40}$ and $A\beta_{1-42}$ from AD and non-AD tissue. Using 3 different monoclonal antibodies, attempts to detect whether any particular species of Aβ were selectively affected by chelation were performed. Both $A\beta_{1-40}$ and $A\beta_{1-42}$ were liberated by chelation, however the dimeric form of $A\beta_{1-40}$ in both AD and control tissue predominated. As reported by Roher, A. E., et al., PNAS 90: 10,836–10,840 (1993), the predominant form of cerebrovascular amyloid is $A\beta_{1-42}$. Somewhat surprisingly, the dimeric form of this highly aggregating species is absent in the (control) tissue in which it is most favored.

It has recently been reported that the zinc-dependent Insulin Degrading Enzyme (IDE) has significant Aβ cleavage activity (Perez et al., Proc Soc. for Neuroscience 20: Abstract 321.13 (1997))$_{23}$. In the experiments presented here, the disassembly of amyloid is reflected in the intermediate dimeric species which result from conversion between soluble and insoluble forms. Thus, simple inhibition of catalytic enzyme activity cannot account for the observed increase in soluble Aβ. However, in the event that a proportion of the chelator-mediated augmentation of Aβ solubilization was due to inhibition of this enzyme, homogenizations were conducted both in the presence of 1 mM n-ethyl amimide (NEM), a potent inhibitor of IDE, and at 37° C. No enhancement of Aβ signal was observed above that of PBS alone for NEM , nor was there any diminution of signal after incubation at 37° C.

Discussion

Metal chelators offer a powerful tool for investigating the role of metals in the complex environment of the brain, however the strengths of these compounds may also define their limitations. The broad metal affinities of most chelators make them rather a blunt instrument. Attempts were made to sharpen the focus of the use of chelators by selecting chelators with a range of affinities for the metals of interest. These differences may be exploited by appropriate dilution, thereby favoring the binding of the relatively high affinity ligand (metal for which the chelator has the highest affinity).

The dilution profiles exhibited by EGTA and TPEN possibly reflect a series of equilibria between different metal ligands and the chelator, whereby the influence of abundant but low affinity metals is observed at high chelator concentrations and that of the high affinity, but more scarce, metals predominates at low concentrations of chelator. In the case of Aβ itself, this explanation is further complicated by the presence of low and high affinity binding sites for zinc (and copper) (Bush, A. I. et al., J. Biol. Chem., 269:12152–12158 (1994)).

Bathocuproine with its low affinity for metals other than $Cu^+$ is effective at solubilizing Aβ through a dilution range over 3 orders of magnitude, and interestingly, does not diminish in effectiveness at the highest levels tested. The particular affinity of BC for $Cu^+$ has been exploited to demonstrate that in the process of binding to APP, $Cu^{2+}$ is reduced to $Cu^+$ resulting in the liberation of potentially destructive free radicals (Multhaup, G., et al., Science 271:1406–1409 (1996)). It has been shown that Aβ has a similar propensity for reducing copper with consequent free radical generation (Huang, X., et al., J. Biol. Chem. 272:26464–26470 (1997)).

Although the predicted reduction in copper in extraction pellets treated with BC has not been demonstrated, it is possible that the ratio of $Cu^{2+}$ to $Cu^+$ has been affected. At this stage, however, the means to evaluate the relative contributions of divalent and reduced forms to the total copper content of such extraction pellets are not available.

In addition to their primary metal binding characteristics, chelators are a class of compounds which vary in hydrophobicity and solubility. Their capacity to infiltrate the highly hydrophobic amyloid deposits may therefore be an important factor in the disassembly of aggregated Aβ. It is also possible that the chelators are also acting to liberate intracellular stores of Aβ in vesicular compartments as metal-bound aggregates. Preliminary data from our laboratory indicates that this may be the case with platelets.

The variability between subjects is consistent, reflecting the heterogeneity of the disease in its clinical and histopathological expression. Despite this, a consistent pattern of response to the actions of chelators by tissue from both AD and non-AD subjects is observed. This universality of the phenomenon of chelator-mediated solubilization is strongly suggestive that metals are also involved in the assembly of amyloid deposits in normal individuals, although the dissimilar patterns of response suggest that different mechanisms are operating in the disease and non-pathological states.

On the basis of the evidence presented here and the in vitro data, it is proposed that zinc functions in the healthy individual to promote the reversible aggregation of Aβ, counteracted by magnesium acting to maintain Aβ solubility. Further, the disease state is characterized by an unregulated interaction with copper resulting in the generation of free radicals.

A functional homoeostatic mechanism implies equilibrium between intracellular copper and zinc (and perhaps other metals) normally present in trace amounts, for which Aβ has strong affinity, and more abundant metals which bind less strongly to Aβ. Zinc is of particular interest because the anatomical distribution of zinc correlates with the cortical regions most susceptible to amyloid plaque formation (Assaf, S. Y. & Chung, S. H., *Nature*, 308:734–736 (1984)).

It has recently been demonstrated (Huang, X., et al., *J. Biol. Chem.* 272:26464–26470 (1997)) that zinc-promoted aggregation of synthetic Aβ is reversible by the application of EDTA. The tightly-regulated neurocortical zinc transport system might provide a physiological parallel for this chelator-mediated disaggregation by moving zinc quickly in and out of the intraneuronal spaces.

Copper, while binding less avidly to Aβ than zinc (Bush, A. I., et al., *J. Biol. Chem.* 269:12152–12158 (1994)) has greater potential to inflict damage via free radical generation, resulting polymers are not reversible (see Example 10, below). Slight alterations in the transportation and/or metabolism of metals resulting from age-related deterioration of cellular processes may provide the environment for a rapid escalation of metal-mediated Aβ accretion which eventually overwhelms regulatory and clearance mechanisms. In describing a mechanism for Aβ homeostasis this model for amyloid deposition implies a possible physiological role for Aβ whereby aggregation and disaggregation may be effected through regulation or cortical metal levels and that the predominantly sporadic character of AD reflects individual differences in the brain milieu. Such a mechanism by no means rules out other genetic, environmental, inflammatory or other processes influencing the progression of the disease. Furthermore, in demonstrating the effectiveness of chelators in solubilising amyloid, it is suggested herein that agents of this type are useful for therapeutic or prophylactic use in AD.

Example 10

Formation of SDS-Resistant Aβ Polymers

The cause for the permanent deposition of Aβ in states such as Alzheimer's Disease (AD) and Down's Syndrome (DS) are unknown, but the extraction of Aβ from the brains of AD and DS patients indicates that there are forms of Aβ that can be resolubilized in water and run as a monomer on SDS-PAGE (Kuo, Y-M., et al., *J. Biol. Chem.* 271:4077–4081 (1996); see also Example 9 above), and forms that manifest SDS-, urea- and formic acid-resistant polymers on PAGE (Masters, C. L. et al., *Proc. Natl. Acad. Sci. USA* 82:4245–4249 (1985); Dyrks, T., et al., *J. Biol. Chem.* 267:18210–18217 (1992); Roher, A. E., et al., *Journal of Biological Chemistry* 271:20631–20635 (1996). Thus, the extraction of SDS-resistant Aβ polymers from plaques implicates polymerization as a pathogenic mechanism that promotes the formation of AD amyloid.

The exact mechanism underlying the formation of SDS-resistant polymeric Aβ species remains unresolved. Recently, we found that Aβ reduces both $Cu^{2+}$ and $Fe^{3+}$ (Huang, X., et al., *J. Biol. Chem.* 272:26464–26470 (1997)), providing a mechanism whereby a highly reactive species could promote the modification of proteins via an oxidative mechanism. In this study we test the ability of $Cu^{2+}$ and $Fe^{3+}$ to promote SDS-resistant Aβ polymerization.

Materials and Methods

Human $A\beta_{1-40}$ peptide was synthesized, purified and characterized as described above. Rat $A\beta_{1-40}$ was obtained from Quality Control Biochemicals, Inc. (Hopkinton, Mass.). Peptides were analyzed and stock solutions prepared as described above.

As above, electronic images captured using the Fluoro-S Image Analysis System (Bio-Rad, Hercules, Calif.) were analyzed using Multi-Analyst Software (Bio-Rad, Hercules, Calif.). This chemiluminescence image analysis system is linear over 2 orders of magnitude and has comparable sensitivity to film.

Human AD derived SDS-resistant polymers were solubilized in formic acid, and then dialyzed with 5 changes of 100 mM ammonium bicarbonate, pH 7.5. The solubilized peptide was then used for subsequent chelation experiments.

Results and Discussion

The generation of SDS-resistant Aβ polymers by metal ions was tested by incubating $Cu^{2+}$ (30 μM) or $Zn^{2+}$ (30 μM) at pH 6.6, 7.4 and 9.0 with $A\beta_{1-40}$. As shown in FIG. 9, Western blot analysis of samples incubated with $Cu^{2+}$ and run under SDS denaturing and β-mercaptoethanol reducing conditions revealed an increase in dimeric, trimeric and higher oligomeric Aβ species over time. The dimer and trimer had molecular weights of approximately 8.5 kD and 13.0 kD, respectively. Image analysis indicated 42% and 9% conversion of the monomer to dimer and trimer, respectively, in samples incubated at pH 7.4 after 5 d. The conversion of monomer to the dimer and trimer was 29% and 2%, respectively, at pH 6.6 after 5 d.

In contrast, changes in [$H^+$] alone did not induce SDS-resistant $A\beta_{1-40}$ polymerization. Less than 4% of the peptide was converted to the SDS-resistant dimer after 5 d in samples incubated at pH 6.6, 7.4 or 9.0, most likely as a result of contaminating $Cu^{2+}$ in the buffer and Aβ solutions. $Cu^{2+}$ contamination of chelex-treated PBS was up to 0.5 μM as determined by ion coupled plasma-atomic emission spectroscopy (ICP-AES). Although $Zn^{2+}$ induces rapid aggregation of $A\beta_{1-40}$ (Bush, A. I., et al., *J. Biol. Chem.* 268:16109 (1 993); Bush, A. I., et al., *J. Biol. Chem.* 269:12152 (1994); Bush, A. I., et al., *Science* 265:1464–1467 (1994); Bush, A. I., et al., *Science* 268:1921–1922 (1995); Atwood et al., submitted; Huang, X. et al., *J. Biol. Chem.* 272:26464–26470 (1997)), it did not induce SDS-resistant Aβ polymerization (FIG. 9) as previously reported (Bush, A. I., et al., *Science* 268:1921–1922 (1995)).

$A\beta_{1-42}$ is the predominant species found in amyloid plaques (Masters, C. L. et al., *Proc. Natl. Acad. Sci. USA* 82: 4245 (1985); Murphy, G. M., et al., *Am. J. Pathol.* 144:1082–1088(1994); Mak, K., et al., *Brain Res.* 667:138–142 (1994); Iwatgubo, T., et al., *Ann. Neurol.* 37:294–299 (1995); Mann et al., *Ann. Neurol.* 40:149–156 (1996)). Therefore, the ability of $A\beta_{1-40}$ and $A\beta_{1-42}$ to form SDS-resistant polymers was compared.

In contrast to $Cu^{2+}$-induced SDS-resistant $A\beta_{1-40}$ polymerization over days, SDS-resistant $A\beta_{1-42}$ polymerization occurred within minutes in the presence of $Cu^{2+}$ (FIG. 31A). Unlike $A\beta_{1-40}$ where $Cu^{2+}$ induces the formation of a SDS-resistant dimeric species first, $A\beta_{1-42}$ initially forms an apparent trimer species in the presence of $Cu^{2+}$. Over time, dimeric and higher polymeric species also appear in $A\beta_{1-42}$ incubations with $Cu^{2+}$ at both pH 7.4 and 6.6. The greater $Cu^{2+}$ induced $A\beta_{1-42}$ polymerization observed at pH 6.6 compared with pH 7.4 in samples incubated for 30 min. was reversed after 5 d. At pH 6.6, both $A\beta_{1-40}$ and $A\beta_{1-42}$ exist in an aggregated form within minutes. Therefore, the formation of these polymeric species occurs within $A\beta$ aggregates and the formation of SDS-resistant $A\beta$ polymers is independent of aggregation state (see below). Similar results were obtained using the monoclonal antibody 4G8.

Since redox active Fe (Smith, M. A., et al., *Proc. Natl. Acad. Sci. U,SA* 94:9866 (1997)) and ferritin (Grudke-Iqbal, I., et al., *Acta Neuropathol.* 81:105 (1990)) are found in amyloid lesions, experiments were performed to determine if Fe could induce SDS-resistant polymerization of $A\beta_{1-40}$ and $A\beta_{1-42}$ (FIG. 31A). $Fe^{3+}$ did not induce $A\beta_{1-40}$ polymerization above background levels with either peptide. The small increase in polymeric $A\beta_{1-40}$ and $A\beta_{1-40}$ in samples with no metal ions reflects a small contaminating concentration of $Cu^{2+}$.

The formation of amyloid plaques is not a feature of aged rats (Johnstone, E. M., et al., *Mol. Brain Res.* 10:229 (1991); Shivers et al., *EMBO J.*, 7:1365–1370 (1988)). To test whether rat $A\beta_{1-40}$ would form qD,-regiltant $A\beta$ polymers, rat $A\beta_{1-40}$ was incubated with $Cu^{2+}$ and $Fe^{3+}$ at pH 7.4 and 6.6 (FIG. 31B). Neither metal ion induced SDS-resistant $A\beta$ polymers (Huang, X. et al., *J. Biol. Chem.* 272:26464–26470 (1997)). The binding and reduction of $Cu^{2+}$ by rat $A\beta_{1-40}$ is markedly decreased compared to that of human $A\beta_{1-40}$ (Huang, X. et al., *J. Biol. Chem.* 272:26464–26470 (1997)). This result suggests that the generation of SDS-resistant $A\beta$ polymers is dependent upon the binding and reduction of $Cu^{2+}$ by $A\beta$.

Tests were performed to determine the concentration of $Cu^{2+}$ required to induce the formation of SDS-resistant $A\beta_{1-40}$ and $A\beta_{1-42}$ polymers. $A\beta_{1-40}$ and $A\beta_{1-42}$ were incubated with different $[Cu^{2+}]$ (0–30 $\mu$M) at pH 7.4 and 6.6 and the samples analyzed by Western blot and the signal quantitated using the Fluoro-S Image Analysis System (Bio-Rad, Hercules, Calif.) as previously described.

At pH 7.4, the increase in polymerization was barely detectable as $[Cu^{2+}]$ was increased from 0.5 to 1 $\mu$M, but under mildly acidic conditions (pH 6.6), SOS-resistant polymerization could be detected (over 3-fold increase in dimerization (Table 10A).

TABLE 10A

| $Cu^{2+}$-Induced SDS-Resistant Polymers of $A\beta_{1-40}$ | | | | | |
|---|---|---|---|---|---|
| [$Cu^{2+}$] | Monomer | Dimer | Trimer | Tetramer | Pentamer |
| pH 7.4 | | | | | |
| 0 | 96.8 | 3.2 | <0.1 | 0 | 0 |
| 0.5 | 94.8 | 4.9 | 0.3 | 0 | 0 |

TABLE 10A-continued

| $Cu^{2+}$-Induced SDS-Resistant Polymers of $A\beta_{1-40}$ | | | | | |
|---|---|---|---|---|---|
| [$Cu^{2+}$] | Monomer | Dimer | Trimer | Tetramer | Pentamer |
| 1 | 93.6 | 5.9 | 0.6 | 0 | 0 |
| 5 | 84.3 | 14.2 | 1.5 | 0 | 0 |
| 10 | 85.2 | 13.2 | 1.6 | 0 | 0 |
| 30 | 76.2 | 19.1 | 4.7 | 0 | 0 |
| pH 6.6 | | | | | |
| 0 | 97.9 | 2.1 | <0.1 | 0 | 0 |
| 0.5 | 97.6 | 2.2 | 0.2 | 0 | 0 |
| 1 | 92.6 | 7.3 | 0.1 | 0 | 0 |
| 5 | 90.1 | 9.8 | 0.1 | 0 | 0 |
| 10 | 79.4 | 16.1 | 4.5 | 0 | 0 |
| 30 | 74.5 | 13.2 | 12.2 | 0 | 0 |

A similar $Cu^{2+}$ concentration and pH dependent increase in SDS-resistant $A\beta_{1-42}$ polymers also was observed (Table 10B), but SDS-resistant polymerization occurred at much lower $[Cu^{2+}]$.

TABLE 10B

| $Cu^{2+}$-Induced SDS-Resistant Polymers of $A\beta_{1-42}$ | | | | | |
|---|---|---|---|---|---|
| [$Cu^{2+}$] | Monomer | Dimer | Trimer | Tetramer | Pentamer |
| pH 7.4 | | | | | |
| 0 | 76.61 | 0 | 16.0 | 5.5 | 1.9 |
| 0.5 | 70.7 | 0 | 20.5 | 6.2 | 2.5 |
| 1 | 64.9 | 0 | 23.6 | 7.4 | 4.0 |
| 5 | 56.1 | 0 | 31.8 | 8.7 | 4.1 |
| 10 | 55.1 | 0 | 30.3 | 10.3 | 4.3 |
| 30 | 57.1 | 0 | 31.1 | 8.3 | 4.2 |
| pH 6.6 | | | | | |
| 0 | 61.0 | 0 | 27.3 | 8.6 | 3.8 |
| 0.5 | 52.1 | 0 | 33.8 | 12.0 | 3.0 |
| 5 | 59.6 | 0 | 30.0 | 7.1 | 3.2 |
| 10 | 52.3 | 0 | 31.7 | 13.6 | 2.2 |

$A\beta_{1-40}$ polymerization was not detected with increasing $Fe^{3+}$ concentrations at any pH. Therefore, of the metal ions known to interact with $A\beta$, only $Cu^{2+}$, whose ability to aggregate and bind $Cu^{2+}$ under mildly acidic conditions is enhanced, is capable of inducing SDS-resistant $A\beta$ polymerization.

Oxygen radical mediated chemical attack has been correlated with an increase in protein and free carbonyls (Smith, C. D., et al., *Proc. Natl. Acad. Sci. USA* 88:10540 (1991); Hensley, K., et al., *J. Neurochem.* 65:2146 (1995); Smith, M. A., et al., *Nature* 382:120 (1996)) and peroxynitrite-mediated protein nitration (Good, P. F., et al., *Am. J. Pathol.* 149:21 (1996); Smith, M. A., et al., *Proc. Natl. Acad. Sci. USA* 94:9866 (1997)).

$A\beta$ is capable of reducing $Cu^{2+}$ and $H_2O_2$ is produced in solutions containing $A\beta$ and $Cu^{2+}$ or $Fe^{3+}$ (Huang, X. et al., *J. Biol. Chem.* 272:26464–26470 (1997)). As shown above, the generation of SDS-resistant $A\beta$ polymers in the order $A\beta_{1-42}>>A\beta_{1-40}>>$rat $A\beta_{1-40}$ in the presence of $Cu^{2+}$ correlates well with the generation of $Cu^+$ and reactive oxygen species (ROS; $OH^-$, $H_2O_2$ and $O_2^-$: Huang, X. et al., *J. Biol. Chem.* 272:26464–26470 (1997)) by each peptide.

The increased generation of SDS-resistant $A\beta$ polymers in the presence of $Cu^{2+}$ compared to $Fe^{3+}$ also was correlated with the generation of the reduced metal ions, respectively (Huang, X. et al., *J. Biol. Chem.* 272:26464–26470 (1997)). The increase in SDS-resistant $A\beta$ polymerization seen under mildly acidic conditions may be a result of the higher $[H^+]$ driving the production of $H_2O_2$ dismutated from $O_2^-$ with the subsequent generation of $OH^{\cdot}$ via Fenton-like chemistry inducing a modification of A$\beta$ that results in SDS-resistant A$\beta$ polymers (see FIG. 12, showing a schematic of the proposed mechanism of A$\beta$-mediated reduced metal/ROS production).

To confirm whether ROS were involved in the generation of SDS-resistant polymers, experiments were performed to determine whether Cu in the presence or absence of $H_2O_2$ could promote A$\beta$ polymerization (FIG. 32A). A similar level of A$\beta_{1-42}$ polymerization was observed in the presence of $Cu^{2+}$ or $Cu^+$, indicating that the reduced metal ion alone was not capable of increasing A$\beta$ polymerization. Likewise, polymerization of A$\beta_{1-42}$ in the presence of $H_2O_2$ was low and equivalent to control levels. However, the addition of $Cu^{2+}$ or $Cu^+$ to A$\beta$ in the presence of $H_2O_2$ induced a similar, marked increase in dimers, trimers and tetramers within 1 hour. After 1 day, higher molecular weight polymers (>18 kD) were generated (from the oligomers), with a subsequent reduction in the levels of monomer, dimer, trimer and tetramer only with the coincubation of $H_2O_2$ and $Cu^{2+}$.

Both the reduced and oxidized forms of Cu produced similar levels of polymerization in the presence of $H_2O_2$. In contrast, $Fe^{3+}$ of $Fe^{2+}$ did not induce as much polymerization as $Cu^{2+}$ in the presence of $H_2O_2$ after 1 day incubation (FIGS. 32A and 32B). Since $Fe^{3+}$ is not reduced as efficiently as $Cu^{2+}$ by A$\beta$ (Huang, X., et al., *J. Biol. Chem.*, 272:26464–26470 (1997)), and $Cu^+$ is rapidly converted to $Cu^{2+}$ in solution, these results suggest that the reduction reaction is required for the polymerization reaction to proceed.

It was confirmed that the reduction of $Cu^{2+}$ was required for generating SDS-resistant A$\beta$ polymerization by incubating A$\beta_{1-42}$ and $Cu^{2+}$ with and without bathocupoinedisulfonic acid (BC), a $Cu^+$ specific chelator (FIG. 32C). There was a marked decrease in polymerization, indicating that $Cu^+$ generation was crucial for the polymerization of A$\beta$. It is possible that the decreased polymerization may be due to chelation of $Cu^{2+}$ by BC, however given the low binding affinity of BC for $Cu^{2+}$ compared with A$\beta$, it seems likely that the chelation of $Cu^+$ by BC prevents it from inducing SDS-resistant A$\beta$ polymerization. Therefore, A$\beta$ may undergo a hydroxyl radical modification that promotes its assembly into SDS-resistant polymers.

If $H_2O_2$ is required for the polymerization reaction under physiological conditions, the removal of $H_2O_2$ and it's precursors $O_2$ and $O_2^-$ (Huang, X., et al., *J. Biol. Chem.*, 272:26464–26470 (1997)) should decrease SDS-resistant polymerization. To confirm that $H_2O_2$ generated in the presence of A$\beta$ and $Cu^{2+}$ was required for the polymerization reaction, A$\beta_{1-42}$ was incubated with or without $Cu^{2+}$ in the presence of TCEP (FIG. 33A). TCEP significantly reduced the level of polymerization in samples with and without $Cu^{2+}$ over 3 days. This indicates that the generation of $H_2O_2$ is required for the polymerization of A$\beta$.

To confirm that the generation of $O_2^-$ was required for SDS-resistant A$\beta$ polymerization, A$\beta_{1-42}$ was incubated with and without $Cu^{2+}$ at pH 7.4 and 6.6 under argon in order to decrease the reduction of molecular $O_2$ (FIG. 33B). Argon-purging of the solution markedly decreased A$\beta_{1-42}$ polymerization under each condition, indicating that the generation of ROS is required for the polymerization of A$\beta$.

Taken together, these results indicate that polymerization occurs as a result of Haber-Weiss chemistry where the continual reduction of $Cu^{2+}$ by A$\beta$ provides a species for the reduction of molecular $O_2$ and the subsequent generation of $O_2^-$, $H_2O_2$ and $OH^{\cdot}$. The binding and reduction of $Cu^{2+}$ by A$\beta$ is supported by the finding that the incubation of $Fe^{3+}$, $H_2O_2$ and ascorbic acid with A$\beta_{1-40}$ (FIG. 33A) and A$\beta_{1-42}$ does not induce SDS-resistant polymerization equivalent to $Cu^{2+}$ with $H_2O_2$ alone. Since ascorbic acid effectively reduces $Fe^{3+}$, the reduction of a metal ion that is not bound to A$\beta$ is insufficient to induce significant SDS-resistant polymerization.

The formation of SDS-resistant polymers of A$\beta$ by this metal-catalyzed oxidative mechanism strongly suggested that a chemical modification to the peptide backbone allows the formation of the polymer species. To test if the SDS-resistant polymers were covalently linked, SDS-resistant polymers generated by incubating A$\beta_{1-42}$ with $Cu^{2+}$ at pH 7 4 and 6.6, or A$\beta_{1-42}$ with $Cu^{2+}$ plus $H_2O_2$ were subjected to treatment with urea (FIG. 34A) and guanidine HCl, chaotrophic agents known to disrupt H-bonding. Urea and guanidine HCl did not disrupt the SDS-resistant polymers at 4.5 M, and only slightly at 9M, suggesting that the SDS-resistant polymers were held together by high-affinity bonds, but not hydrogen bonding alone. HPLC-MS analyses confirmed no covalent modification of the peptide and no evidence of intermolecular covalent crosslinking.

Since covalent and/or hydrogen bonding were not involved in polymer formation, experiments were performed to determine whether $Cu^{2+}$ coordination of the complex by ionic interactions was allowing for the formation of the SDS-resistant polymer species. To disrupt these ionic interactions, different chelating agents were added to a solution containing $Cu^{2+}$-induced A$\beta_{1-40}$ or A$\beta_{1-42}$ SDS-resistant polymers generated at pH 7.4 (FIGS. 34B and 34C).

All chelators significantly reduced the amount of A$\beta_{1-40}$ or A$\beta_{1-42}$ SDS-resistant polymers. EDTA was less effective in destabilizing the polymers, possibly due to its larger molecular mass, and lower affinity for $Cu^{2+}$. EDTA reduced the amount of A$\beta_{1-40}$ polymers, but increased the amount of A$\beta_{1-40}$ polymers at pH 7.4. This may be due to the fact that EDTA can enhance the redox potential of Cu under certain conditions.

$Cu^+$-induced SDS-resistant polymers generated at pH 6.6 were also disrupted with chelation treatment to a similar extent. These results suggest that the chelation of $Cu^{2+}$ away from A$\beta$ results in the disruption of the polymer complex and the release of monomer species. Thus, there is an absolute requirement for metal ions in the stabilization of the SDS-resistant polymer complex.

The SDS-resistant polymers generated with $Cu^{2+}$ are similar to those extracted from post-mortem AD brains (Roher, A. E., et al., *Journal of Biological Chemistry* 271:20631–20635 (1996)). To determine if these human oligomeric A$\beta$ species could be disrupted by metal chelators, TETA and BC were incubated with A$\beta$ oligomers extracted from human brain. FIG. 30E shows that both TETA and BC significantly increased the amount of monomer A$\beta$ in samples treated with these chelators. Although the increase in the amount of monomer was small, these results suggest that human oligomeric A$\beta$ species are partially held together with metal ions. Importantly, this result indicates the potential of chelation therapy as a means of reducing amyloidosis.

To examine whether conformational changes could disrupt the SDS-resistant polymers, solutions of SDS-resistant A$\beta_{1-42}$ polymers in the presence or absence of $Cu^{2+}$ were incubated with the u-helical promoting solvent system DMSO/HFIP, or under acidic conditions (pH 1) (FIG. 34D). These conditions reduced the amount of polymer compared to untreated controls at both pH 7.4 and 6.6, indicating that an alteration in the conformation of A$\beta_{1-42}$ to the $\alpha$-helical conformation could disrupt the strong Aβ-$Cu^{2+}$ ionic interactions. This provides indirect evidence that the polymer structures are likely to be in the more thermodynamically favorable β-sheet conformation, such as those found in neuritic plaques.

SDS-resistant Aβ polymers, such as that found in the AD-affected brain, are likely to be more resilient to proteolytic degradation and may explain the permanent deposition of Aβ in amyloid plaques. Incubation of SDS-resistant Aβ polymers with proteinase K resulted in complete degradation of both monomer and oligomeric Aβ species. Since protease treatment is incapable of digesting hard core amyloid, some form of covalent crosslinking of the peptide following its deposition may occur over time that prevents proteolytic digestion. This may explain the limited disruption of human SDS-resistant Aβ oligomers compared to the Cu-mediated SDS-resistant polymers generated in vitro.

Soluble $Aβ_{1-40}$ and $Aβ_{1-42}$ both exist in phosphate buffered saline as non-covalent dimers (Huang, X., et al., *J. Biol. Chem.* 272:26464–26470 (1997); and unpublished observations). Disruption of ionic and hydrogen bonding of Aβ in the soluble and aggregated forms (pH or $Zn^{2+}$) by the ionic detergent SDS results in the complete dissociation of Aβ into the monomer species as detected on SDS-PAGE (FIGS. 9, 28–30). The formation of SDS-resistant polymers of Aβ over time in the presence of $Cu^{2+}$ (FIGS. 9, 31A–31B, 32C) suggests that conformational or structural alterations allow for the formation of a thermodynamically more stable complex.

Although no covalent crosslinking between peptides was detected, it is possible that a covalent modification(s) takes place within the peptide backbone that allows for a high affinity association to form between the peptide and $Cu^{2+}$. Thus, a chemical modification to the peptide may increase the affinity of the polymer for $Cu^{2+}$ and the formation of a stable complex. Alternatively, the requirement for molecular oxygen suggests that Cu may be coordinated by oxygen or ROS in the formation of SDS-resistant polymers.

The formation of SDS-resistant polymers was dependent upon the binding and reduction of $Cu^{2+}$. The binding of $Cu^{2+}$ to Aβ was confirmed by the detection of $Cu^{2+}$ in both the monomer and dimer following SDS-PAGF. The [$Cu^{2+}$] of PVDF membrane containing the immobilized peptide species was measured by ICP-AES (unpublished observations; Huang, X., et al., *J. Biol. Chem.* 272:26464–26470 (1997)) and correlated with the generation of SDS-resistant polymers for each species.

$Cu^{2+}$ coordination between Aβ molecules was required in order to maintain the structure since chelation treatment disrupted the in vitro generated SDS-resistant polymer (FIGS. 34B–34E). Human SDS-resistant Aβ polymers also were disrupted with the Cu+ specific chelator BC indicating Cu coordination in the stabilization of these structures (FIG. 34E). Together with the fact that Cu specific chelators can extract more SDS-resistant Aβ polymers from AD brains in aqueous buffer (see Example 9), these results implicate $Cu^{2+}$ in the generation of SDS-resistant polymers in vivo.

$Fe^{3+}$ did not induce the formation of SDS-resistant polymers in vitro (FIGS. 31A) as previously reported except in the presence of excess $H_2O_2$ or ascorbic acid as previously reported (Dyrks, T., et al., *J. Biol. Chem.* 267:18210–18217 (1992); data not shown). Dyrks, T., et al. did, however observe significant increases in SDS-resistant polymerization with metal-catalyzed oxidation systems (Fe-hemin, Fe-hemoglobin or Fe-EDTA) in the presence of $H_2O_2$. The $Aβ_{1-42}$ used in their experiments was likely to be Cu-bound as it was extracted from a wheat germ expression system and already was present as SDS-resistant oligomers. Thus, it is possible that Cu-bound Aβ used in these experiments contributed to the increased SDS-resistant polymerization observed in the Fe-catalyzed oxidation systems. Although $Fe^{3+}$ is reduced by Aβ (Huang, X., et al., *J. Biol. Chem.* 272:26464–26470 (1997)), it is unable to effectively coordinate the complex like Cu (FIG. 32B).

$Fe^{2+}$ is found in much higher concentrations in the brains of AD patients compared with age-matched controls (Ehmann, W. D., et al., *Neurotoxicol.* 7.197–206 (1986); Dedman, D. J., et al., *Biochem. J.* 287:509–514 (1992); Joshi, J. G., et al., *Environ. Health Perspect.* 102:207–213 (1994)). This is partly attributable to the increased ferritin rich microglia and oligodendrocytes that localize to amyloid plaques (Grudke-lqbal, I., et al., *Acta Neuropathol.* 81:105 (1990); Conner, J. R., et al., *J. Neurosci. Res.* 31:75–83 (1992); Sadowki, M., et al., *Alzheimer's Res.* 1:71–76 (1995)).

Recently, redox active Fe was localized to amyloid lesions (Smith, M. A., et al., *Proc. Natl. Acad. Sci. U,SA* 94:9866 (1997). While Fe is normally sequestered by metalloproteins, this localization of ferritin-rich cells around amyloid deposits, and the very high concentrations of iron in amyloid plaques (Conner, J. R., et al., *J. Neurosci. Res.* 31:75–83 (1992); Markesbery, W. R. and Ehmann, W. D., "Brain trace elements in Alzheimer's disease," in Terry, R. D., el al., eds., *Alzheimer Disease*, Raven Press, New York (1994), pp. 353–368) suggests that reduced Fe released from ferritin and transferrin under mildly acidic conditions could be available for Fenton chemistry and the formation of SDS-resistant polymers. However, even in the presence of a Fe-ROS generating system (ascorbic acid, $H_2O_2$ and Fe) the generation of SDS-resistant Aβ polymers in vitro was low (FIG. 33A) and may be explained by $Cu^{2+}$ contamination of the buffers.

Interestingly, diffuse plaques, which may represent the earliest stages of plaque formation, are relatively free of ferritin-rich cells (Ohgami, T., et al., *Acta Neiropathol* 81:242–247 (1991)). Therefore, the accretion of iron in amyloid plaques may be a secondary response to the neurodegeneration caused by the reduction of $Cu^{2+}$ and the generation of ROS by Aβ and the formation of neurotoxic SDS-resistant Aβ polymers.

Structural differences between $Aβ_{1-40}$ and $Aβ_{1-42}$ may allow for the formation of a thermodynamically stable dimer in the case of $Aβ_{1-40}$ and trimer in the case of $Aβ_{1-42}$ (FIGS. 31A, 34B and 34C). Irrespective of this, the increased generation of SDS-resistant polymers by $Aβ_{1-42}$ compared to $Aβ_{1-40}$ is most likely explained by the increased ability of $Aβ_{1-42}$ to reduce Cu and generate ROS. Since the addition of exogenous $H_2O_2$ to $Aβ_{1-42}$ increases the generation of dimeric SDS-resistant polymers of $Aβ_{1-42}$ (FIGS. 32A and 32B), this dimeric species may be an integral intermediate in the formation of the SDS-resistant Aβ trimers, and may explain why $Aβ_{1-40}$ polymerization occurs more slowly.

AD Pathology

The present invention indicates that the manipulation of the brain biometal environment with specific agents acting directly (e.g. chelators and antioxidants) or indirectly (e.g., by improving cerebral energy metabolism) provides a means for therapeutic intervention in the prevention and treatment of Alzheimer's disease.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

All patents and publications cited in the present specification are incorporated by reference herein in their entirety.

What is claimed is:

1. A method of treating amyloidosis in a subject, said method comprising administering to said subject a combination of (a) a metal chelator selected from the group consisting of: bathocuproine, bathophenanthroline, DTPA, EDTA, EGTA, penicillamine, TETA, TPEN, and hydrophobic derivatives thereof; and (b) clioquinol, for a time and under conditions to bring about said treatment; wherein said combination reduces, inhibits or otherwise interferes with Aβ-mediated production of radical oxygen species.

2. The method of claim 1 wherein the metal chelator is bathocuproine.

3. The method of claim 1 further comprising administering a supplement selected from the group consisting of: ammonium salt, calcium salt, magnesium salt, and sodium salt.

4. The method of claim 3 wherein the supplement is magnesium salt.

5. The method of claim 1 further comprising administering to the subject an effective amount of a compound selected from the group consisting of: rifampicin disulfiram, indomethacin, and a pharmaceutically acceptable salt thereof.

6. A method of treating amyloidosis in a subject, said method comprising administering to said subject an effective amount of a combination of (a) a salt of a metal chelator, wherein said chelator is selected from the group consisting of: bathocuproine, bathophenanthroline, DTPA, EDTA, EGTA, penicillamine, TETA, TPEN, and hydrophobic derivatives thereof, and (b) clioquinol; wherein said salt of the metal chelator is selected from the group consisting of: ammonium, calcium, magnesium, and sodium: and wherein said combination reduces, inhibits or otherwise interferes with Aβ-mediated production of radical oxygen species.

7. The method of claim 6 wherein the metal chelator is bathocuproine.

8. The method of claim 6 wherein the salt of a metal chelator is a magnesium salt.

9. The method of claim 6 further comprising administering to said subject a compound selected from the group consisting of: rifampicin, disulfiram, indomethacin, and a pharmaceutically acceptable salt thereof.

10. A method of treating amyloidosis in a subject, said method comprising administering to said subject a combination of (a) a metal chelator selected from the group consisting of: bathocuproine, bathophenanthroline, DTPA, EDTA, EGTA, penicillamine, TETA, TPEN, and hydrophobic derivatives thereof; and (b) clioquinol, for a time and under conditions to bring about said treatment; wherein said combination prevents formation of Aβ amyloid, promotes, induces or otherwise facilitates resolubilization of Aβ deposits, or both.

11. The method of claim 10 wherein the metal chelator is bathocuproine.

12. The method of claim 10 further comprising administering a supplement selected from the group consisting of: ammonium salt, calcium salt, magnesium salt, and sodium salt.

13. The method of claim 12 wherein the supplement is magnesium salt.

14. The method of claim 10 further comprising administering to the subject an effective amount of a compound selected from the group consisting of: rifampicin, disulfiram, indomethacin, and a pharmaceutically acceptable salt thereof.

15. A method of treating amyloidosis in a subject, said method comprising administering to said subject an effective amount of a combination of (a) a salt of a metal chelator, wherein said chelator is selected from the group consisting of: bathocuproine, bathophenianthroline, DTPTA, EDTA, EGTA, penicillamine, TETA, TPEN, and hydrophobic derivatives thereof, and (b) clioquinol; wherein said salt of the metal chelator is selected from the group consisting of: ammonium, calcium, magnesium, and sodium; and wherein said combination prevents formation of Aβ amyloid, promotes, induces or otherwise facilitates resolubilization of Aβ deposits, or both.

16. The method of claim 15 wherein the metal chelator is bathocuproine.

17. The method of claim 15 wherein the salt of the metal chelator is a magnesium salt.

18. The method of claim 15 further comprising administering to said subject a compound selected from the group consisting of: rifampicin, disulfiram, indomethacin, and a pharmaceutically acceptable salt thereof.

19. A pharmaceutical composition for treatment of conditions caused by amyloidosis, Aβ-mediated ROS formation, or both, comprising: (a) a metal chelator selected from the group consisting of: bathocuproine, bathophenanthroline, DTPA, EDTA, EGTA, penicillamine, TETA, TPEN, and hydrophobic derivatives thereof; and (b) clioquinol, together with one or more pharmaceutically acceptable carriers or diluents.

20. The pharmaceutical composition of claim 19 wherein the metal chelator is bathocuproine.

21. The pharmaceutical composition of claim 19 further comprising a supplement selected from the group consisting of: ammonium salt, calcium salt, magnesium salt, and sodium salt.

22. The pharmaceutical composition of claim 21 wherein the supplement is a magnesium salt.

23. The pharmaceutical composition of claim 19 further comprising a compound selected from the group consisting of: rifampicin, disulfiram, and indomethacin.

24. A pharmaceutical composition for treatment of conditions caused by amyloidosis, Aβ-mediated ROS formation, or both, comprising a combination of (a) a salt of a metal chelator selected from the group consisting of: bathocuproine, bathophenanthrolinie, DTPA, EDTA, EGTA, penicillamine, TETA, TPEN, and hydrophobic derivatives thereof; and (b) clioquinol; wherein said salt of the metal chelator is selected from the group consisting of: ammonium, calcium, magnesium, and sodium, together with one or more pharmaceutically acceptable carriers or diluents.

25. The pharmaceutical composition of claim 24 wherein the metal chelator is bathocuproine.

26. The pharmaceutical composition of claim 24 wherein the salt of the metal chelator is a magnesium salt.

27. The pharmaceutical composition of claim 24 further comprising a compound selected from the group consisting of: rifampicin, disulfiram, and indomethacin.

28. A composition of matter comprising: (a) a metal chelator selected from the group consisting of: bathocuproine, bathophenanthroline, DTPA, EDTA, EGTA, penicillamine, TETA, TPEN, and hydrophobic derivatives thereof; and (b) clioquinol.

29. The composition of claim 28 wherein the metal chelator is bathocuproine.

30. The composition of claim 28 further comprising a supplement selected from the group consisting of: ammonium salt, calcium salt, magnesium salt, and sodium salt.

31. The composition of claim 30 wherein the supplement is a magnesium salt.

32. The composition of claim 28 further comprising a compound selected from the group consisting of: rifampicin, disulfiram, and indomethacin.

33. A composition of matter comprising a combination of (a) a salt of a metal chelator selected from the group consisting of: bathocuproine, bathophenanthroline, DTPA, EDTA, EGTA, penicillamine, TETA, TPEN, and hydrophobic derivatives thereof; and (b) clioquinol; wherein said salt of the metal chelator is selected from the group consisting of: ammonium, calcium, magnesium, and sodium.

34. The composition of claim 13 wherein the metal chelator is bathocuproine.

35. The composition of claim 33 wherein the salt of the chelator is a magnesium salt.

36. The composition of claim 33 further comprising a compound selected from the group consisting of: rifampicin, disulfiram, and indomethacin.

* * * * *